United States Patent
Bongiorni et al.

(10) Patent No.: US 11,479,763 B2
(45) Date of Patent: Oct. 25, 2022

(54) BACILLUS HOST CELLS PRODUCING β-GALACTOSIDASES AND LACTASES IN THE ABSENCE OF P-NITROBENZYLESTERASE SIDE ACTIVITY

(71) Applicant: DUPONT NUTRITION BIOSCIENCES APS, Copenhagen K (DK)

(72) Inventors: Cristina Bongiorni, Palo Alto, CA (US); Karina Hansen Kjaer, Brabrand (DK)

(73) Assignee: Dupont Nutrition Biosciences APS, Kongens Lyngby (DK)

( * ) Notice: Subject to any disclaimer, the term of this patent is extended or adjusted under 35 U.S.C. 154(b) by 0 days.

(21) Appl. No.: 16/603,100

(22) PCT Filed: Apr. 5, 2018

(86) PCT No.: PCT/US2018/026170
§ 371 (c)(1),
(2) Date: Oct. 4, 2019

(87) PCT Pub. No.: WO2018/187524
PCT Pub. Date: Oct. 11, 2018

(65) Prior Publication Data
US 2020/0123519 A1 Apr. 23, 2020

Related U.S. Application Data

(60) Provisional application No. 62/483,239, filed on Apr. 7, 2017.

(51) Int. Cl.
| | |
|---|---|
| C12N 9/38 | (2006.01) |
| A23C 9/12 | (2006.01) |
| C12N 1/20 | (2006.01) |
| C12N 15/75 | (2006.01) |
| C12N 1/21 | (2006.01) |

(52) U.S. Cl.
CPC .......... *C12N 9/2471* (2013.01); *A23C 9/1206* (2013.01); *C12N 1/20* (2013.01); *C12N 15/75* (2013.01); *C12Y 302/01023* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 5,945,325 A | * | 8/1999 | Arnold | C12N 9/18 435/197 |
| 10,842,163 B2 | * | 11/2020 | Larsen | A23C 9/1206 |
| 2006/0073559 A1 | * | 4/2006 | Ferrari | C12N 1/205 435/221 |
| 2015/0223481 A1 | * | 8/2015 | Larsen | A23C 9/1206 426/42 |

FOREIGN PATENT DOCUMENTS

WO   WO-2016071504 A1 * 5/2016 .......... A23L 33/135

OTHER PUBLICATIONS

Kim et al., Characterization of a thermostable recombinant beta-galactosidase from Thermotoga maritima, J. Appl. Microbiol. 97, 2004, 1006-14. (Year: 2004).*
Koo et al., Construction and Analysis of Two Genome-Scale Deletion Libraries for Bacillus subtilis, Cell Systems 4, 2017, 291-305. (Year: 2017).*
Zock et al., The Bacillus subtilis pnbA gene encoding p-nitrobenzyl esterase: cloning, sequence and high-level expression in *Escherichia coli*, Gene 151, 1994, 37-43. (Year: 1994).*
Altenbuchner, Editing of the Bacillus subtilis Genome by the CRISPR-Cas9 System, Appl. Environ. Microbiol. 82, 2016, 5421-27. (Year: 2016).*
Wierdl et al., Molecular Modeling of CPT-11 Metabolism by Carboxylesterases (CEs): Use of pnb CE as a Model, Biochemistry 43, 2004, 1874-82. (Year: 2004).*
Uniprot, Accession No. O07012, 2016, www.uniprot.org. (Year: 2016).*

* cited by examiner

*Primary Examiner* — Robert B Mondesi
*Assistant Examiner* — Todd M Epstein

(57) ABSTRACT

Certain embodiments of the disclosure are directed to the expression/production of β-galactosidases in recombinant *Bacillus* spp. host cells having reduced or eliminated para-nitrobenzylesterase activity.

31 Claims, 14 Drawing Sheets
Specification includes a Sequence Listing.

**Bacillus subtilis (168) *para*-Nitrobenzylesterase (SEQ ID NO: 2)**

MTHQIVTTQYGKVKGTTENGVHKWKGIPYAKPPVGQWRFKAPEPPEVWEDVLDATAYGSICPQPSDLLSL (70)

SYTELPRQSEDCLYVNVFAPDTPSKNLPVMVWIHGGAFYLGAGSEPLYDGSKLAAQGEVIVVTLNYRLGP (140)

FGFLHLSSFNEAYSDNLGLLDQAAALKWVRENISAFGGDPDNVTVFGEsAGGMSIAALLAMPAAKGLFQK (210)

AIMESGASRTMTKEQAASTSAAFLQVLGINEGQLDKLHTVSAEDLLKAADQLRIAEKENIFQLFFQPALD (280)

PKTLPEEPEKAIAEGAASGIPLLIGTTRDeGYLFFTPDSDVHSQETLDAALEYLLGKPLAEKVADLYPRS (350)

LESQIHMMTDLLFWRPAVAYASAQSHYAPVWMYRFDWHPKKPPYNKAFhALELPFVFGNLDGLERMAKAE (420)

ITTDEVKQLSHTIQSAWITFAKTGNPSTEAVNWPAYHEETRETLILDSEITIENDPESEKRQKLFPSKGE (489)

FIG. 13

SEQUENCE LISTING

<160> NUMBER OF SEQ ID NOS: 26

<210> SEQ ID NO 1
<211> LENGTH: 1470
<212> TYPE: DNA
<213> ORGANISM: Bacillus subtilis

<400> SEQUENCE: 1

```
atgactcatc aaatagtaac gactcaatac ggcaaagtaa aaggcacaac ggaaaacggc      60
gtacataagt ggaaaggcat cccctatgcc aagccgcctg tcggacaatg gcgttttaaa     120
gcacctgagc cgcctgaagt gtgggaagat gtgcttgatg ccacagcgta cggctctatt     180
tgcccgcagc cgtctgattt gctgtcactt tcgtatactg agctgccccg ccagtccgag     240
gattgcttgt atgtcaatgt atttgcgcct gacaccccaa gtaaaaatct tcctgtcatg     300
gtgtggattc acggaggcgc tttttatcta ggagcgggca gtgagccatt gtatgacgga     360
tcaaaacttg cggcacaggg agaagtcatt gtcgttacat tgaactatcg gctggggccg     420
tttggctttt tgcacttgtc ttcatttaat gaggcgtatt ctgataacct tgggcttta      480 gaccaagccg ccgcgctgaa atgggtgcga gagaatattt cagcgtttgg cggtgatccc     540
```

-continued

```
gataacgtaa cagtatttgg agaatccgcc ggcgggatga gcattgccgc gctgcttgct      600
atgcctgcgg caaaaggcct gttccagaaa gcaatcatgg aaagcggcgc ttctcgaacg      660
atgacgaaag aacaagcggc gagcacctcg gcagccttt  tacaggtcct tgggattaac      720
gagggccaac tggataaatt gcatacggtt tctgcggaag atttgctaaa agcggctgat      780
cagcttcgga ttgcagaaaa agaaaatatc tttcagctgt tcttccagcc cgcccttgat      840
ccgaaaacgc tgcctgaaga accagaaaaa gcgatcgcag aagggctgc  ttccggtatt      900 ccgctattaa ttggaacaac ccgtgatgaa ggatatttat ttttcacccc ggattcagac      960
gttcattctc aggaaacgct tgatgcagcg ctcgagtatt tactagggaa gccgctggca     1020
gagaaagttg ccgatttgta tccgcgttct ctggaaagcc aaattcatat gatgactgat     1080
ttattatttt ggcgccctgc cgtcgcctat gcatccgcac agtctcatta cgcccctgtc     1140
tggatgtaca ggttcgattg gcacccgaag aagccgccgt acaataaagc gtttcacgca     1200
ttagagcttc cttttgtctt tggaaatctg gacggattgg aacgaatggc aaaagcggag     1260
attacggatg aggtgaaaca gctttctcac acgatacaat cagcgtggat cacgttcgcc     1320
aaaacaggaa acccaagcac cgaagctgtg aattggcctg cgtatcatga agaaacgaga     1380
gagacgctga ttttagactc agagattacg atcgaaaacg atcccgaatc tgaaaaaagg     1440
cagaagctat tcccttcaaa aggagaataa                                      1470
```

<210> SEQ ID NO 2
<211> LENGTH: 489
<212> TYPE: PRT
<213> ORGANISM: Bacillus subtilis

<400> SEQUENCE: 2

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Glu Val Trp
        35                  40                  45

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205
```

```
Gln Lys Ala Ile Met Glu Ser Gly Ala Ser Arg Thr Met Thr Lys Glu
    210                 215                 220
Gln Ala Ala Ser Thr Ser Ala Ala Phe Leu Gln Val Leu Gly Ile Asn
225                 230                 235                 240
Glu Gly Gln Leu Asp Lys Leu His Thr Val Ser Ala Glu Asp Leu Leu
                245                 250                 255
Lys Ala Ala Asp Gln Leu Arg Ile Ala Glu Lys Glu Asn Ile Phe Gln
            260                 265                 270
Leu Phe Phe Gln Pro Ala Leu Asp Pro Lys Thr Leu Pro Glu Glu Pro
        275                 280                 285
Glu Lys Ala Ile Ala Glu Gly Ala Ser Gly Ile Pro Leu Leu Ile
    290                 295                 300
Gly Thr Thr Arg Asp Glu Gly Tyr Leu Phe Phe Thr Pro Asp Ser Asp
305                 310                 315                 320
Val His Ser Gln Glu Thr Leu Asp Ala Ala Leu Glu Tyr Leu Leu Gly
                325                 330                 335
Lys Pro Leu Ala Glu Lys Val Ala Asp Leu Tyr Pro Arg Ser Leu Glu
            340                 345                 350
Ser Gln Ile His Met Met Thr Asp Leu Leu Phe Trp Arg Pro Ala Val
        355                 360                 365
Ala Tyr Ala Ser Ala Gln Ser His Tyr Ala Pro Val Trp Met Tyr Arg
    370                 375                 380
Phe Asp Trp His Pro Lys Lys Pro Pro Tyr Asn Lys Ala Phe His Ala
385                 390                 395                 400
Leu Glu Leu Pro Phe Val Phe Gly Asn Leu Asp Gly Leu Glu Arg Met
                405                 410                 415
Ala Lys Ala Glu Ile Thr Asp Glu Val Lys Gln Leu Ser His Thr Ile
            420                 425                 430
Gln Ser Ala Trp Ile Thr Phe Ala Lys Thr Gly Asn Pro Ser Thr Glu
        435                 440                 445
Ala Val Asn Trp Pro Ala Tyr His Glu Glu Thr Arg Glu Thr Leu Ile
    450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
                485

<210> SEQ ID NO 3
<211> LENGTH: 5160
<212> TYPE: DNA
<213> ORGANISM: Bifidobacterium bifidum

<400> SEQUENCE: 3
gcagttgaag atgcaacaag aagcgatagc acaacacaaa tgtcatcaac accggaagtt      60
gtttattcat cagcggtcga tagcaaacaa aatcgcacaa gcgattttga tgcgaactgg     120
aaatttatgc tgtcagatag cgttcaagca caagatccgg catttgatga ttcagcatgg     180
caacaagttg atctgccgca tgattatagc atcacacaga aatatagcca aagcaatgaa     240
gcagaatcag catatcttcc gggaggcaca ggctggtata gaaaaagctt acaattgat     300 agagatctgg caggcaaacg cattgcgatt aatttgatg gcgtctatat gaatgcaaca     360
gtctggttta tggcgttaa actgggcaca catccgtatg ctattcacc gttttcattt     420 gatctgacag gcaatgcaaa atttggcgga gaaaacacaa ttgtcgtcaa agttgaaaat     480
```

```
agactgccgt catcaagatg gtattcaggc agcggcattt atagagatgt tacactgaca    540
gttacagatg gcgttcatgt tggcaataat ggcgtcgcaa ttaaaacacc gtcactggca    600
acacaaaatg gcggagatgt cacaatgaac ctgacaacaa aagtcgcgaa tgatacagaa    660
gcagcagcga acattacact gaaacagaca gttttttccga aaggcggaaa aacggatgca    720
gcaattggca cagttacaac agcatcaaaa tcaattgcag caggcgcatc agcagatgtt    780
acaagcacaa ttacagcagc aagcccgaaa ctgtggtcaa ttaaaaaccc gaacctgtat    840
acagttagaa cagaagttct gaacggaggc aaagttctgg atacatatga tacagaatat    900
ggctttcgct ggacaggctt tgatgcaaca tcaggctttt cactgaatgg cgaaaaagtc    960
aaactgaaag gcgttagcat gcatcatgat caaggctcac ttggcgcagt tgcaaataga   1020
cgcgcaattg aaagacaagt cgaaatcctg caaaaaatgg gcgtcaatag cattcgcaca   1080
acacataatc cggcagcaaa agcactgatt gatgtctgca atgaaaaagg cgttctggtt   1140
gtcgaagaag tctttgatat gtggaaccgc agcaaaaatg gcaacacgga agattatggc   1200
aaatggtttg gccaagcaat tgcaggcgat aatgcagttc tgggaggcga taaagatgaa   1260
acatgggcga aatttgatct tacatcaaca attaaccgcg atagaaatgc accgtcagtt   1320
attatgtggt cactgggcaa tgaaatgatg gaaggcattt caggctcagt ttcaggctttt  1380 ccggcaacat cagcaaaact ggttgcatgg acaaaagcag cagattcaac aagaccgatg   1440
acatatggcg ataacaaaat taaagcgaac tggaacgaat caaatacaat gggcgataat   1500
ctgacagcaa atggcggagt tgttggcaca aattattcag atggcgcaaa ctatgataaa   1560
attcgtacaa cacatccgtc atgggcaatt tatggctcag aaacagcatc agcgattaat   1620
agccgtggca tttataatag aacaacaggc ggagcacaat catcagataa acagctgaca   1680
agctatgata ttcagcagt tggctgggga gcagttgcat catcagcatg gtatgatgtt   1740
gttcagagag attttgtcgc aggcacatat gtttggacag gatttgatta tctgggcgaa   1800
ccgacaccgt ggaatggcac aggctcaggc gcagttggct catggccgtc accgaaaaat   1860
agctattttg gcatcgttga tacagcaggc tttccgaaag atacatatta ttttttatcag  1920 agccagtgga atgatgatgt tcatacactg catattcttc cggcatggaa tgaaaatgtt   1980
gttgcaaaag gctcaggcaa taatgttccg gttgtcgttt atacagatgc agcgaaagtg   2040
aaactgtatt ttacaccgaa aggctcaaca gaaaaaagac tgatcggcga aaaatcattt   2100
acaaaaaaaa caacagcggc aggctataca tatcaagtct atgaaggcag cgataaagat   2160
tcaacagcgc ataaaaacat gtatctgaca tggaatgttc cgtgggcaga aggcacaatt   2220
tcagcggaag cgtatgatga aaataatcgc ctgattccgg aaggcagcac agaaggcaac   2280
gcatcagtta caacaacagg caaagcagca aaactgaaag cagatgcgga tcgcaaaaca   2340
attacagcgg atggcaaaga tctgtcatat attgaagtcg atgtcacaga tgcaaatggc   2400
catattgttc cggatgcagc aaatagagtc acatttgatg ttaaaggcgc aggcaaactg   2460
gttggcgttg ataatggctc atcaccggat catgattcat atcaagcgga taccgcaaa   2520 gcattttcag gcaaagtcct ggcaattgtt cagtcaacaa aagaagcagg cgaaattaca   2580
gttacagcaa aagcagatgg cctgcaatca agcacagtta aaattgcaac aacagcagtt   2640
ccgggaacaa gcacagaaaa aacagtccgc agctttttatt acagccgcaa ctattatgtc   2700
aaaacaggca caaaaccgat tctgccgtca gatgttgaag ttcgctattc agatggaaca   2760
agcgatagac aaaaacgttac atgggatgca gtttcagatg atcaaattgc aaaagcaggc   2820
tcattttcag ttgcaggcac agttgcaggc caaaaaatta gcgttcgcgt cacaatgatt   2880
```

-continued

```
gatgaaattg gcgcactgct gaattattca gcaagcacac cggttggcac accggcagtt      2940
cttccgggat caagaccggc agtcctgccg gatggcacag tcacatcagc aaattttgca      3000
gtccattgga caaaaccggc agatacagtc tataatacag caggcacagt caaagtaccg      3060
ggaacagcaa cagttttttgg caaagaattt aaagtcacag cgacaattag agttcaaaga      3120
agccaagtta caattggctc atcagtttca ggaaatgcac tgagactgac acaaaatatt      3180
ccggcagata acaatcaga tacactggat gcgattaaag atggctcaac aacagttgat       3240
gcaaatacag gcggaggcgc aaatccgtca gcatggacaa attgggcata ttcaaaagca      3300
ggccataaca cagcggaaat tacatttgaa tatgcgacag aacaacaact gggccagatc      3360
gtcatgtatt ttttttcgcga tagcaatgca gttagatttc cggatgctgg caaaacaaaa     3420
attcagatca gcgcagatgg caaaaattgg acagatctgg cagcaacaga aacaattgca      3480
gcgcaagaat caagcgatag agtcaaaccg tatacatatg attttgcacc ggttggcgca      3540
acatttgtta aagtgacagt cacaaacgca gatacaacaa caccgtcagg cgttgtttgc      3600
gcaggcctga cagaaattga actgaaaaca gcgacaagca aatttgtcac aaatacatca      3660
gcagcactgt catcacttac agtcaatggc acaaaagttt cagattcagt tctggcagca      3720
ggctcatata acacaccggc aattatcgca gatgttaaag cggaaggcga aggcaatgca      3780
agcgttacag tccttccggc acatgataat gttattcgcg tcattacaga aagcgaagat      3840
catgtcacac gcaaaacatt tacaatcaac ctgggcacag aacaagaatt tccggctgat      3900
tcagatgaaa gagattatcc ggcagcagat atgacagtca cagttggctc agaacaaaca      3960
tcaggcacag caacagaagg accgaaaaaa tttgcagtcg atggcaacac atcaacatat      4020
tggcatagca attggacacc gacaacagtt aatgatctgt ggatcgcgtt tgaactgcaa      4080
aaaccgacaa aactggatgc actgagatat cttccgcgtc cggcaggctc aaaaaatggc      4140
agcgtcacag aatataaagt tcaggtgtca gatgatggaa caaactggac agatgcaggc      4200
tcaggcacat ggacaacgga ttatggctgg aaactggcgg aatttaatca accggtcaca      4260
acaaaacatg ttagactgaa agcggttcat acatatgcag atagcggcaa cgataaattt      4320
atgagcgcaa gcgaaattag actgagaaaa gcggtcgata caacggatat ttcaggcgca      4380
acagttacag ttccggcaaa actgacagtt gatagagttg atgcagatca tccggcaaca      4440
tttgcaacaa aagatgtcac agttacactg ggagatgcaa cactgagata tggcgttgat      4500
tatctgctgg attatgcagg caatacagca gttggcaaag caacagtgac agttagaggc      4560
attgataaat attcaggcac agtcgcgaaa acatttacaa ttgaactgaa aaatgcaccg      4620
gcaccggaac cgacactgac atcagttagc gtcaaaacaa aaccgagcaa actgacatat      4680
gttgtcggag atgcatttga tccggcaggc ctggttctgc aacatgatag acaagcagat      4740
agacctccgc aaccgctggt tggcgaacaa gcggatgaac gcggactgac atgcggcaca      4800
agatgcgata gagttgaaca actgcgcaaa catgaaaata gagaagcgca tagaacaggc      4860
ctggatcatc tggaatttgt tggcgcagca gatggcgcag ttggagaaca agcaacattt      4920
aaagtccatg tccatgcaga tcagggagat ggcagacatg atgatgcaga tgaacgcgat      4980
attgatccgt atgttccggt cgatcatgca gttggcgaac tggcaagagc agcatgccat      5040
catgttattg gcctgagagt cgatacacat agacttaaag caagcggctt tcaaattccg      5100
gctgatgata tggcagaaat cgatcgcatt acaggctttc atcgttttga acgccatgtc      5160
```

<210> SEQ ID NO 4

<211> LENGTH: 1720
<212> TYPE: PRT
<213> ORGANISM: Bifidobacterium bifidum

<400> SEQUENCE: 4

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
```

-continued

```
            385                 390                 395                 400
        Trp Phe Gly Gln Ala Ile Ala Gly Asp Asn Ala Val Leu Gly Gly Asp
                        405                 410                 415
        Lys Asp Glu Thr Trp Ala Lys Phe Asp Leu Thr Ser Thr Ile Asn Arg
                420                 425                 430
        Asp Arg Asn Ala Pro Ser Val Ile Met Trp Ser Leu Gly Asn Glu Met
                        435                 440                 445
        Met Glu Gly Ile Ser Gly Ser Val Ser Gly Phe Pro Ala Thr Ser Ala
                450                 455                 460
        Lys Leu Val Ala Trp Thr Lys Ala Ala Asp Ser Thr Arg Pro Met Thr
        465                 470                 475                 480
        Tyr Gly Asp Asn Lys Ile Lys Ala Asn Trp Asn Glu Ser Asn Thr Met
                        485                 490                 495
        Gly Asp Asn Leu Thr Ala Asn Gly Gly Val Val Gly Thr Asn Tyr Ser
                        500                 505                 510
        Asp Gly Ala Asn Tyr Asp Lys Ile Arg Thr Thr His Pro Ser Trp Ala
                        515                 520                 525
        Ile Tyr Gly Ser Glu Thr Ala Ser Ala Ile Asn Ser Arg Gly Ile Tyr
                530                 535                 540
        Asn Arg Thr Thr Gly Gly Ala Gln Ser Ser Asp Lys Gln Leu Thr Ser
        545                 550                 555                 560
        Tyr Asp Asn Ser Ala Val Gly Trp Gly Ala Val Ala Ser Ser Ala Trp
                        565                 570                 575
        Tyr Asp Val Val Gln Arg Asp Phe Val Ala Gly Thr Tyr Val Trp Thr
                        580                 585                 590
        Gly Phe Asp Tyr Leu Gly Glu Pro Thr Pro Trp Asn Gly Thr Gly Ser
                        595                 600                 605
        Gly Ala Val Gly Ser Trp Pro Ser Pro Lys Asn Ser Tyr Phe Gly Ile
                        610                 615                 620
        Val Asp Thr Ala Gly Phe Pro Lys Asp Thr Tyr Tyr Phe Tyr Gln Ser
        625                 630                 635                 640
        Gln Trp Asn Asp Asp Val His Thr Leu His Ile Leu Pro Ala Trp Asn
                        645                 650                 655
        Glu Asn Val Val Ala Lys Gly Ser Gly Asn Asn Val Pro Val Val Val
                        660                 665                 670
        Tyr Thr Asp Ala Ala Lys Val Lys Leu Tyr Phe Thr Pro Lys Gly Ser
                        675                 680                 685
        Thr Glu Lys Arg Leu Ile Gly Glu Lys Ser Phe Thr Lys Lys Thr Thr
                690                 695                 700
        Ala Ala Gly Tyr Thr Tyr Gln Val Tyr Glu Gly Ser Asp Lys Asp Ser
        705                 710                 715                 720
        Thr Ala His Lys Asn Met Tyr Leu Thr Trp Asn Val Pro Trp Ala Glu
                        725                 730                 735
        Gly Thr Ile Ser Ala Glu Ala Tyr Asp Glu Asn Asn Arg Leu Ile Pro
                        740                 745                 750
        Glu Gly Ser Thr Glu Gly Asn Ala Ser Val Thr Thr Gly Lys Ala
                        755                 760                 765
        Ala Lys Leu Lys Ala Asp Ala Asp Arg Lys Thr Ile Thr Ala Asp Gly
                770                 775                 780
        Lys Asp Leu Ser Tyr Ile Glu Val Asp Val Thr Asp Ala Asn Gly His
        785                 790                 795                 800
        Ile Val Pro Asp Ala Ala Asn Arg Val Thr Phe Asp Val Lys Gly Ala
                        805                 810                 815
```

```
Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
            850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Ser Arg Asn
            885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
            930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr
            1010                1015                1020

Val Phe Gly Lys Glu Phe Lys Val Thr Ala Thr Ile Arg Val Gln
            1025                1030                1035

Arg Ser Gln Val Thr Ile Gly Ser Ser Val Ser Gly Asn Ala Leu
            1040                1045                1050

Arg Leu Thr Gln Asn Ile Pro Ala Asp Lys Gln Ser Asp Thr Leu
            1055                1060                1065

Asp Ala Ile Lys Asp Gly Ser Thr Thr Val Asp Ala Asn Thr Gly
            1070                1075                1080

Gly Gly Ala Asn Pro Ser Ala Trp Thr Asn Trp Ala Tyr Ser Lys
            1085                1090                1095

Ala Gly His Asn Thr Ala Glu Ile Thr Phe Glu Tyr Ala Thr Glu
            1100                1105                1110

Gln Gln Leu Gly Gln Ile Val Met Tyr Phe Phe Arg Asp Ser Asn
            1115                1120                1125

Ala Val Arg Phe Pro Asp Ala Gly Lys Thr Lys Ile Gln Ile Ser
            1130                1135                1140

Ala Asp Gly Lys Asn Trp Thr Asp Leu Ala Ala Thr Glu Thr Ile
            1145                1150                1155

Ala Ala Gln Glu Ser Ser Asp Arg Val Lys Pro Tyr Thr Tyr Asp
            1160                1165                1170

Phe Ala Pro Val Gly Ala Thr Phe Val Lys Val Thr Val Thr Asn
            1175                1180                1185

Ala Asp Thr Thr Thr Pro Ser Gly Val Val Cys Ala Gly Leu Thr
            1190                1195                1200

Glu Ile Glu Leu Lys Thr Ala Thr Ser Lys Phe Val Thr Asn Thr
            1205                1210                1215
```

```
Ser Ala Ala Leu Ser Ser Leu Thr Val Asn Gly Thr Lys Val Ser
1220                1225                1230

Asp Ser Val Leu Ala Ala Gly Ser Tyr Asn Thr Pro Ala Ile Ile
1235                1240                1245

Ala Asp Val Lys Ala Glu Gly Glu Gly Asn Ala Ser Val Thr Val
1250                1255                1260

Leu Pro Ala His Asp Asn Val Ile Arg Val Ile Thr Glu Ser Glu
1265                1270                1275

Asp His Val Thr Arg Lys Thr Phe Thr Ile Asn Leu Gly Thr Glu
1280                1285                1290

Gln Glu Phe Pro Ala Asp Ser Asp Glu Arg Asp Tyr Pro Ala Ala
1295                1300                1305

Asp Met Thr Val Thr Val Gly Ser Glu Gln Thr Ser Gly Thr Ala
1310                1315                1320

Thr Glu Gly Pro Lys Lys Phe Ala Val Asp Gly Asn Thr Ser Thr
1325                1330                1335

Tyr Trp His Ser Asn Trp Thr Pro Thr Thr Val Asn Asp Leu Trp
1340                1345                1350

Ile Ala Phe Glu Leu Gln Lys Pro Thr Lys Leu Asp Ala Leu Arg
1355                1360                1365

Tyr Leu Pro Arg Pro Ala Gly Ser Lys Asn Gly Ser Val Thr Glu
1370                1375                1380

Tyr Lys Val Gln Val Ser Asp Gly Thr Asn Trp Thr Asp Ala
1385                1390                1395

Gly Ser Gly Thr Trp Thr Thr Asp Tyr Gly Trp Lys Leu Ala Glu
1400                1405                1410

Phe Asn Gln Pro Val Thr Thr Lys His Val Arg Leu Lys Ala Val
1415                1420                1425

His Thr Tyr Ala Asp Ser Gly Asn Asp Lys Phe Met Ser Ala Ser
1430                1435                1440

Glu Ile Arg Leu Arg Lys Ala Val Asp Thr Thr Asp Ile Ser Gly
1445                1450                1455

Ala Thr Val Thr Val Pro Ala Lys Leu Thr Val Asp Arg Val Asp
1460                1465                1470

Ala Asp His Pro Ala Thr Phe Ala Thr Lys Asp Val Thr Val Thr
1475                1480                1485

Leu Gly Asp Ala Thr Leu Arg Tyr Gly Val Asp Tyr Leu Leu Asp
1490                1495                1500

Tyr Ala Gly Asn Thr Ala Val Gly Lys Ala Thr Val Thr Val Arg
1505                1510                1515

Gly Ile Asp Lys Tyr Ser Gly Thr Val Ala Lys Thr Phe Thr Ile
1520                1525                1530

Glu Leu Lys Asn Ala Pro Ala Pro Glu Pro Thr Leu Thr Ser Val
1535                1540                1545

Ser Val Lys Thr Lys Pro Ser Lys Leu Thr Tyr Val Val Gly Asp
1550                1555                1560

Ala Phe Asp Pro Ala Gly Leu Val Leu Gln His Asp Arg Gln Ala
1565                1570                1575

Asp Arg Pro Pro Gln Pro Leu Val Gly Glu Gln Ala Asp Glu Arg
1580                1585                1590

Gly Leu Thr Cys Gly Thr Arg Cys Asp Arg Val Glu Gln Leu Arg
1595                1600                1605

Lys His Glu Asn Arg Glu Ala His Arg Thr Gly Leu Asp His Leu
```

| | | | | | | | | | | |
|---|---|---|---|---|---|---|---|---|---|---|
| | 1610 | | | 1615 | | | | 1620 | | |
| Glu | Phe | Val | Gly | Ala | Ala | Asp | Gly | Ala | Val | Gly |
| | 1625 | | | | 1630 | | | | 1635 | |
| Glu | Gln | Ala | Thr | | | | | | | |

Phe Lys Val His Val His Ala Asp Gln Gly Asp Gly Arg His Asp
    1640            1645            1650

Asp Ala Asp Glu Arg Asp Ile Asp Pro His Val Pro Val Asp His
    1655            1660            1665

Ala Val Gly Glu Leu Ala Arg Ala Ala Cys His His Val Ile Gly
    1670            1675            1680

Leu Arg Val Asp Thr His Arg Leu Lys Ala Ser Gly Phe Gln Ile
    1685            1690            1695

Pro Ala Asp Asp Met Ala Glu Ile Asp Arg Ile Thr Gly Phe His
    1700            1705            1710

Arg Phe Glu Arg His Val Gly
    1715            1720

<210> SEQ ID NO 5
<211> LENGTH: 2661
<212> TYPE: DNA
<213> ORGANISM: Bifidobacterium bifidum

<400> SEQUENCE: 5

```
gttgaagatg caacaagaag cgatagcaca acacaaatgt catcaacacc ggaagttgtt    60
tattcatcag cggtcgatag caaacaaaat cgcacaagcg attttgatgc gaactggaaa   120
tttatgctgt cagatagcgt tcaagcacaa gatccggcat tgatgattc agcatggcaa   180
caagttgatc tgccgcatga ttatagcatc acacagaaat atagccaaag caatgaagca   240
gaatcagcat atcttccggg aggcacaggc tggtatagaa aaagctttac aattgataga   300
gatctggcag gcaaacgcat tgcgattaat tttgatggcg tctatatgaa tgcaacagtc   360
tggtttaatg cgttaaaact gggcacacat ccgtatggct attcaccgtt tcatttgat   420
ctgacaggca atgcaaaatt tggcggagaa acacaattg tcgtcaaagt tgaaaataga   480
ctgccgtcat caagatggta ttcaggcagc ggcatttata gagatgttac actgacagtt   540
acagatggcg ttcatgttgg caataatggc gtcgcaatta aaacaccgtc actggcaaca   600
caaaatggcg gagatgtcac aatgaacctg acaacaaaag tcgcgaatga tacagaagca   660
gcagcgaaca ttacactgaa acagacagtt tttccgaaag cggaaaaaac ggatgcagca   720
attggcacag ttacaacagc atcaaaatca attgcagcag cgcatcagc agatgttaca   780
agcacaatta cagcagcaag cccgaaactg tggtcaatta aaaacccgaa cctgtataca   840
gttagaacag aagttctgaa cggaggcaaa gttctggata catatgatac agaatatggc   900
tttcgctgga caggctttga tgcaacatca ggcttttcac tgaatggcga aaaagtcaaa   960
ctgaaaggcg ttagcatgca tcatgatcaa ggctcacttg gcgcagttgc aaatagacgc  1020
gcaattgaaa acaagtcga aatcctgcaa aaaatgggcg tcaatagcat cgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tggcaatga atgatgaa ggcatttcag gctcagtttc aggctttccg  1380
gcaacatcag caaaactggt tgcatggaca aaagcagcag attcaacaag accgatgaca  1440
```

```
tatggcgata caaaattaa agcgaactgg aacgaatcaa atacaatggg cgataatctg   1500
acagcaaatg gcggagttgt tggcacaaat tattcagatg gcgcaaacta tgataaaatt   1560
cgtacaacac atccgtcatg ggcaatttat ggctcagaaa cagcatcagc gattaatagc   1620
cgtggcattt ataatagaac aacaggcgga gcacaatcat cagataaaca gctgacaagc   1680
tatgataatt cagcagttgg ctggggagca gttgcatcat cagcatggta tgatgttgtt   1740
cagagagatt ttgtcgcagg cacatatgtt tggacaggat tgattatct ggcgaaccg    1800 acaccgtgga atggcacagg ctcaggcgca gttggctcat ggccgtcacc gaaaaatagc   1860
tattttggca tcgttgatac agcaggcttt ccgaaagata catattattt ttatcagagc   1920
cagtggaatg atgatgttca tacactgcat attcttccgg catggaatga aaatgttgtt   1980
gcaaaaggct caggcaataa tgttccggtt gtcgtttata cagatgcagc gaaagtgaaa   2040
ctgtatttta caccgaaagg ctcaacagaa aaaagactga tcggcgaaaa atcatttaca   2100
aaaaaaacaa cagcggcagg ctatacatat caagtctatg aaggcagcga taagattca   2160 acagcgcata aaaacatgta tctgacatgg aatgttccgt gggcagaagg cacaatttca   2220
gcggaagcgt atgatgaaaa taatcgcctg attccggaag gcagcacaga aggcaacgca   2280
tcagttacaa caacaggcaa agcagcaaaa ctgaaagcag atgcggatcg caaaacaatt   2340
acagcggatg caaagatct gtcatatatt gaagtcgatg tcacagatgc aaatggccat   2400
attgttccgg atgcagcaaa tagagtcaca tttgatgtta aaggcgcagg caaactggtt   2460
ggcgttgata atggctcatc accggatcat gattcatatc aagcggataa ccgcaaagca   2520
ttttcaggca aagtcctggc aattgttcag tcaacaaaag aagcaggcga attacagtt   2580 acagcaaaag cagatggcct gcaatcaagc acagttaaaa ttgcaacaac agcagttccg   2640
ggaacaagca cagaaaaaac a                                            2661
```

<210> SEQ ID NO 6
<211> LENGTH: 887
<212> TYPE: PRT
<213> ORGANISM: Bifidobacterium bifidum

<400> SEQUENCE: 6

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160
```

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
        610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr
                885

<210> SEQ ID NO 7
<211> LENGTH: 2895
<212> TYPE: DNA
<213> ORGANISM: Bifidobacterium bifidum

<400> SEQUENCE: 7
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat tgatgattc agcatggcaa      180 caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360

```
tggtttaatg cgttaaaact gggcacacat ccgtatggct attcaccgtt ttcatttgat    420
ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcgaaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa acaagtcga atcctgcaa aaaatgggcg tcaatagcat tcgcacaaca   1080
cataatccgg cagcaaaagc actgattgat gtctgcaatg aaaaaggcgt tctggttgtc   1140
gaagaagtct ttgatatgtg aaccgcagc aaaaatggca acacgaaga ttatggcaaa   1200 tggtttggcc aagcaattgc aggcgataat gcagttctgg gaggcgataa agatgaaaca   1260
tgggcgaaat ttgatcttac atcaacaatt aaccgcgata gaaatgcacc gtcagttatt   1320
atgtggtcac tgggcaatga aatgatggaa ggcatttcag gctcagtttc aggctttccg   1380
gcaacatcag caaaactggt tgcatggaca aaagcagcag attcaacaag accgatgaca   1440
tatggcgata acaaaattaa agcgaactgg aacgaatcaa atacaatggg cgataatctg   1500
acagcaaatg gcggagttgt tggcacaaat tattcagatg gcgcaaacta tgataaaatt   1560
cgtacaacac atccgtcatg gcaatttat ggctcagaaa cagcatcagc gattaatagc   1620
cgtggcattt ataatagaac aacaggcgga gcacaatcat cagataaaca gctgacaagc   1680
tatgataatt cagcagttgg ctggggagca gttgcatcat cagcatggta tgatgttgtt   1740
cagagagatt ttgtcgcagg cacatatgtt tggacaggat ttgattatct gggcgaaccg   1800
acaccgtgga atggcacagg ctcaggcgca gttggctcat ggccgtcacc gaaaaatagc   1860
tattttggca tcgttgatac agcaggcttt ccgaaagata catattattt ttatcagagc   1920
cagtggaatg atgatgttca tacactgcat attcttccgg catggaatga aaatgttgtt   1980
gcaaaaggct caggcaataa tgttccggtt gtcgtttata cagatgcagc gaaagtgaaa   2040
ctgtatttta caccgaaagg ctcaacagaa aaaagactga tcggcgaaaa atcatttaca   2100
aaaaaaacaa cagcggcagg ctatacatat caagtctatg aaggcagcga taaagattca   2160
acagcgcata aaacatgta tctgacatgg aatgttccgt gggcagaagg cacaatttca   2220
gcggaagcgt atgatgaaaa taatcgcctg attccggaag gcagcacaga aggcaacgca   2280
tcagttacaa aacaggcaa agcagcaaaa ctgaaagcag atgcggatcg caaaacaatt   2340
acagcggatg gcaaagatct gtcatatatt gaagtcgatg tcacagatgc aaatggccat   2400
attgttccgg atgcagcaaa tagagtcaca tttgatgtta aaggcgcagg caaactggtt   2460
ggcgttgata atggctcatc accggatcat gattcatatc aagcggataa ccgcaaagca   2520
ttttcaggca agtcctggc aattgttcag tcaacaaaag aagcaggcga aattacagtt   2580
acagcaaaag cagatggcct gcaatcaagc acagttaaaa ttgcaacaac agcagttccg   2640
ggaacaagca cagaaaaaac agtccgcagc ttttattaca gccgcaacta ttatgtcaaa   2700
```

-continued

```
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactg                                                    2895
```

<210> SEQ ID NO 8
<211> LENGTH: 965
<212> TYPE: PRT
<213> ORGANISM: Bifidobacterium bifidum

<400> SEQUENCE: 8

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
        210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
        290                 295                 300

Gly Phe Asp Ala Thr Ser Gly Phe Ser Leu Asn Gly Glu Lys Val Lys
305                 310                 315                 320

Leu Lys Gly Val Ser Met His Asp Gln Gly Ser Leu Gly Ala Val
                325                 330                 335
```

```
Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
        450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
        530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
        610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala
```

```
                755                 760                 765
Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu
            965

<210> SEQ ID NO 9
<211> LENGTH: 3114
<212> TYPE: DNA
<213> ORGANISM: Bifidobacterium bifidum

<400> SEQUENCE: 9
gttgaagatg caacaagaag cgatagcaca acacaaatgt catcaacacc ggaagttgtt     60
tattcatcag cggtcgatag caaacaaaat cgcacaagcg attttgatgc gaactggaaa    120
tttatgctgt cagatagcgt tcaagcacaa gatccggcat tgatgattc agcatggcaa     180 caagttgatc tgccgcatga ttatagcatc acacagaaat atagccaaag caatgaagca    240
gaatcagcat atcttccggg aggcacaggc tggtatagaa aaagctttac aattgataga    300
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aacaccgtc actggcaaca     600 caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
```

```
tttcgctgga caggctttga tgcaacatca ggcttttcac tgaatggcga aaaagtcaaa      960
ctgaaaggcg ttagcatgca tcatgatcaa ggctcacttg gcgcagttgc aaatagacgc     1020
gcaattgaaa gacaagtcga atcctgcaa aaaatgggcg tcaatagcat tcgcacaaca     1080
cataatccgg cagcaaaagc actgattgat gtctgcaatg aaaaaggcgt tctggttgtc     1140
gaagaagtct ttgatatgtg gaaccgcagc aaaaatggca cacggaaga ttatggcaaa      1200
tggtttggcc aagcaattgc aggcgataat gcagttctgg gaggcgataa agatgaaaca     1260
tgggcgaaat ttgatcttac atcaacaatt aaccgcgata gaaatgcacc gtcagttatt      1320
atgtggtcac tggcaatga aatgatgaa ggcatttcag gctcagtttc aggctttccg       1380
gcaacatcag caaaactggt tgcatggaca aaagcagcag attcaacaag accgatgaca     1440
tatggcgata acaaaattaa agcgaactgg aacgaatcaa atacaatggg cgataatctg     1500
acagcaaatg gcggagttgt tggcacaaat tattcagatg gcgcaaacta tgataaaatt     1560
cgtacaacac atccgtcatg ggcaatttat ggctcagaaa cagcatcagc gattaatagc     1620
cgtggcattt ataatagaac aacaggcgga gcacaatcat cagataaaca gctgacaagc     1680
tatgataatt cagcagttgg ctggggagca gttgcatcat cagcatggta tgatgttgtt     1740
cagagagatt ttgtcgcagg cacatatgtt tggacaggat ttgattatct gggcgaaccg     1800
acaccgtgga atggcacagg ctcaggcgca gttggctcat ggccgtcacc gaaaaatagc     1860
tattttggca tcgttgatac agcaggcttt ccgaaagata catattattt ttatcagagc     1920
cagtggaatg atgatgttca tacactgcat attcttccgg catggaatga aatgttgtt     1980
gcaaaaggct caggcaataa tgttccggtt gtcgtttata cagatgcagc gaaagtgaaa     2040
ctgtatttta caccgaaagg ctcaacagaa aaaagactga tcggcgaaaa atcatttaca     2100
aaaaaaacaa cagcggcagg ctatacatat caagtctatg aaggcagcga taagattca     2160
acagcgcata aaacatgta tctgacatgg aatgttccgt gggcagaagg cacaatttca     2220
gcggaagcgt atgatgaaaa taatcgcctg attccggaag gcagcacaga aggcaacgca     2280
tcagttacaa caacaggcaa agcagcaaaa ctgaaagcag atgcggatcg caaaacaatt     2340
acagcggatg gcaaagatct gtcatatatt gaagtcgatg tcacagatgc aaatggccat     2400
attgttccgg atgcagcaaa tagagtcaca tttgatgtta aaggcgcagg caaactggtt     2460
ggcgttgata tggctcatc accgatcat gattcatatc aagcggataa ccgcaaagca      2520
ttttcaggca agtcctggc aattgttcag tcaacaaaag aagcaggcga attacagtt      2580
acagcaaaag cagatggcct gcaatcaagc acagttaaaa ttgcaacaac agcagttccg     2640
ggaacaagca cagaaaaaac agtccgcagc ttttattaca gccgcaacta ttatgtcaaa     2700
acaggcaaca aaccgattct gccgtcagat gttgaagttc gctattcaga tggaacaagc     2760
gatagacaaa acgttacatg ggatgcagtt tcagatgatc aaattgcaaa agcaggctca     2820
ttttcagttg caggcacagt tgcaggccaa aaaattagcg ttcgcgtcac aatgattgat     2880
gaaattggcg cactgctgaa ttattcagca agcacaccgg ttggcacacc ggcagttctt     2940
ccgggatcaa gaccggcagt cctgccggat ggcacagtca catcagcaaa ttttgcagtc     3000
cattggacaa aaccggcaga tacagtctat aatacagcag gcacagtcaa agtaccggga     3060
acagcaacag tttttggcaa agaatttaaa gtcacagcga caattagagt tcaa           3114
```

<210> SEQ ID NO 10
<211> LENGTH: 1038
<212> TYPE: PRT
<213> ORGANISM: Bifidobacterium bifidum

<400> SEQUENCE: 10

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asp Val Thr Met
                195                 200                 205

Asn Leu Thr Thr Lys Val Ala Asn Asp Thr Glu Ala Ala Ala Asn Ile
            210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
```

-continued

```
                405                 410                 415
Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
            485                 490                 495

Gly Asp Asn Leu Thr Ala Asn Gly Gly Val Val Gly Thr Asn Tyr Ser
        500                 505                 510

Asp Gly Ala Asn Tyr Asp Lys Ile Arg Thr Thr His Pro Ser Trp Ala
    515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ser Ser Ala Trp
            565                 570                 575

Tyr Asp Val Val Gln Arg Asp Phe Val Ala Gly Thr Tyr Val Trp Thr
        580                 585                 590

Gly Phe Asp Tyr Leu Gly Glu Pro Thr Pro Trp Asn Gly Thr Gly Ser
    595                 600                 605

Gly Ala Val Gly Ser Trp Pro Ser Pro Lys Asn Ser Tyr Phe Gly Ile
610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
            645                 650                 655

Glu Asn Val Val Ala Lys Gly Ser Gly Asn Asn Val Pro Val Val Val
        660                 665                 670

Tyr Thr Asp Ala Ala Lys Val Lys Leu Tyr Phe Thr Pro Lys Gly Ser
    675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735

Gly Thr Ile Ser Ala Glu Ala Tyr Asp Glu Asn Asn Arg Leu Ile Pro
        740                 745                 750

Glu Gly Ser Thr Glu Gly Asn Ala Ser Val Thr Thr Thr Gly Lys Ala
    755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
        820                 825                 830
```

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
        850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

<210> SEQ ID NO 11
<211> LENGTH: 3426
<212> TYPE: DNA
<213> ORGANISM: Bifidobacterium bifidum

<400> SEQUENCE: 11
gttgaagatg caacaagaag cgatagcaca acacaaatgt catcaacacc ggaagttgtt    60
tattcatcag cggtcgatag caaacaaaat cgcacaagcg attttgatgc gaactggaaa   120
tttatgctgt cagatagcgt tcaagcacaa gatccggcat tgatgattc agcatggcaa    180 caagttgatc tgccgcatga ttatagcatc acacagaaat atagccaaag caatgaagca   240
gaatcagcat atcttccggg aggcacaggc tggtatagaa aaagctttac aattgataga   300
gatctggcag gcaaacgcat tgcgattaat tttgatggcg tctatatgaa tgcaacagtc   360
tggtttaatg gcgttaaact gggcacacat ccgtatggct attcaccgtt ttcatttgat   420
ctgacaggca atgcaaaatt tggcggagaa aacacaattg tcgtcaaagt tgaaaataga   480
ctgccgtcat caagatggta ttcaggcagc ggcatttata gagatgttac actgacagtt   540
acagatggcg ttcatgttgg caataatggc gtcgcaatta aaacaccgtc actggcaaca   600
caaaatggcg gagatgtcac aatgaacctg acaacaaaag tcgcgaatga tacagaagca   660
gcagcgaaca ttacactgaa acagacagtt tttccgaaag gcggaaaaac ggatgcagca   720
attggcacag ttacaacagc atcaaaatca attgcagcag gcgcatcagc agatgttaca   780
agcacaatta cagcagcaag cccgaaactg tggtcaatta aaacccgaa cctgtataca    840 gttagaacag aagttctgaa cggaggcaaa gttctggata catatgatac agaatatggc   900
tttcgctgga caggctttga tgcaacatca ggcttttcac tgaatggcga aaaagtcaaa   960

```
ctgaaaggcg ttagcatgca tcatgatcaa ggctcacttg gcgcagttgc aaatagacgc    1020
gcaattgaaa gacaagtcga aatcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat tgattatct gggcgaaccg     1800 acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcaccggt tggcacacc ggcagttctt      2940 ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
```

-continued

```
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatc                                                               3426
```

<210> SEQ ID NO 12
<211> LENGTH: 1142
<212> TYPE: PRT
<213> ORGANISM: Bifidobacterium bifidum

<400> SEQUENCE: 12

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350
```

```
Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
            450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala
            755                 760                 765
```

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr
      1010                1015                1020

Val Phe Gly Lys Glu Phe Lys Val Thr Ala Thr Ile Arg Val Gln
      1025                1030                1035

Arg Ser Gln Val Thr Ile Gly Ser Ser Val Ser Gly Asn Ala Leu
      1040                1045                1050

Arg Leu Thr Gln Asn Ile Pro Ala Asp Lys Gln Ser Asp Thr Leu
      1055                1060                1065

Asp Ala Ile Lys Asp Gly Ser Thr Thr Val Asp Ala Asn Thr Gly
      1070                1075                1080

Gly Gly Ala Asn Pro Ser Ala Trp Thr Asn Trp Ala Tyr Ser Lys
      1085                1090                1095

Ala Gly His Asn Thr Ala Glu Ile Thr Phe Glu Tyr Ala Thr Glu
      1100                1105                1110

Gln Gln Leu Gly Gln Ile Val Met Tyr Phe Phe Arg Asp Ser Asn
      1115                1120                1125

Ala Val Arg Phe Pro Asp Ala Gly Lys Thr Lys Ile Gln Ile
      1130                1135                1140

<210> SEQ ID NO 13
<211> LENGTH: 3633
<212> TYPE: DNA
<213> ORGANISM: Bifidobacterium bifidum

<400> SEQUENCE: 13

-continued

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaagtcaaa      960 ctgaaaggcg ttagcatgca tcatgatcaa ggctcacttg gcgcagttgc aaatagacgc    1020
gcaattgaaa gacaagtcga aatcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga tggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aatgttgtt     1980 gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taagattca     2160 acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
```

```
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt     2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg aca                                 3633
```

<210> SEQ ID NO 14
<211> LENGTH: 1211
<212> TYPE: PRT
<213> ORGANISM: Bifidobacterium bifidum

<400> SEQUENCE: 14

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140
```

-continued

```
Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
```

-continued

```
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
                595                 600                 605
Gly Ala Val Gly Ser Trp Ser Pro Lys Asn Ser Tyr Phe Gly Ile
610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val Val
                660                 665                 670
Tyr Thr Asp Ala Ala Lys Val Lys Leu Tyr Phe Thr Pro Lys Gly Ser
                675                 680                 685
Thr Glu Lys Arg Leu Ile Gly Glu Lys Ser Phe Thr Lys Lys Thr Thr
                690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
                725                 730                 735
Gly Thr Ile Ser Ala Glu Ala Tyr Asp Glu Asn Asn Arg Leu Ile Pro
                740                 745                 750
Glu Gly Ser Thr Glu Gly Asn Ala Ser Val Thr Thr Gly Lys Ala
                755                 760                 765
Ala Lys Leu Lys Ala Asp Ala Asp Arg Lys Thr Ile Thr Ala Asp Gly
                770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
                820                 825                 830
Tyr Gln Ala Asp Asn Arg Lys Ala Phe Ser Gly Lys Val Leu Ala Ile
                835                 840                 845
Val Gln Ser Thr Lys Glu Ala Gly Glu Ile Thr Val Thr Ala Lys Ala
                850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
                885                 890                 895
Tyr Tyr Val Lys Thr Gly Asn Lys Pro Ile Leu Pro Ser Asp Val Glu
                900                 905                 910
Val Arg Tyr Ser Asp Gly Thr Ser Asp Arg Gln Asn Val Thr Trp Asp
                915                 920                 925
Ala Val Ser Asp Asp Gln Ile Ala Lys Ala Gly Ser Phe Ser Val Ala
                930                 935                 940
Gly Thr Val Ala Gly Gln Lys Ile Ser Val Arg Val Thr Met Ile Asp
945                 950                 955                 960
Glu Ile Gly Ala Leu Leu Asn Tyr Ser Ala Ser Thr Pro Val Gly Thr
                965                 970                 975
Pro Ala Val Leu Pro Gly Ser Arg Pro Ala Val Leu Pro Asp Gly Thr
                980                 985                 990
```

Val Thr Ser Ala Asn Phe Ala Val His Trp Thr Lys Pro Ala Asp Thr
    995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr
    1205                1210

<210> SEQ ID NO 15
<211> LENGTH: 3888
<212> TYPE: DNA
<213> ORGANISM: Bifidobacterium bifidum

<400> SEQUENCE: 15
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat tgatgattc agcatggcaa      180 caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa acacaattg tcgtcaaagt tgaaaataga      480
ctgccgtcat caagatggta ttcaggcagc ggcatttata gagatgttac actgacagtt     540
acagatggcg ttcatgttgg caataatggc gtcgcaatta aacaccgtc actggcaaca      600 caaaatggcg gagatgtcac aatgaacctg acaacaaaag tcgcgaatga tacagaagca     660
gcagcgaaca ttcactgaa acagacagtt tttccgaaag cggaaaaaac ggatgcagca      720
attggcacag ttacaacagc atcaaaatca attgcagcag gcgcatcagc agatgttaca     780

```
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg cgcagttgc aaatagacgc    1020 gcaattgaaa gacaagtcga atcctgcaa aaaatgggcg tcaatagcat tcgcacaaca    1080
cataatccgg cagcaaaagc actgattgat gtctgcaatg aaaaggcgt tctggttgtc    1140 gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatgaa ggcatttcag gctcagtttc aggctttccg    1380
gcaacatcag caaaactggt tgcatggaca aaagcagcag attcaacaag accgatgaca    1440
tatggcgata caaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040 ctgtattta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccggaag cagcacaga aggcaacgca    2280 tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accgatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac agtccgcagc tttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag tttttggcaa agaatttaaa gtcacagcga caattagagt tcaaagaagc    3120
```

```
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg acaagcaaat ttgtcacaaa tacatcagca    3660
gcactgtcat cacttacagt caatggcaca aaagtttcag attcagttct ggcagcaggc    3720
tcatataaca caccggcaat tatcgcagat gttaaagcgg aaggcgaagg caatgcaagc    3780
gttacagtcc ttccggcaca tgataatgtt attcgcgtca ttacagaaag cgaagatcat    3840
gtcacacgca aacatttac aatcaacctg ggcacagaac aagaattt              3888
```

<210> SEQ ID NO 16  
<211> LENGTH: 1296  
<212> TYPE: PRT  
<213> ORGANISM: Bifidobacterium bifidum

<400> SEQUENCE: 16

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240
```

-continued

```
Ile Gly Thr Val Thr Thr Ala Ser Lys Ser Ile Ala Ala Gly Ala Ser
            245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
            275                 280                 285
Gly Lys Val Leu Asp Thr Tyr Asp Thr Glu Tyr Gly Phe Arg Trp Thr
            290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
                340                 345                 350
Gly Val Asn Ser Ile Arg Thr Thr His Asn Pro Ala Ala Lys Ala Leu
                355                 360                 365
Ile Asp Val Cys Asn Glu Lys Gly Val Leu Val Glu Glu Val Phe
            370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
                420                 425                 430
Asp Arg Asn Ala Pro Ser Val Ile Met Trp Ser Leu Gly Asn Glu Met
            435                 440                 445
Met Glu Gly Ile Ser Gly Ser Val Ser Gly Phe Pro Ala Thr Ser Ala
            450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
            500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
            530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
            610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val Val
```

-continued

Tyr Thr Asp Ala Ala Lys Val Lys Leu Tyr Phe Thr Pro Lys Gly Ser
          660                 665                 670
                675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
        930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val His Trp Thr Lys Pro Ala Asp Thr
                995                 1000                1005

Val Tyr Asn Thr Ala Gly Thr Val Lys Val Pro Gly Thr Ala Thr
        1010                1015                1020

Val Phe Gly Lys Glu Phe Lys Val Thr Ala Thr Ile Arg Val Gln
        1025                1030                1035

Arg Ser Gln Val Thr Ile Gly Ser Ser Val Ser Gly Asn Ala Leu
        1040                1045                1050

Arg Leu Thr Gln Asn Ile Pro Ala Asp Lys Gln Ser Asp Thr Leu
        1055                1060                1065

Asp Ala Ile Lys Asp Gly Ser Thr Thr Val Asp Ala Asn Thr Gly
        1070                1075                1080

```
Gly Gly Ala Asn Pro Ser Ala Trp Thr Asn Trp Ala Tyr Ser Lys
1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
        1115                1120                1125

Ala Val Arg Phe Pro Asp Ala Gly Lys Thr Lys Ile Gln Ile Ser
1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
        1160                1165                1170

Phe Ala Pro Val Gly Ala Thr Phe Val Lys Val Thr Val Thr Asn
1175                1180                1185

Ala Asp Thr Thr Thr Pro Ser Gly Val Val Cys Ala Gly Leu Thr
    1190                1195                1200

Glu Ile Glu Leu Lys Thr Ala Thr Ser Lys Phe Val Thr Asn Thr
        1205                1210                1215

Ser Ala Ala Leu Ser Ser Leu Thr Val Asn Gly Thr Lys Val Ser
1220                1225                1230

Asp Ser Val Leu Ala Ala Gly Ser Tyr Asn Thr Pro Ala Ile Ile
    1235                1240                1245

Ala Asp Val Lys Ala Glu Gly Glu Gly Asn Ala Ser Val Thr Val
        1250                1255                1260

Leu Pro Ala His Asp Asn Val Ile Arg Val Ile Thr Glu Ser Glu
1265                1270                1275

Asp His Val Thr Arg Lys Thr Phe Thr Ile Asn Leu Gly Thr Glu
    1280                1285                1290

Gln Glu Phe
    1295

<210> SEQ ID NO 17
<211> LENGTH: 1025
<212> TYPE: PRT
<213> ORGANISM: Kluyveromyces lactis

<400> SEQUENCE: 17

Met Ser Cys Leu Ile Pro Glu Asn Leu Arg Asn Pro Lys Lys Val His
1               5                   10                  15

Glu Asn Arg Leu Pro Thr Arg Ala Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
50                  55                  60

Ser Thr Ile Ser Val Pro Ser His Trp Glu Leu Gln Glu Asp Trp Lys
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
```

```
            130                 135                 140
Val Gly Phe Asn Lys Gly Ser Arg Asn Gly Ala Glu Phe Asp Ile Gln
145                 150                 155                 160

Lys Tyr Val Ser Glu Gly Asn Leu Val Val Lys Val Phe Lys
                    165                 170                 175

Trp Ser Asp Ser Thr Tyr Ile Glu Asp Gln Asp Gln Trp Trp Leu Ser
                180                 185                 190

Gly Ile Tyr Arg Asp Val Ser Leu Leu Lys Leu Pro Lys Lys Ala His
                195                 200                 205

Ile Glu Asp Val Arg Val Thr Thr Thr Phe Val Asp Ser Gln Tyr Gln
210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                    245                 250                 255

Asp Ala Ser Ser Leu Leu Asn Glu Glu Asn Gly Asn Thr Thr Phe Ser
                260                 265                 270

Thr Lys Glu Phe Ile Ser Phe Ser Thr Lys Lys Asn Glu Glu Thr Ala
                275                 280                 285

Phe Lys Ile Asn Val Lys Ala Pro Glu His Trp Thr Ala Glu Asn Pro
290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                    325                 330                 335

Asp Gly Asn Ile Thr Val Asn Gly Lys Asp Ile Leu Phe Arg Gly Val
                340                 345                 350

Asn Arg His Asp His His Pro Arg Phe Gly Arg Ala Val Pro Leu Asp
                355                 360                 365

Phe Val Val Arg Asp Leu Ile Leu Met Lys Lys Phe Asn Ile Asn Ala
370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                    405                 410                 415

Gly Val Gln Glu Pro Phe Asn Arg His Thr Asn Leu Glu Ala Glu Tyr
                420                 425                 430

Pro Asp Thr Lys Asn Lys Leu Tyr Asp Val Asn Ala His Tyr Leu Ser
                435                 440                 445

Asp Asn Pro Glu Tyr Glu Val Ala Tyr Leu Asp Arg Ala Ser Gln Leu
450                 455                 460

Val Leu Arg Asp Val Asn His Pro Ser Ile Ile Trp Ser Leu Gly
465                 470                 475                 480

Asn Glu Ala Cys Tyr Gly Arg Asn His Lys Ala Met Tyr Lys Leu Ile
                485                 490                 495

Lys Gln Leu Asp Pro Thr Arg Leu Val His Tyr Glu Gly Asp Leu Asn
                500                 505                 510

Ala Leu Ser Ala Asp Ile Phe Ser Phe Met Tyr Pro Thr Phe Glu Ile
                515                 520                 525

Met Glu Arg Trp Arg Lys Asn His Thr Asp Glu Asn Gly Lys Phe Glu
530                 535                 540

Lys Pro Leu Ile Leu Cys Glu Tyr Gly His Ala Met Gly Asn Gly Pro
545                 550                 555                 560
```

-continued

Gly Ser Leu Lys Glu Tyr Gln Glu Leu Phe Tyr Lys Glu Lys Phe Tyr
                565                 570                 575
Gln Gly Gly Phe Ile Trp Glu Trp Ala Asn His Gly Ile Glu Phe Glu
            580                 585                 590
Asp Val Ser Thr Ala Asp Gly Lys Leu His Lys Ala Tyr Ala Tyr Gly
        595                 600                 605
Gly Asp Phe Lys Glu Glu Val His Asp Gly Val Phe Ile Met Asp Gly
    610                 615                 620
Leu Cys Asn Ser Glu His Asn Pro Thr Pro Gly Leu Val Glu Tyr Lys
625                 630                 635                 640
Lys Val Ile Glu Pro Val His Ile Lys Ile Ala His Gly Ser Val Thr
                645                 650                 655
Ile Thr Asn Lys His Asp Phe Ile Thr Thr Asp His Leu Leu Phe Ile
            660                 665                 670
Asp Lys Asp Thr Gly Lys Thr Ile Asp Val Pro Ser Leu Lys Pro Glu
        675                 680                 685
Glu Ser Val Thr Ile Pro Ser Asp Thr Thr Tyr Val Val Ala Val Leu
    690                 695                 700
Lys Asp Asp Ala Gly Val Leu Lys Ala Gly His Glu Ile Ala Trp Gly
705                 710                 715                 720
Gln Ala Glu Leu Pro Leu Lys Val Pro Asp Phe Val Thr Glu Thr Ala
                725                 730                 735
Glu Lys Ala Ala Lys Ile Asn Asp Gly Lys Arg Tyr Val Ser Val Glu
            740                 745                 750
Ser Ser Gly Leu His Phe Ile Leu Asp Lys Leu Leu Gly Lys Ile Glu
        755                 760                 765
Ser Leu Lys Val Lys Gly Lys Glu Ile Ser Ser Lys Phe Glu Gly Ser
    770                 775                 780
Ser Ile Thr Phe Trp Arg Pro Pro Thr Asn Asn Asp Glu Pro Arg Asp
785                 790                 795                 800
Phe Lys Asn Trp Lys Lys Tyr Asn Ile Asp Leu Met Lys Gln Asn Ile
                805                 810                 815
His Gly Val Ser Val Glu Lys Gly Ser Asn Gly Ser Leu Ala Val Val
            820                 825                 830
Thr Val Asn Ser Arg Ile Ser Pro Val Val Phe Tyr Tyr Gly Phe Glu
        835                 840                 845
Thr Val Gln Lys Tyr Thr Ile Phe Ala Asn Lys Ile Asn Leu Asn Thr
    850                 855                 860
Ser Met Lys Leu Thr Gly Glu Tyr Gln Pro Pro Asp Phe Pro Arg Val
865                 870                 875                 880
Gly Tyr Glu Phe Trp Leu Gly Asp Ser Tyr Glu Ser Phe Glu Trp Leu
                885                 890                 895
Gly Arg Gly Pro Gly Glu Ser Tyr Pro Asp Lys Lys Glu Ser Gln Arg
            900                 905                 910
Phe Gly Leu Tyr Asp Ser Lys Asp Val Glu Glu Phe Val Tyr Asp Tyr
        915                 920                 925
Pro Gln Glu Asn Gly Asn His Thr Asp Thr His Phe Leu Asn Ile Lys
    930                 935                 940
Phe Glu Gly Ala Gly Lys Leu Ser Ile Phe Gln Lys Glu Lys Pro Phe
945                 950                 955                 960
Asn Phe Lys Ile Ser Asp Glu Tyr Gly Val Asp Glu Ala Ala His Ala
                965                 970                 975

```
Cys Asp Val Lys Arg Tyr Gly Arg His Tyr Leu Arg Leu Asp His Ala
            980                 985                 990

Ile His Gly Val Gly Ser Glu Ala Cys Gly Pro Ala Val Leu Asp Gln
            995                 1000                1005

Tyr Arg Leu Lys Ala Gln Asp Phe Asn Phe Glu Phe Asp Leu Ala
    1010                1015                1020

Phe Glu
    1025

<210> SEQ ID NO 18
<211> LENGTH: 902
<212> TYPE: PRT
<213> ORGANISM: Aspergillus oryzae

<400> SEQUENCE: 18

Ser Ile Lys His Arg Leu Asn Gly Phe Thr Ile Leu Glu His Pro Asp
1               5                   10                  15

Pro Ala Lys Arg Asp Leu Leu Gln Asp Ile Val Thr Trp Asp Asp Lys
            20                  25                  30

Ser Leu Phe Ile Asn Gly Glu Arg Ile Met Leu Phe Ser Gly Glu Val
            35                  40                  45

His Pro Phe Arg Leu Pro Val Pro Ser Leu Trp Leu Asp Ile Phe His
        50                  55                  60

Lys Ile Arg Ala Leu Gly Phe Asn Cys Val Ser Phe Tyr Ile Asp Trp
65                  70                  75                  80

Ala Leu Leu Glu Gly Lys Pro Gly Asp Tyr Arg Ala Glu Gly Ile Phe
                85                  90                  95

Ala Leu Glu Pro Phe Phe Asp Ala Ala Lys Glu Ala Gly Ile Tyr Leu
            100                 105                 110

Ile Ala Arg Pro Gly Ser Tyr Ile Asn Ala Glu Val Ser Gly Gly Gly
            115                 120                 125

Phe Pro Gly Trp Leu Gln Arg Val Asn Gly Thr Leu Arg Ser Ser Asp
        130                 135                 140

Glu Pro Phe Leu Lys Ala Thr Asp Asn Tyr Ile Ala Asn Ala Ala Ala
145                 150                 155                 160

Ala Val Ala Lys Ala Gln Ile Thr Asn Gly Gly Pro Val Ile Leu Tyr
                165                 170                 175

Gln Pro Glu Asn Glu Tyr Ser Gly Gly Cys Cys Gly Val Lys Tyr Thr
            180                 185                 190

Asp Ala Asp Tyr Met Gln Tyr Val Met Asp Gln Ala Arg Lys Ala Asp
            195                 200                 205

Ile Val Val Pro Phe Ile Ser Asn Asp Ala Ser Pro Ser Gly His Asn
        210                 215                 220

Ala Pro Gly Ser Gly Thr Gly Ala Val Asp Ile Tyr Gly His Asp Ser
225                 230                 235                 240

Tyr Pro Leu Gly Phe Asp Cys Ala Asn Pro Ser Val Trp Pro Glu Gly
                245                 250                 255

Lys Leu Pro Asp Asn Phe Arg Thr Leu His Leu Glu Gln Ser Pro Ser
            260                 265                 270

Thr Pro Tyr Ser Leu Leu Glu Phe Gln Ala Gly Ala Phe Asp Pro Trp
            275                 280                 285

Gly Gly Pro Gly Phe Glu Lys Cys Tyr Ala Leu Val Asn His Glu Phe
        290                 295                 300

Ser Arg Val Phe Tyr Arg Asn Asp Leu Ser Phe Gly Val Ser Thr Phe
305                 310                 315                 320
```

```
Asn Leu Tyr Met Thr Phe Gly Thr Asn Trp Gly Asn Leu Gly His
                325             330             335

Pro Gly Gly Tyr Thr Ser Tyr Asp Tyr Gly Ser Pro Ile Thr Glu Thr
            340             345             350

Arg Asn Val Thr Arg Glu Lys Tyr Ser Asp Ile Lys Leu Leu Ala Asn
                355             360             365

Phe Val Lys Ala Ser Pro Ser Tyr Leu Thr Ala Thr Pro Arg Asn Leu
            370             375             380

Thr Thr Gly Val Tyr Thr Asp Thr Ser Asp Leu Ala Val Thr Pro Leu
385             390             395             400

Ile Gly Asp Ser Pro Gly Ser Phe Phe Val Val Arg His Thr Asp Tyr
                405             410             415

Ser Ser Gln Glu Ser Thr Ser Tyr Lys Leu Lys Leu Pro Thr Ser Ala
            420             425             430

Gly Asn Leu Thr Ile Pro Gln Leu Glu Gly Thr Leu Ser Leu Asn Gly
                435             440             445

Arg Asp Ser Lys Ile His Val Val Asp Tyr Asn Val Ser Gly Thr Asn
450             455             460

Ile Ile Tyr Ser Thr Ala Glu Val Phe Thr Trp Lys Lys Phe Asp Gly
465             470             475             480

Asn Lys Val Leu Val Leu Tyr Gly Gly Pro Lys Glu His His Glu Leu
                485             490             495

Ala Ile Ala Ser Lys Ser Asn Val Thr Ile Ile Glu Gly Ser Asp Ser
            500             505             510

Gly Ile Val Ser Thr Arg Lys Gly Ser Ser Val Ile Gly Trp Asp
                515             520             525

Val Ser Ser Thr Arg Arg Ile Val Gln Val Gly Asp Leu Arg Val Phe
530             535             540

Leu Leu Asp Arg Asn Ser Ala Tyr Asn Tyr Trp Val Pro Glu Leu Pro
545             550             555             560

Thr Glu Gly Thr Ser Pro Gly Phe Ser Thr Ser Lys Thr Thr Ala Ser
            565             570             575

Ser Ile Ile Val Lys Ala Gly Tyr Leu Leu Arg Gly Ala His Leu Asp
            580             585             590

Gly Ala Asp Leu His Leu Thr Ala Asp Phe Asn Ala Thr Thr Pro Ile
            595             600             605

Glu Val Ile Gly Ala Pro Thr Gly Ala Lys Asn Leu Phe Val Asn Gly
            610             615             620

Glu Lys Ala Ser His Thr Val Asp Lys Asn Gly Ile Trp Ser Ser Glu
625             630             635             640

Val Lys Tyr Ala Ala Pro Glu Ile Lys Leu Pro Gly Leu Lys Asp Leu
            645             650             655

Asp Trp Lys Tyr Leu Asp Thr Leu Pro Glu Ile Lys Ser Ser Tyr Asp
            660             665             670

Asp Ser Ala Trp Val Ser Ala Asp Leu Pro Lys Thr Lys Asn Thr His
            675             680             685

Arg Pro Leu Asp Thr Pro Thr Ser Leu Tyr Ser Ser Asp Tyr Gly Phe
            690             695             700

His Thr Gly Tyr Leu Ile Tyr Arg Gly His Phe Val Ala Asn Gly Lys
705             710             715             720

Glu Ser Glu Phe Phe Ile Arg Thr Gln Gly Gly Ser Ala Phe Gly Ser
                725             730             735
```

```
Ser Val Trp Leu Asn Glu Thr Tyr Leu Gly Ser Trp Thr Gly Ala Asp
            740                 745                 750

Tyr Ala Met Asp Gly Asn Ser Thr Tyr Lys Leu Ser Gln Leu Glu Ser
        755                 760                 765

Gly Lys Asn Tyr Val Ile Thr Val Ile Asp Asn Leu Gly Leu Asp
    770                 775                 780

Glu Asn Trp Thr Val Gly Glu Glu Thr Met Lys Asn Pro Arg Gly Ile
785                 790                 795                 800

Leu Ser Tyr Lys Leu Ser Gly Gln Asp Ala Ser Ala Ile Thr Trp Lys
                805                 810                 815

Leu Thr Gly Asn Leu Gly Gly Gly Asp Tyr Gln Asp Lys Val Arg Gly
            820                 825                 830

Pro Leu Asn Glu Gly Gly Leu Tyr Ala Glu Arg Gln Gly Phe His Gln
            835                 840                 845

Pro Gln Pro Pro Ser Glu Ser Trp Glu Ser Gly Ser Pro Leu Glu Gly
            850                 855                 860

Leu Ser Lys Pro Gly Ile Gly Phe Tyr Thr Ala Gln Phe Asp Leu Asp
865                 870                 875                 880

Leu Pro Lys Gly Trp Asp Val Pro Leu Tyr Phe Asn Phe Gly Asn Asn
                885                 890                 895

Thr Gln Ala Ala Arg Ala
            900

<210> SEQ ID NO 19
<211> LENGTH: 24
<212> TYPE: DNA
<213> ORGANISM: Artificial Sequence
<220> FEATURE:
<223> OTHER INFORMATION: I-SceI-1 oligo

<400> SEQUENCE: 19
cgattaggga taacagggta atat                                          24

<210> SEQ ID NO 20
<211> LENGTH: 24
<212> TYPE: DNA
<213> ORGANISM: Artificial Sequence
<220> FEATURE:
<223> OTHER INFORMATION: I-SceI-2 olio

<400> SEQUENCE: 20
cgatattacc ctgttatccc taat                                          24

<210> SEQ ID NO 21
<211> LENGTH: 32
<212> TYPE: DNA
<213> ORGANISM: Artificial Sequence
<220> FEATURE:
<223> OTHER INFORMATION: primer 981

<400> SEQUENCE: 21
aaccagcact agtgtcgacg cctggtaggt cg                                 32

<210> SEQ ID NO 22
<211> LENGTH: 54
<212> TYPE: DNA
<213> ORGANISM: Artificial Sequence
<220> FEATURE:
<223> OTHER INFORMATION: primer 984

<400> SEQUENCE: 22
```
gcaccaatgt atcctgtttt ccccatatcg ttagcccttt aaccgatcat catc         54

<210> SEQ ID NO 23
<211> LENGTH: 37
<212> TYPE: DNA
<213> ORGANISM: Artificial Sequence
<220> FEATURE:
<223> OTHER INFORMATION: primer 985

<400> SEQUENCE: 23
atatggatcc gttctactag acatttatga agtacag                            37

<210> SEQ ID NO 24
<211> LENGTH: 42
<212> TYPE: DNA
<213> ORGANISM: Artificial Sequence
<220> FEATURE:
<223> OTHER INFORMATION: primer 983

<400> SEQUENCE: 24
gatgatgatc ggttaaaggg ctaacgatat ggggaaaaca gg                      42

<210> SEQ ID NO 25
<211> LENGTH: 3027
<212> TYPE: DNA
<213> ORGANISM: Lactobacillus delbrueckii

<400> SEQUENCE: 25
atgagcaata agttagtaaa agaaaaaaga gttgaccagg cagacctggc ctggctgact    60
gacccggaag tttacgaagt caatacaatt cccccgcact ccgaccatga gtccttccaa   120
agccaggaag aactggagga gggcaagtcc agtttagtgc agtccctgga cggggactgg   180
ctgattgact acgctgaaaa cggccaggga ccagtcaact tctatgcaga agactttgac   240
gatagcaatt ttaagtcagt caaagtaccc ggcaacctgg aactgcaagg ctttggccag   300
ccccagtatg tcaacgtcca atatccatgg acggcagtg aggagatttt cccgccccaa   360
attccaagca aaaatccgct cgcttcttat gtcagatact ttgacctgga tgaagctttc   420
tgggacaagg aagtcagctt gaagtttgac ggggcggcaa cagccatcta tgtctggctg   480
aacggccact cgtcggcta cggggaagac tcctttaccc caagtgagtt tatggttacc   540
aagttcctca gaaagaaaa taaccgcctg gcagtggctc tctacaagta ttcttccgcc   600
tcctggctgg aagaccagga cttctggcgc atgtctggtt tgttcagatc agtgactctt   660
caggccaagc cgcgtctgca cttggaggac cttaagctta cggccagctt gaccgataac   720
taccaaaaag gaaagctgga agtcgaagcc aatattgcct accgcttgcc aaatgccagc   780
tttaagctgg aagtgcggga tagtgaaggt gacttggttg ctgaaaagct gggcccaatc   840
agaagcgagc agctggaatt cactctggct gatttgccag tagctgcctg gagcgcggaa   900
aagcctaacc tttaccaggt ccgcctgtat ttataccagg caggcagcct cttagaggtt   960
agccggcagg aagtggggttt ccgcaacttt gaactaaaag acgggattat gtaccttaac  1020
ggccagcgga tcgtcttcaa gggggccaac cggcacgaat tgacagtaa gttgggtcgg   1080 gctatcacgg aagaggatat gatctggac atcaagacca tgaagcgaag caacatcaat  1140
gctgtccgct gctctcacta cccgaaccag tccctctttt accggctctg tgacaagtac  1200
ggcctttacg tcattgatga agctaacctg gaaagccacg gcacctggga aaaagtgggg  1260
gggcacgaag atcctagctt caatgttcca ggcgatgacc agcattggct gggagccagc  1320
ttatcccggg tgaagaacat gatggctcgg gacaagaacc atgcttcaat cctaatctgg  1380

```
tctttaggca atgagtctta cgccggcact gtctttgccc aaatggctga ttacgtccgg    1440
aaggctgatc cgacccgggt tcagcactat gaagggtga cccataaccg aagtttgac     1500 gacgccaccc agattgaaag ccggatgtat gctccggcca aggtaattga agaatacttg    1560
accaataaac cagccaagcc atttatctca gttgaatacg ctcacgccat ggcaactcc     1620 gtcggtgacc tggccgccta cacggccctg aaaaatacc cccactacca gggcggcttc     1680
atctgggact ggattgacca aggactggaa aaagacgggc acctgcttta tggggcgac    1740 ttcgatgacc ggccaaccga ctatgaattc tgcgggaacg gcctggtctt tgctgaccgg    1800
actgaatcgc cgaaactggc taatgtcaag gccctttacg ccaaccttaa gttagaagta   1860
aaagatgggc agctcttcct caaaaacgac aatttattta ccaacagctc atcttactac    1920
ttcttgacta gtcttttggt cgatggcaag ttgacctacc agagccggcc tctgacccttt  1980 ggcctggagc ctggcgaatc cgggaccttt gccctgcctt ggccggaagt cgctgatgaa    2040
aaaggagagg tcgtctaccg ggtaacggcc cacttaaaag aagacttgcc ttgggcggat    2100
gagggcttca ctgtggctga agcagaagaa gtagctcaaa agctgccgga atttaagccg    2160
gaagggcggc cagatttagt tgattccgac tacaacctag gcctgaaagg aaataacttc    2220
caaattctct tctccaaggt caagggctgg ccggtttccc tcaagtatgc cggtagggaa    2280
tacttgaagc ggctgccgga atttaccttc tggcgggccc tgacggacaa cgaccgggga    2340
gctggttacg gctatgatct ggcccggtgg gaaaatgccg gcaagtatgc ccgcttgaaa    2400
gacatcagct gcgaggtcaa ggaagactcc gttttggtca agactgcctt tacgttgcct    2460
gtcgccttaa agggtgattt aaccgtgacc tatgaagtcg atggacgggg caagattgct    2520
gtaacagctg acttcccagg cgcggaagaa gccggtctct tgccagcctt tggcttgaac    2580
ctggccctgc caaaagaact gaccgattac cgctactatg gtctgggacc taatgagagc    2640
tacccagacc gcttggaagg taattacctg ggcatctacc agggagcggt aaaaaagaac    2700
tttagcccat acctgcgtcc gcaggaaacg ggcaaccgga gcaaggttcg ctggtaccag    2760
ctctttgatg aaaagggcgg cttggaattt acggccaatg gggcagactt gaacttgtct    2820
gctttgccat attctgccgc ccaaattgaa gcagcggacc acgcttttga actgactaac    2880
aattacactt gggttagagc cttaagcgcc cagatggggg tcggcgggga tgactcctgg    2940
gggcagaagg tccacccgga attctgcctg gatgctcaaa aagcccgcca gctccgcctg    3000
gtgattcagc ccctttttact aaaataa                                      3027
```

<210> SEQ ID NO 26
<211> LENGTH: 1008
<212> TYPE: PRT
<213> ORGANISM: Lactobacillus delbrueckii

<400> SEQUENCE: 26

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

-continued

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
                100                 105                 110

Ser Glu Glu Ile Phe Pro Pro Gln Ile Pro Ser Lys Asn Pro Leu Ala
                115                 120                 125

Ser Tyr Val Arg Tyr Phe Asp Leu Asp Glu Ala Phe Trp Asp Lys Glu
                130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
                180                 185                 190

Ala Leu Tyr Lys Tyr Ser Ser Ala Ser Trp Leu Glu Asp Gln Asp Phe
                195                 200                 205

Trp Arg Met Ser Gly Leu Phe Arg Ser Val Thr Leu Gln Ala Lys Pro
        210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Arg Ser Gln Leu Glu Phe Thr
                275                 280                 285

Leu Ala Asp Leu Pro Val Ala Ala Trp Ser Ala Glu Lys Pro Asn Leu
        290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
                340                 345                 350

Glu Phe Asp Ser Lys Leu Gly Arg Ala Ile Thr Glu Glu Asp Met Ile
        355                 360                 365

Trp Asp Ile Lys Thr Met Lys Arg Ser Asn Ile Asn Ala Val Arg Cys
        370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
                420                 425                 430

Asp Gln His Trp Leu Gly Ala Ser Leu Ser Arg Val Lys Asn Met Met
        435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

-continued

Arg Lys Phe Asp Asp Ala Thr Gln Ile Glu Ser Arg Met Tyr Ala Pro
            500                 505                 510
Ala Lys Val Ile Glu Glu Tyr Leu Thr Asn Lys Pro Ala Lys Pro Phe
        515                 520                 525
Ile Ser Val Glu Tyr Ala His Ala Met Gly Asn Ser Val Gly Asp Leu
    530                 535                 540
Ala Ala Tyr Thr Ala Leu Glu Lys Tyr Pro His Tyr Gln Gly Gly Phe
545                 550                 555                 560
Ile Trp Asp Trp Ile Asp Gln Gly Leu Glu Lys Asp Gly His Leu Leu
                565                 570                 575
Tyr Gly Gly Asp Phe Asp Asp Arg Pro Thr Asp Tyr Glu Phe Cys Gly
            580                 585                 590
Asn Gly Leu Val Phe Ala Asp Arg Thr Glu Ser Pro Lys Leu Ala Asn
        595                 600                 605
Val Lys Ala Leu Tyr Ala Asn Leu Lys Leu Glu Val Lys Asp Gly Gln
    610                 615                 620
Leu Phe Leu Lys Asn Asp Asn Leu Phe Thr Asn Ser Ser Ser Tyr Tyr
625                 630                 635                 640
Phe Leu Thr Ser Leu Leu Val Asp Gly Lys Leu Thr Tyr Gln Ser Arg
                645                 650                 655
Pro Leu Thr Phe Gly Leu Glu Pro Gly Glu Ser Gly Thr Phe Ala Leu
            660                 665                 670
Pro Trp Pro Glu Val Ala Asp Glu Lys Gly Glu Val Val Tyr Arg Val
        675                 680                 685
Thr Ala His Leu Lys Glu Asp Leu Pro Trp Ala Asp Glu Gly Phe Thr
    690                 695                 700
Val Ala Glu Ala Glu Glu Val Ala Gln Lys Leu Pro Glu Phe Lys Pro
705                 710                 715                 720
Glu Gly Arg Pro Asp Leu Val Asp Ser Asp Tyr Asn Leu Gly Leu Lys
                725                 730                 735
Gly Asn Asn Phe Gln Ile Leu Phe Ser Lys Val Lys Gly Trp Pro Val
            740                 745                 750
Ser Leu Lys Tyr Ala Gly Arg Glu Tyr Leu Lys Arg Leu Pro Glu Phe
        755                 760                 765
Thr Phe Trp Arg Ala Leu Thr Asp Asn Asp Arg Gly Ala Gly Tyr Gly
    770                 775                 780
Tyr Asp Leu Ala Arg Trp Glu Asn Ala Gly Lys Tyr Ala Arg Leu Lys
785                 790                 795                 800
Asp Ile Ser Cys Glu Val Lys Glu Asp Ser Val Leu Val Lys Thr Ala
                805                 810                 815
Phe Thr Leu Pro Val Ala Leu Lys Gly Asp Leu Thr Val Thr Tyr Glu
            820                 825                 830
Val Asp Gly Arg Gly Lys Ile Ala Val Thr Ala Asp Phe Pro Gly Ala
        835                 840                 845
Glu Glu Ala Gly Leu Leu Pro Ala Phe Gly Leu Asn Leu Ala Leu Pro
    850                 855                 860
Lys Glu Leu Thr Asp Tyr Arg Tyr Tyr Gly Leu Gly Pro Asn Glu Ser
865                 870                 875                 880
Tyr Pro Asp Arg Leu Glu Gly Asn Tyr Leu Gly Ile Tyr Gln Gly Ala
                885                 890                 895
Val Lys Lys Asn Phe Ser Pro Tyr Leu Arg Pro Gln Glu Thr Gly Asn
            900                 905                 910
Arg Ser Lys Val Arg Trp Tyr Gln Leu Phe Asp Glu Lys Gly Gly Leu

-continued

```
            915                 920                 925
Glu Phe Thr Ala Asn Gly Ala Asp Leu Asn Leu Ser Ala Leu Pro Tyr
    930                 935                 940

Ser Ala Ala Gln Ile Glu Ala Ala Asp His Ala Phe Glu Leu Thr Asn
945                 950                 955                 960

Asn Tyr Thr Trp Val Arg Ala Leu Ser Ala Gln Met Gly Val Gly Gly
                965                 970                 975

Asp Asp Ser Trp Gly Gln Lys Val His Pro Glu Phe Cys Leu Asp Ala
                980                 985                 990

Gln Lys Ala Arg Gln Leu Arg Leu  Val Ile Gln Pro Leu  Leu Leu Lys
            995                 1000                1005
```

BACILLUS HOST CELLS PRODUCING β-GALACTOSIDASES AND LACTASES IN THE ABSENCE OF P-NITROBENZYLESTERASE SIDE ACTIVITY

CROSS-REFERENCE TO RELATED APPLICATIONS

This application claims priority to U.S. Provisional Patent Application No. 62/483,239, filed Apr. 7, 2017, the disclosure of which is herein incorporated by reference in their entirety.

FIELD

The present disclosure is generally related to the fields of bacteriology, microbiology, genetics, molecular biology, enzymology, probiotics, dairy food products and the like. Certain embodiments of the disclosure are directed to genetically modified *Bacillus* host cells expressing/producing β-galactosidase and/or lactase enzymes, and the use of such enzymes for the production of galactooligosaccharide (GOS) compositions in one or more dairy related end products. More particularly, certain embodiments are directed to expressing/producing such β-galactosidase and/or lactase enzymes in modified *Bacillus* host cells, wherein such enzymes produced and purified from the modified *Bacillus* host cells are free of unwanted/undesirable enzymatic side activities including, but not limited to, unwanted/undesirable lipase side activities, phospholipase side activities, cellulase side activities, pectinase side activities, amylase side activities, protease side activities, mannanase side activities and the like.

REFERENCE TO A SEQUENCE LISTING

The contents of the electronic submission of the text file Sequence Listing, named "NB41138-WO-PCT_Sequence-Listing.txt", was created on Apr. 2, 2018 and is 139 KB in size, which is hereby incorporated by reference in its entirety.

BACKGROUND

The use of enzymes to enhance and/or improve the chemical nature of food products is widely used and accepted in the art. In particular, the processing of cow's milk and other animal derived substrates adds significant value to these dairy related end-products. For example, galactooligosaccharides (GOSs) are carbohydrates which are non-digestible in humans (and animals), comprising two or more galactose molecules (typically up to nine) linked by glycosidic bonds. A particularly beneficial effect of such galactooligosaccharides is their ability to act as pre-biotic compounds, by selectively stimulating the proliferation of beneficial (colonic) microorganisms (e.g., bacteria) that provide physiological benefits to the consumer of such GOS compositions. Thus, the established health benefits of such GOS compositions have resulted in a growing interest of galactooligosaccharides as ingredients for various types of food.

The enzyme β-galactosidase (EC 3.2.1.23) generally hydrolyzes lactose to the monosaccharides D-glucose and D-galactose. In the enzymatic reaction of β-galactosidases, the enzyme hydrolyzes lactose and transiently binds the galactose monosaccharide in a galactose-enzyme complex. Subsequently, water is used to hydrolyze the covalent galactose-enzyme intermediate, thereby resulting in the liberation of D-galactose and D-glucose. However, at high lactose concentrations, some β-galactosidases are able to transfer galactose to the hydroxyl groups of D-galactose or D-glucose, in a process called transgalactosylation, wherein galactooligosaccharides (GOSs) are thereby produced. Thus, at high lactose concentrations, most β-galactosidases are able to transfer galactose to the hydroxyl groups of lactose and/or higher order oligosaccharides.

The genus *Bifidobacterium* is commonly used in the dairy industry, wherein the ingestion of *Bifidobacterium*-containing products furthermore has a health-promoting effect. This effect is not only achieved by a lowered pH of the intestinal contents, but also by the ability of *Bifidobacterium* to repopulate the intestinal flora in individuals who have had their intestinal flora disturbed (e.g., via the intake of antibiotics). *Bifidobacterium* furthermore has the potential of outcompeting potentially harmful intestinal microorganisms.

Thus, as briefly stated above, galactooligosaccharides (GOSs) are known to enhance the growth of beneficial microorganisms such as *Bifidobacterium*. This effect is likely achieved through the unique ability of *Bifidobacterium* to exploit galactooligosaccharides as a carbon source. For example, dietary supplements of galactooligosaccharides are thought to have a number of long-term disease protecting effects. Thus, there is a high level of interest in the art for developing inexpensive and efficient methods for producing galactooligosaccharides for use in the industry for improving dietary supplements and dairy products.

For example, an extracellular lactase from *Bifidobacterium bifidum* DSM20215, truncated with approximately 580 amino acids (BIF3-d3) has been described as a transgalactosylating enzyme in solutions containing lactose solubilized in water (Jorgensen et al., 2001). International PCT Publication No. WO2001/90317 describes a truncation variant (OLGA347) as being a transgalactosylating enzyme, and International PCT Publication No. WO2012/010597 shows that the truncation variant OLGA347 transfers a galactose moiety to D-fucose, N-acetyl-galactosamine and xylose. U.S. Patent Publication No. US2012/0040051 describes a process for preparing easily absorbable milk products with high galactooligosaccharide (GOS) content and low lactose content, and a galactooligosaccharide-enhanced milk product prepared with the process using for example lactases from any origin, including, lactases from *Aspergillus, Saccharomyces* and *Kluyveromyces*. Galactooligosaccharide (GOS) synthesis from a lactose solution or skim milk, using a β-galactosidase from *Baccilus circulars*, is described by Rodriguez-Colinas et al. (2012). International PCT Publication No. WO2008/037839 discloses a process for producing products containing galactooligosaccharides by treating a milk-based raw material after addition of fructose, and optionally lactose, with a β-galactosidase and terminating the enzymatic reaction of the reaction mixture. European Patent Application No. EP0458358 discloses a skim milk powder containing galactooligosaccharide (GOS) and a process for producing the same, wherein the process comprises adding β-galactosidase to concentrated milk to give rise to an enzymatic reaction and heating the reaction mixture to 75-80° C. to terminate the enzymatic reaction, followed by spray drying of the reaction mixture.

Thus, as generally disclosed above, there is a high level of interest and ongoing research in the use of such β-galactosidases, lactases and transgalactosylating enzymes thereof for the production of galactooligosaccharides (GOS) in dairy related foods products (e.g., milk, yoghurt and the like). For example, International PCT Publication No. WO2015/086746 describes six (6) *Bifidobacterium bifidum* β-galactosidase truncation variants (derived from a full length *B. bifidum* β-galactosidase), which are expressed and produced in *Bacillus* host cells (which are known to be capable of high levels of heterologous protein production).

However, dairy related food products and applications thereof are highly sensitive towards numerous "non-target" (i.e., unwanted/undesirable) enzyme activities, which are also referred to in the art as "enzyme side activity" or "enzymatic side activity". For example, small amounts of cellulase, pectinase, amylase, protease, mannanase and the like enzymatic activities are undesirable in most dairy related products (i.e., unwanted/undesirable enzymatic side activities), as many dairy products are formulated/stabilized with hydrocolloids such as carboxymethyl cellulose (CMC), guar (GUAR gum), starch, carrageenan, pectin and the like. In addition, other (unwanted/undesirable) enzymatic side activities to be mentioned are protease, lipase and phospholipase activities, which can produce a foul off-flavor or smell in the end product. Furthermore, these (unwanted/undesirable) enzymatic side activities often originate as byproducts from the production host cell during fermentation. It is therefore highly critical to identify such unwanted/undesirable enzymatic side activities early in the GOS/dairy product development cycle, in order to assess the severity that these unwanted enzymatic side activities impart on the end-product.

Thus, as set forth below in the Detailed Description, the present disclosure addresses an ongoing need in the art for efficiently and inexpensively producing high quantities of β-galactosidases and lactases in microbial host cells, wherein such β-galactosidases and lactases produced therefrom are added to dairy products for the production of galactooligosaccharide (GOS) compositions therein. More particularly, the instant disclosure addresses the ongoing and unmet need for efficiently and inexpensively producing high quantities of β-galactosidases and lactases in *Bacillus* spp. host cells, wherein such enzymes produced and purified from the *Bacillus* spp. host cells are free of unwanted/undesirable enzymatic side activities including, but not limited to, lipase side activities, phospholipase side activities, cellulase side activities, pectinase side activities, amylase side activities, protease side activities, mannanase side activities and the like.

SUMMARY

The present disclosure is generally related to genetically modified *Bacillus* host cells expressing/producing β-galactosidase and/or lactase enzymes, and the use of such enzymes for the production of galactooligosaccharide (GOS) compositions in one or more dairy related end products. Thus, certain embodiments of the disclosure are directed to expressing/producing such β-galactosidase and/or lactase enzymes in modified *Bacillus* host cells, wherein such enzymes produced and purified from the modified *Bacillus* host cells are free of unwanted/undesirable enzymatic side activities including, but not limited to, unwanted/undesirable lipase side activities, phospholipase side activities, cellulase side activities, pectinase side activities, amylase side activities, protease side activities, mannanase side activities and the like.

More particularly, certain embodiments of the disclosure are related to *Bacillus* (host) cells expressing a polypeptide comprising β-galactosidase activity or transgalactosylating activity, wherein the host cell comprises a genetic modification which reduces or eliminates para-nitrobenzylesterase (p-NBE) activity. In certain embodiments, a genetic modification (i.e., which reduces or eliminates p-NBE activity in the modified cell) comprises a deletion, disruption or down-regulation of a gene encoding a p-NBE polypeptide comprising at least 60% sequence identity to the p-NBE polypeptide of SEQ ID NO: 2. In certain embodiments, a genetic modification comprises a complete or partial deletion of a gene encoding a p-NBE polypeptide comprising at least 60% sequence identity to the p-NBE polypeptide of SEQ ID NO: 2. In certain other embodiments, a partial deletion comprises deleting one or more codons encoding the p-NBE active site amino acids $Ser_{189}$, $Glu_{m}$) and/or $His_{399}$. In other embodiments, a partial deletion comprises a nucleotide frameshift deletion in the gene encoding the p-NBE, wherein the frameshift deletion results in an encoded protein thereof lacking p-NBE activity. In another embodiment, a partial deletion of a gene encoding a p-NBE polypeptide comprises deleting nucleotides of the p-NBE gene encoding amino acid residues 1-163 of SEQ ID NO: 2, deleting nucleotides of the p-NBE gene encoding amino acid residues 164-326 of SEQ ID NO: 2, deleting nucleotides of the p-NBE gene encoding amino acid residues 327-489 of SEQ ID NO: 2 or a combination thereof. In certain other embodiments, a partial deletion of a gene encoding a p-NBE polypeptide comprises deleting the acetyl esterase (AE) domain encoded by the p-NBE gene. In certain other embodiments, the AE domain is comprised within amino acid residues 85-211 of SEQ ID NO: 2. In another embodiment, the AE domain is comprised within amino acid residues 85-211 of a polypeptide comprising at least 60% sequence identity to SEQ ID NO: 2. In yet other embodiments, a partial deletion of a gene encoding a p-NBE polypeptide comprises deleting one or more codons of the gene which encode the p-NBE substrate binding pocket.

In other embodiments, the genetic modification (i.e., which reduces or eliminates p-NBE activity in the modified cell) comprises a disruption of a gene encoding a p-NBE polypeptide comprising at least 60% sequence identity to the p-NBE polypeptide of SEQ ID NO: 2. In certain embodiments, a p-NBE gene disruption comprises the insertion of a selectable marker into the p-NBE gene, thereby disrupting the p-NBE gene coding sequence. In certain embodiments, a gene encoding a p-NBE polypeptide comprising at least 60% sequence identity to SEQ ID NO: 2 is disrupted by insertion of a selectable marker. In certain embodiments, the endogenous gene encoding the p-NBE polypeptide is disrupted (e.g., via a disruption cassette comprising a selectable marker) at a nucleotide position encoding a p-NBE substrate binding pocket residue, a p-NBE active site catalytic triad residue, a region of the p-NBE AE domain, at the −1, 0, +1 transcription start site, in the 5' promoter region, and the like.

In other embodiments, the genetic modification (i.e., which reduces or eliminates p-NBE activity in the modified cell) is a down-regulation of a gene encoding a p-NBE polypeptide comprising at least 60% sequence identity to the p-NBE polypeptide of SEQ ID NO: 2. In certain embodiments, down-regulation of a gene encoding a p-NBE comprises introducing (and expressing) in a *Bacillus* host cell an RNA molecule complementary to a gene encoding a p-NBE. In certain other embodiments, down-regulation of a gene encoding a p-NBE comprises (a) complete or partial deletion of the endogenous p-NBE promoter nucleic acid sequence, (b) complete or partial deletion of the endogenous p-NBE terminator nucleic acid sequence, combinations thereof, and optionally deletion of other 5' UTRs and/or 3' UTR nucleic acid sequence associated with a gene encoding a p-NBE polypeptide comprising at least 60% sequence identity to the p-NBE polypeptide of SEQ ID NO: 2.

Thus, certain embodiments of the disclosure are related to genetically modified *Bacillus* host cells expressing/producing β-galactosidase and/or lactase enzymes, and the use of such enzymes for the production of galactooligosaccharide (GOS) compositions in one or more dairy related end products. In certain embodiments, the polypeptide comprising β-galactosidase activity or transgalactosylating activity is selected from the group consisting of a *Bifidobacterium bifidum* polypeptide comprising 90% sequence identity to SEQ ID NO: 4, SEQ ID NO: 6, SEQ ID NO: 8, SEQ ID NO:10, SEQ ID NO: 12, SEQ ID NO: 14 or SEQ ID NO: 16, a *Kluyveromyces lactis* polypeptide comprising 90% sequence identity to SEQ ID NO: 17, an *Aspergillus oryzae* polypeptide comprising 90% sequence identity to SEQ ID NO: 18 or a *Lactobacillus delbrueckii* polypeptide comprising 90% sequence identity to SEQ ID NO: 26. In other embodiments, the polypeptide comprising β-galactosidase activity or transgalactosylating activity is encoded by a polynucleotide comprising 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 25.

In another embodiment, the *Bacillus* host cell is selected from the group consisting of *B. subtilis*, *B. licheniformis*, *B. lentus*, *B. brevis*, *B. stearothermophilus*, *B. alkalophilus*, *B. amyloliquefaciens*, *B. clausii*, *B. sonorensis*, *B. halodurans*, *B. pumilus*, *B. lautus*, *B. pabuli*, *B. cereus*, *B. agaradhaerens*, *B. akibai*, *B. clarkii*, *B. pseudofirmus*, *B. lehensis*, *B. megaterium*, *B. coagulans*, *B. circulans*, *B. gibsonii*, and *B. thuringiensis*. In a particular embodiment, the *Bacillus* host cell is *Bacillus subtilis*. In certain other embodiments, the host cell is further modified to be deficient in detectable lipase side activities, phospholipase side activities, cellulase side activities, pectinase side activities, amylase side activities, protease side activities and/or mannanase side activities.

Thus, in certain embodiments, the *Bacillus* host cell comprises an expression vector encoding a polypeptide comprising β-galactosidase activity or transgalactosylating activity. In certain embodiments, the *Bacillus* host cell is transformed with the expression vector/construct prior to performing the genetic modification which reduces or eliminates the endogenous p-NBE activity, while in other embodiments, the *Bacillus* host cell is transformed with the expression vector/construct after/subsequent to performing the genetic modification which reduces or eliminates the endogenous p-NBE activity.

Thus, certain other embodiments of the disclosure are related to a polypeptide (i.e., enzyme) comprising β-galactosidase activity or transgalactosylating activity produced by a modified *Bacillus* cell of the disclosure. Certain embodiments are directed to such purified β-galactosidase or transgalactosylating polypeptides produced by the modified *Bacillus* host cells, wherein the purified β-galactosidase or transgalactosylating polypeptides are free of detectable p-NBE side activity. In certain embodiments, a β-galactosidase or transgalactosylating polypeptide of the disclosure is a liquid composition or a solid composition. In certain embodiments, a β-galactosidase or transgalactosylating polypeptide of the disclosure is a spray-dried solid.

In other embodiments, the purified β-galactosidase or transgalactosylating polypeptide is free from detectable phospholipase side activities, cellulase side activities, pectinase side activities, amylase side activities, protease side activities and/or mannanase side activities.

In other embodiments, the disclosure is related to one or more dairy products comprising β-galactosidase or transgalactosylating polypeptides produced by the modified *Bacillus* cells of the disclosure.

Thus, certain embodiments of the disclosure are directed to methods for producing dairy products comprising galactooligosaccharides (GOSs), wherein the dairy products produced therefrom are free from unwanted/undesirable p-NBE side activity. Thus, in certain embodiments, a method for producing a diary product comprising galactooligosaccharides (GOSs) comprises adding a β-galactosidase activity or transgalactosylating activity polypeptide of the disclosure to a diary product comprising lactose.

In another embodiment, the disclosure is related to a method for producing a polypeptide composition having β-galactosidase activity or transgalactosylating activity, wherein the polypeptide composition does not comprise detectable para-nitrobenzylesterase (p-NBE) activity therein, the method comprising: (a) providing a parental *Bacillus* host cell comprising and expressing a polynucleotide construct encoding a polypeptide having β-galactosidase activity or transgalactosylating activity, (b) modifying the *Bacillus* host cell of step (a) by deleting, disrupting or down-regulating a gene encoding a p-NBE polypeptide comprising at least 60% sequence identity to the p-NBE polypeptide of SEQ ID NO: 2, (c) culturing the modified host cell of step (b) under conditions suitable to express the polypeptide having β-galactosidase activity or transgalactosylating activity, and (d) isolating the polypeptide having β-galactosidase activity or transgalactosylating activity, wherein the isolated polypeptide composition having β-galactosidase activity or transgalactosylating activity does not comprise detectable p-NBE activity.

In another embodiment, the disclosure is related to a method for producing a polypeptide composition having β-galactosidase activity or transgalactosylating activity, wherein the polypeptide composition does not comprise detectable para-nitrobenzylesterase (p-NBE) activity therein, the method comprising: (a) obtaining a parental *Bacillus* host cell and modifying the parental cell by deleting, disrupting or down-regulating a gene encoding a p-NBE polypeptide comprising at least 60% sequence identity to the p-NBE polypeptide of SEQ ID NO: 2, (b) introducing into the modified cell of step (a) an expression construct encoding a polypeptide having β-galactosidase activity or transgalactosylating activity, (c) culturing the host cell of step (b) under conditions suitable to express the polypeptide having β-galactosidase activity or transgalactosylating activity, and (d) isolating the polypeptide having β-galactosidase activity or transgalactosylating activity, wherein the isolated polypeptide composition having β-galactosidase activity or transgalactosylating activity does not comprise detectable p-NBE activity.

In certain embodiments of the methods, the modification comprises a deletion, disruption or down-regulation of a gene encoding a p-NBE polypeptide comprising at least 60% sequence identity to the p-NBE polypeptide of SEQ ID NO: 2. In other embodiments, the modification comprises the complete or partial deletion a gene encoding a p-NBE polypeptide comprising at least 60% sequence identity to the p-NBE polypeptide of SEQ ID NO: 2. In other embodiments, the partial deletion comprises deleting one or more codons encoding the p-NBE active site amino acids $Ser_{189}$, $Glu_{310}$) and/or $His_{399}$. In certain other embodiments, the partial deletion comprises a nucleotide frameshift deletion in the gene encoding the p-NBE, wherein the frameshift deletion results in an encoded protein thereof lacking p-NBE activity. In another embodiment, the partial deletion of a gene encoding a p-NBE polypeptide comprises deleting nucleotides of the p-NBE gene encoding amino acid residues 1-163 of SEQ ID NO: 2, deleting nucleotides of the p-NBE gene encoding amino acid residues 164-326 of SEQ ID NO: 2, deleting nucleotides of the p-NBE gene encoding amino acid residues 327-489 of SEQ ID NO: 2 or a combination thereof. In certain other embodiments, the partial deletion of a gene encoding a p-NBE polypeptide comprises deleting the acetyl esterase (AE) domain encoded by the p-NBE gene. In certain embodiments, in the AE domain is comprised within amino acid residues 85-211 of SEQ ID NO: 2. In other embodiments, the partial deletion of a gene encoding a p-NBE polypeptide comprises deleting one or more codons of the gene which encode the p-NBE substrate binding pocket. In another embodiment, the modification comprises a disruption of a gene encoding a p-NBE polypeptide comprising at least 60% sequence identity to the p-NBE polypeptide of SEQ ID NO: 2. In certain embodiment, the p-NBE gene disruption comprises the insertion of a selectable marker into the p-NBE gene. In other embodiments, the modification is a down-regulation of a gene encoding a p-NBE polypeptide comprising at least 60% sequence identity to the p-NBE polypeptide of SEQ ID NO: 2. In certain other embodiments, down-regulation of a gene encoding a p-NBE comprises introducing and expressing in the host cell an RNA molecule complementary to a gene encoding a p-NBE. In other embodiments, down-regulation of a gene encoding a p-NBE comprises (a) complete or partial deletion of the endogenous p-NBE promoter nucleic acid sequence, (b) complete or partial deletion of the endogenous p-NBE terminator nucleic acid sequence, combinations thereof, and optionally deletion of other 5' UTRs and/or 3' UTR nucleic acid sequence associated with a gene encoding a p-NBE polypeptide comprising at least 60% sequence identity to the p-NBE polypeptide of SEQ ID NO: 2.

In another embodiment, the polypeptide comprising β-galactosidase activity or transgalactosylating activity is selected from the group consisting of a *Bifidobacterium bifidum* polypeptide comprising 90% sequence identity to SEQ ID NO: 4, SEQ ID NO: 6, SEQ ID NO: 8, SEQ ID NO:10, SEQ ID NO: 12, SEQ ID NO: 14, SEQ ID NO: 16, a *Kluyveromyces lactis* polypeptide comprising 90% sequence identity to SEQ ID NO: 17, an *Aspergillus oryzae* polypeptide comprising 90% sequence identity to SEQ ID NO: 18 and a *Lactobacillus delbrueckii* polypeptide comprising 90% sequence identity to SEQ ID NO: 26.

In other embodiments, the polypeptide comprising β-galactosidase activity or transgalactosylating activity is encoded by a polynucleotide comprising 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 25.

In other embodiments, the *Bacillus* host cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B. akibai, B. clarkii, B. pseudofirmus, B. lehensis, B. megaterium, B. coagulans, B. circulars, B. gibsonii*, and *B. thuringiensis*. In certain embodiments, the host cell is *Bacillus subtilis*.

In other embodiments of the methods, the host cell is further modified to be deficient in detectable lipase side activities, phospholipase side activities, cellulase side activities, pectinase side activities, amylase side activities, protease side activities and/or mannanase side activities.

In another embodiment the disclosure is directed to a polypeptide comprising β-galactosidase activity or transgalactosylating activity produced by the methods of the disclosure.

In other embodiments, the disclosure is related to purified β-galactosidase or transgalactosylating polypeptides produced by the methods of the disclosure, wherein the purified β-galactosidase or transgalactosylating polypeptides are free of detectable p-NBE side activity. In certain other embodiments, the disclosure is directed to purified β-galactosidase or transgalactosylating polypeptides produced by the method of the disclosure, wherein the purified β-galactosidase or transgalactosylating polypeptides are free from phospholipase side activities, cellulase side activities, pectinase side activities, amylase side activities, protease side activities and/or mannanase side activities. In certain other embodiments, the disclosure is related to dairy products comprising purified β-galactosidase or transgalactosylating polypeptides produced by the methods of the disclosure.

BRIEF DESCRIPTION OF DRAWINGS

FIG. 1 shows the results of agar spot plate assays for detecting lipase and phospholipase activity, wherein yellow haloes represent a drop in pH resulting from the cleavage of a lipase or phospholipase substrate, resulting in free fatty acids and an equivalent proton ($H^+$).

FIG. 2, panel A is a picture of the zymogram gel showing "clear" zones where the lipase activity is located. FIG. 2, panel B and FIG. 2, panel C are the Isoelectric gel parts, where panel B was overlaid and incubated with panel A and panel C were Coomassie stained. Arrows in panel B and panel C indicate the location of the lipase activity which was cut out for mass spectroscopy analysis.

FIG. 13 shows the amino acid sequence of the *B. subtilis* para-Nitrobenzylesterase of SEQ ID NO: 2, wherein double underlined residues 85-211 indicate the AE domain, lower case bold residues (e.g., s-189, e-310 and h-399) indicate catalytic triad residues and BOLD upper case residues indicate substrate binding pocket residues.

BRIEF DESCRIPTION OF THE BIOLOGICAL SEQUENCES

Figure 1A:
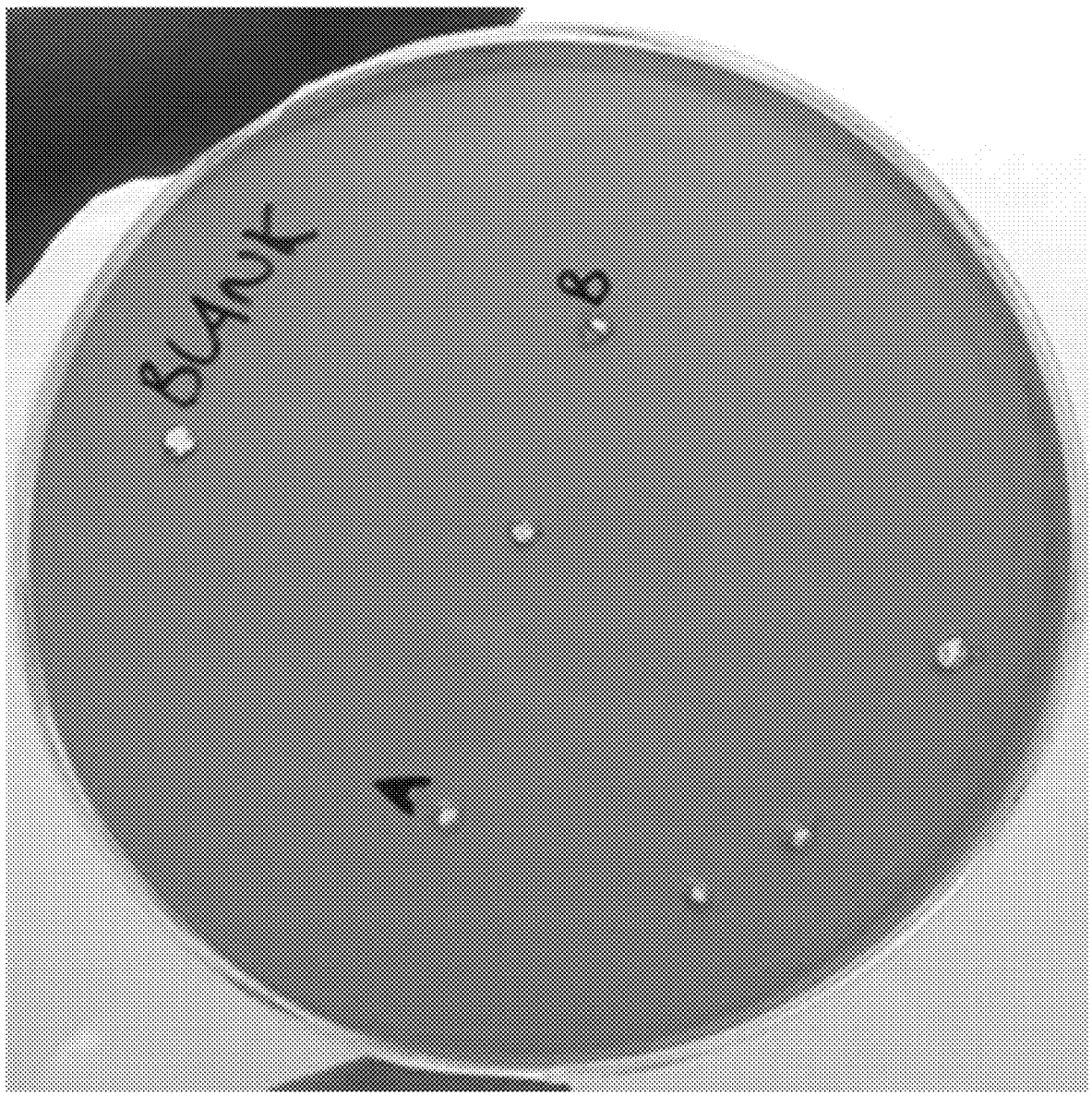
FIG. 1A shows the spot plate assay results using only a phospholipase substrate (i.e., lecithin substrate).

SEQ ID NO: 1 is a nucleic acid sequence encoding a *Bacillus subtilis* para-nitrobenzylesterase (p-NBE) of SEQ ID NO: 2.

SEQ ID NO: 2 is the amino acid sequence of a *Bacillus subtilis* para-nitrobenzylesterase.

SEQ ID NO: 3 is a nucleic acid sequence encoding an extracellular lactase from *Bifidobacterium bifidum* DSM20215.

SEQ ID NO: 4 is the amino acid sequence of an extracellular lactase from *B. bifidum* DSM20215, encoded by SEQ ID NO: 3.

SEQ ID NO: 5 is a nucleic acid sequence encoding a truncated *B. bifidum* lactase of SEQ ID NO: 6 (referred to herein as "BIF_917").

SEQ ID NO: 6 is protein BIF_917, an 887 amino acid truncated fragment of SEQ ID NO: 4, encoded by the nucleic acid of SEQ ID NO: 5.

SEQ ID NO: 7 is a nucleic acid sequence encoding a truncated *B. bifidum* lactase of SEQ ID NO: 8 (referred to herein as "BIF_955").

SEQ ID NO: 8 is protein BIF_955, a 965 amino acid truncated fragment of SEQ ID NO: 4, encoded by the nucleic acid of SEQ ID NO: 7.

SEQ ID NO: 9 is a nucleic acid sequence encoding a truncated *B. bifidum* lactase of SEQ ID NO: 10 (referred to herein as "BIF_1068").

SEQ ID NO: 10 is protein BIF_1068, a 1,038 amino acid truncated fragment of SEQ ID NO: 4, encoded by the nucleic acid of SEQ ID NO: 9.

SEQ ID NO: 11 is a nucleic acid sequence encoding a truncated *B. bifidum* lactase of SEQ ID NO: 12 (referred to herein as "BIF_1172").

SEQ ID NO: 12 is protein BIF_1172, a 1,142 amino acid truncated fragment of SEQ ID NO: 4, encoded by the nucleic acid of SEQ ID NO: 11.

SEQ ID NO: 13 is a nucleic acid sequence encoding a truncated *B. bifidum* lactase of SEQ ID NO: 14 (referred to herein as "BIF_1241").

SEQ ID NO: 14 is protein BIF_1241, a 1,211 amino acid truncated fragment of SEQ ID NO: 4, encoded by the nucleic acid of SEQ ID NO: 13.

SEQ ID NO: 15 is a nucleic acid sequence encoding a truncated *B. bifidum* lactase of SEQ ID NO: 16 (referred to herein as "BIF_1326").

SEQ ID NO: 16 is protein BIF_1326, a 1,296 amino acid truncated fragment of SEQ ID NO: 4, encoded by the nucleic acid of SEQ ID NO: 15.

SEQ ID NO: 17 is the amino acid sequence of a lactase from *Kluyveromyces lactis*.

SEQ ID NO: 18 is the amino acid sequence of a lactase from *Aspergillus oryzae*.

SEQ ID NO: 19 is oligonucleotide primer I-SceI-1.

SEQ ID NO: 20 is oligonucleotide primer I-SceI-2.

SEQ ID NO: 21 is oligonucleotide primer sequence number 981.

SEQ ID NO: 22 is oligonucleotide primer sequence number 984.

SEQ ID NO: 23 is oligonucleotide primer sequence number 985.

SEQ ID NO: 24 is oligonucleotide primer sequence number 983.

SEQ ID NO: 25 is a nucleic acid sequence encoding a *Lactobacillus delbrueckii* transgalactosylating polypeptide of SEQ ID NO: 26.

SEQ ID NO: 26 is the amino acid sequence of a *Lactobacillus delbrueckii* transgalactosylating polypeptide.

DETAILED DESCRIPTION

In certain embodiments, the present disclosure is directed to modified *Bacillus* host cells expressing/producing β-galactosidase enzymes and/or lactase enzymes and the use of such enzymes for the production of galactooligosaccharide (GOS) compositions in one or more dairy related end products. For example, in certain enzyme products (e.g., a β-galactosidase product), small amounts of unwanted enzyme activity mainly originate from the production host cell and are referred to as enzyme side activity. As described herein, the present disclosure is directed to reducing/eliminating unwanted enzyme side activities in host cells used for the production of β-galactosidase and/or lactase enzymes for use in dairy products formulations/applications.

More particularly, in certain embodiments the disclosure is directed to expressing/producing such β-galactosidase and/or lactase enzymes in modified *Bacillus* host cells, wherein such enzymes produced and purified from the modified *Bacillus* host cells are free of unwanted/undesirable enzymatic side activities including, but not limited to, unwanted/undesirable lipase side activities, phospholipase side activities, cellulase side activities, pectinase side activities, amylase side activities, protease side activities, mannanase side activities and the like.

Thus, certain embodiments of the disclosure are related to genetically modifying a *Bacillus* host cell for the production of β-galactosidase and/or lactase enzymes in the absence of unwanted enzymatic side activities. In certain embodiments, a *Bacillus* host cell of the disclosure is genetically modified to produce β-galactosidase and/or lactase enzymes in the absence of unwanted/undesirable para-nitrobenzylesterase side activity. Thus, in certain embodiments, a *Bacillus* host cell of the disclosure is genetically modified by deleting, disrupting or down-regulating an endogenous *Bacillus* gene which encodes a para-nitrobenzylesterase enzyme. As described herein, such genetically modified *Bacillus* host cells are particularly useful in the production of β-galactosidase and/or lactase enzymes, wherein such β-galactosidase and/or lactase enzymes are particularly free of unwanted para-nitrobenzylesterase enzymatic side-activity which causes highly undesirable off-flavors and smells when used in dairy related end-products.

In certain other embodiments, a genetically modified *Bacillus* host cell of the disclosure comprising a deleted, disrupted or down-regulated endogenous gene encoding a para-nitrobenzylesterase enzyme, further comprises a deleted, disrupted or down-regulated gene encoding at least one additional unwanted/undesirable enzymatic side activity selected from a lipase side activity, a phospholipase side activity, a cellulase side activity, a pectinase side activity, an amylase side activity, a protease side activity, a mannanase side activity and the like.

Thus, in certain embodiments, a genetically modified *Bacillus* host cell of the disclosure (i.e., comprising a genetic modification which deletes, disrupts or down-regulates an endogenous gene encoding a para-nitrobenzylesterase enzyme) is transformed with a polynucleotide (e.g., an expression construct) encoding a β-galactosidase and/or lactase enzyme of the disclosure. More particularly, as described herein, the β-galactosidase and/or lactase enzymes of the disclosure, which are expressed/produced in the genetically modified *Bacillus* host cells of the disclosure are particularly useful in dairy product applications.

More specifically, as set forth in the Examples section below, the β-galactosidase and/or lactase enzymes expressed/produced in such genetically modified *Bacillus* host cells, which β-galactosidase and/or lactase enzymes are isolated and purified therefrom, are free of detectable para-nitrobenzylesterase side activity. More particularly, as described in the Examples herein, Applicants of the instant disclosure identified a para-nitrobenzylesterase as the enzymatic side activity responsible for the foul off-flavor smells/tastes of dairy products which were formulated with such β-galactosidase and/or lactase enzymes. Thus, the genetically modified *Bacillus* host cells of the disclosure (i.e., comprising a genetic modification which deletes, disrupts or down-regulates a gene encoding a para-nitrobenzylesterase) find particular utility for the production of such β-galactosidase and/or lactase enzymes without the contaminating (i.e., unwanted/undesirable) para-nitrobenzylesterase side activity thereof.

I. Definitions

In view of the modified *Bacillus* spp. host cells expressing/producing β-galactosidases and/or lactases in the absence of unwanted para-nitrobenzylesterase (hereinafter, "p-NBE") side activity and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "transgalactosylase" means an enzyme that, among other things, is able to transfer galactose to the hydroxyl groups of D-galactose or D-glucose, whereby galactooligosaccharides are produced. In one aspect, a transgalactosylase is identified by reaction of the enzyme on lactose in which the amount of galactose generated is less than the amount of glucose generated at any given time.

As used herein, the term "transgalactosylating activity" means the transfer of a galactose moiety to a molecule other than water ($H_2O$). The transgalactosylating activity can be measured as [glucose]-[galactose] generated at any given time during the reaction, or by direct quantification of the galactooligosaccharides (GOSs) generated at any given time during the reaction. Such activity measurements may be performed by methods known in the art (e.g., an HPLC method).

As used herein, the term "β-galactosidase activity" refers to the ability of an enzyme to hydrolyze β-galactoside molecules (e.g., hydrolyzing lactose disaccharides into monosaccharides glucose and galactose).

As used herein, calculating the "transgalactosylating activity/β-galactosidase activity" (ratio), the β-galactosidase activity is measured as [galactose] generated at any given time during the reaction. Such activity ratio measurements may be performed by methods known in the art (e.g., an HPLC method).

As used herein, the phrase "β-galactosidase having transgalactosylating activity" means a β-galactosidase having a ratio of transgalactosylation activity above 100%, such as above 105%, 125%, 150%, 175%, 200% and the like. Examples of β-galactosidases having transgalactosylating activity can be derived from, but are not limited to, *Aspergillus oryzae*, *Bacillus circulars*, *Ruminococcus*, *Bifidobacterium*, *Geobacillus stearothermophilus*, *Lactobacillus delbrueckii*, *Bacillus stearothermophilus* and *Lactobacillus plantarum* (Oliveira et al., 2011).

As used herein, the terms "[Glucose]" or "glucose concentration" means the glucose concentration in % by weight and the terms "[Galactose]" or "galactose concentration" means the galactose concentration in % by weight.

As used herein, the phrase "lactose has been transgalactosylated" means that a galactose molecule has been covalently linked to the lactose molecule, such as for example covalently linked to any of the free hydroxyl groups in the lactose molecule, or as generated by internal transgalatosylation (e.g., forming allolactose).

In the present context, the term "which polypeptide is spray-dried" means that the polypeptide has been obtained by spray-drying a polypeptide which is in solution or suspension at an appropriate temperature and for an appropriate period removing the water.

As used herein, the term "milk", in the context of the present disclosure, is to be understood as the lacteal secretion obtained from any mammal, such as cows, sheep, goats, buffaloes, camels and the like.

As used herein, the term "milk-based substrate" means any raw and/or processed milk material, or a material derived from milk constituents. The milk-based substrate may be homogenized and/or pasteurized according to methods known in the art.

"Homogenizing" as used herein means intensive mixing to obtain a soluble suspension or emulsion. Homogenization may be performed so as to break up the milk fat into smaller sizes, such that the milk fat no longer separates from the milk. This may be accomplished, for example, by forcing the milk at high pressure through small orifices.

As used herein, "pasteurizing" means reducing or eliminating the presence of live organisms, such as microorganisms, in the milk-based substrate. Pasteurization is attained by maintaining a specified temperature and pressure for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

As used herein, a "dairy product" in the context of the present disclosure may be any food product wherein one of the major constituents is a milk-based substrate. Preferably, the major constituent is milk-based. In the present context, "one of the major constituents" means a constituent having a dry matter which constitutes more than 20%, preferably more than 30%, or more than 40%, of the total dry matter of the dairy product, whereas "the major constituent" means a constituent having a dry matter which constitutes more than 50%, preferably more than 60%, or more than 70%, of the total dry matter of the dairy product.

As used herein, a "fermented dairy product" in present context is to be understood as any dairy product wherein any type of fermentation forms part of the production process. Examples of fermented dairy products include, but are not limited to, yoghurt, buttermilk, créme fraiche, quark and fromage frais. Another example of a fermented dairy product is cheese. In certain embodiments, a fermented yogurt dairy product is a set-type yoghurt, a stirred yoghurt or a drinking yogurt. In other embodiments, a fermented dairy product is *Acidophilus* milk, Leben milk, Ayran milk, Kefir milk or Sauermilch milk. Such fermented dairy products may be produced by any method known in the art.

As used herein, an "isolated polynucleotide" refers to a polynucleotide that is isolated from a source. In certain aspects of the disclosure, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

As used herein, a "substantially pure polynucleotide" refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form (i.e., that the polynucleotide preparation is essentially free of other polynucleotide material with which it is natively or recombinantly associated). The polynucleotides may be of genomic, cDNA, RNA, semisynthetic, synthetic origin, or any combinations thereof.

As used herein, an "isolated polypeptide" refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

As used herein, a "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form (i.e., that the polypeptide preparation is essentially free of other polypeptide material with which it is natively or recombinantly associated). This can be accomplished, for example, by preparing the polypeptide by well-known recombinant methods or by classical purification methods.

As used herein, a "substantially pure β-galactosidase polypeptide" and a "substantially pure lactase polypeptide" refer to a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

More particularly, with regard to the present disclosure, a "substantially pure β-galactosidase polypeptide" and a "substantially pure lactase polypeptide" refer to such polypeptides which are essentially free of detectable "p-nitrobenzylesterase activity". More specifically, as described herein, a substantially pure β-galactosidase polypeptide composition and/or a substantially pure lactase polypeptide composition, which are completely free of detectable "p-nitrobenzylesterase activity", can be obtained by expressing/producing such β-galactosidase polypeptides and/or lactase polypeptides in the genetically modified *Bacillus* host cell of the disclosure (i.e., a *Bacillus* host cell comprising a deletion, disruption or down-regulation of a gene (e.g., SEQ ID NO: 1) encoding p-nitrobenzylesterase of SEQ ID NO: 2. In certain other embodiments, a substantially pure "β-galactosidase polypeptide" or a "substantially pure lactase polypeptide" is essentially free of detectable p-nitrobenzylesterase activity and is essentially free of at least one additional unwanted side activity selected from the group consisting of cellulase activity, mannanase activity, pectinase activity, amylase activity, protease activity and the like.

Thus, as used herein, the term "substantially free from cellulase" means a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of cellulase. Herein, the term "substantially free from" can therefore be seen as being synonymous with the terms "isolated polypeptide" and "polypeptide in isolated form."

As used herein, the term "substantially free from mannanase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of mannanase. Herein, the term "substantially free from" can therefore be seen as being synonymous with the terms "isolated polypeptide" and "polypeptide in isolated form."

As used herein, the term "substantially free from pectinase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of pectinase. Herein, the term "substantially free from" can therefore be seen as being synonymous with the terms "isolated polypeptide" and "polypeptide in isolated form."

As used herein, the term "substantially free from amylase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of amylase. Herein, the term "substantially free from" can therefore be seen as being synonymous with the terms "isolated polypeptide" and "polypeptide in isolated form."

As used herein, the term "stabilizer" means any stabilizer for stabilizing the polypeptide, e.g., a polyol such as glycerol or propylene glycol, a sugar or a sugar alcohol, lactic acid, boric acid, or a boric acid derivative (e.g., an aromatic borate ester). In one aspect, the stabilizer is not a polyol, or the polyol is present at a level of 0.1 weight % or less.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. As used herein, the term "heterologous" gene(s) comprise native genes (or ORFs) inserted into a non-native organism and/or chimeric genes inserted into a native or non-native organism.

As used herein, the terms "foreign polynucleotide" or "heterologous polynucleotide" (and variations thereof) are defined as (A) a polynucleotide that is not native to the host cell, (B) a polynucleotide that is native to the host cell, but which polynucleotide has been modified through the use of genetic elements which are not natively associated with the polynucleotide (e.g., heterologous promoters, 5' UTRs, 3' UTRs and the like) as isolated from the host cell, or (C) the use of native elements that have been manipulated to function in a manner that does not normally occur in the host cell.

As defined herein, a "heterologous" nucleic acid construct or a "heterologous" nucleic acid sequence has a portion of the sequence which is not native to the cell in which it is expressed.

As used herein, a "transformed cell" includes bacterial cells (e.g., *Bacillus* cells) which have been transformed by use of recombinant DNA techniques. Transformation generally occurs via the introduction of one or more nucleotide sequences (e.g., polynucleotides) into a cell. The introduced nucleotide sequence(s) may also be a heterologous nucleotide sequence (i.e., a nucleic sequence not endogenous to the cell).

As used herein, the term "nucleic acid construct" refers to a nucleic acid molecule (e.g., a polynucleotide molecule), either single-stranded or double-stranded, which is isolated from a naturally occurring gene or is modified to contain segments of nucleic acids in a manner that would not otherwise exist in nature or is synthetic. The term nucleic acid construct is synonymous with the term "expression cassette" when the nucleic acid construct contains the control sequences required for expression of a coding sequence.

As used herein, the term "control sequences" is defined to include all components, which are necessary or advantageous for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the term "promoter" is defined as a DNA sequence that binds RNA polymerase and directs the polymerase to the correct downstream transcriptional start site of a polynucleotide encoding a polypeptide. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and/or other nucleotide sequences capable of interacting with transcription factors. The promoter can be a wild-type, variant, hybrid, or a consensus promoter.

As used herein, the term "promoter region" is defined as a nucleotide sequence comprising one or more (several) promoter sequences (e.g., a dual promoter, a triple promoter and the like).

As used herein, the term "operably linked" denotes a configuration in which a control sequence (e.g., a promoter sequence) is placed at an appropriate position relative to the coding sequence of the polynucleotide sequence such that the control sequence directs the expression of the coding sequence of a polypeptide. Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, synthetic, or recombinant nucleotide sequence.

As used herein, a "variant" or "variants" may refer to either polypeptides or nucleic acids. The term "variant" may be used interchangeably with the term "mutant". Variants include insertions, substitutions, transversions, truncations, deletions and/or inversions at one or more locations in the amino acid or nucleotide sequence.

As used herein, "expression" includes any step involved in the production of a polypeptide of interest (POI) including, but not limited to, transcription, post-transcriptional modification, translation, post-translational modification and secretion.

As used herein, an "expression vector" and "expression construct" are used interchangeably and refer to a linear or circular DNA molecule that comprises a polynucleotide encoding a polypeptide of interest, and is operably linked to additional nucleotides that provide for its expression.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

As used herein, the term "host cell" refers to a cell or cell line into which a recombinant expression vector for production of a polypeptide may be introduced for expression of the polypeptide. For example, in certain embodiments, a host cell of the disclosure comprises an expression construct encoding a β-galactosidase and/or lactase enzyme of the disclosure. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

As used herein, the terms a "modified host cell", an "altered host cell" and a "genetically modified host cell" are used interchangeably and refer to recombinant host cells that comprise at least a modification which deletes, disrupts or down-regulates a gene encoding a p-nitrobenzylesterase polypeptide comprising at least 60% sequence identity to the p-nitrobenzylesterase polypeptide of SEQ ID NO: 2. For example, a "genetically modified" host cell of the instant disclosure may be further defined as a "genetically modified (host) cell" which is derived from a parental host cell, wherein the modified (daughter) cell comprises at least a modification which deletes, disrupts or down-regulates a gene encoding a p-nitrobenzylesterase polypeptide comprising at least 60% sequence identity to the p-nitrobenzylesterase polypeptide of SEQ ID NO: 2.

As defined herein, an "unmodified cell", an "unaltered cell", an "unmodified host cell", and an "unaltered host cell" are used interchangeably and refer to "unmodified" (parental) host cells that do not comprise a modification which deletes, disrupts or down-regulates a gene encoding a p-nitrobenzylesterase polypeptide comprising at least 60% sequence identity to the p-nitrobenzylesterase polypeptide of SEQ ID NO: 2. In certain embodiments, the "unmodified" (parental) host cell may be referred to as a "control cell", particularly when being compared with, or relative to, a "modified" (daughter) host cell of the disclosure.

As used herein, when the expression and/or production of a POI in an "unmodified" (parental) cell (i.e., a control cell) is being compared to the expression and/or production of the same POI in a "modified" (daughter) cell, it will be understood that the "modified" and "unmodified" cells are grown/cultured/fermented under essentially the same conditions (e.g., the same conditions such as media, temperature, pH and the like).

As used herein, the terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory/control element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more the genes disclosed herein.

As used herein, "disruption of a gene", "gene disruption", "inactivation of a gene" and "gene inactivation" are used interchangeably and refer broadly to any genetic modification that substantially prevents a host cell from producing a functional gene product (e.g., a protein). Exemplary methods of gene disruptions include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the production of the functional gene product (i.e., a protein).

As used herein, the terms "down-regulation" of gene expression include any method that results in lower (down-regulated) expression of a gene. For example, the down-regulation of a gene can be achieved by RNA-induced gene silencing, genetic modifications of control elements such as the promoter, ribosomal binding site (RBS)/Shine-Dalgarno sequences, untranslated regions (UTRs), codon changes, and the like. Thus, in certain embodiments, a *Bacillus* (host) cell of the disclosure comprising a gene encoding an unwanted para-nitrobenzylesterase (p-NBE) activity is genetically modified to down-regulate the expression of the p-NBE gene.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "culturing" refers to growing a population of microbial cells under suitable conditions for growth, in a liquid or solid culture medium.

The term "culture medium" refers to the medium used in this process.

The term "introduced" in the context of inserting a nucleic acid sequence into a cell includes "transfection", "transformation", or "transduction", and refers to the incorporation of a nucleic acid sequence into a eukaryotic or prokaryotic cell, wherein the nucleic acid sequence may be incorporated into the genome of the cell (e.g., chromosome, plasmid, plastid, or mitochondrial DNA), converted into an autonomous replicon, or transiently expressed.

As used herein, the terms "transformed" and "stably transformed" refer to a cell that has an introduced (exogenous) nucleic acid sequence integrated into its genome or as an episomal plasmid that is maintained through multiple generations.

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is well within the knowledge of those having skill in the art.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "orthologue" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.) and Devereux et. al., 1984).

As used herein, an "analogous sequence" is one wherein the function of the gene (e.g., a para-nitrobenzylesterase) is essentially the same as the para-nitrobenzylesterase gene derived from a *Bacillus* cell of the disclosure. Additionally, analogous genes include at least 60%, 65%, 70%, 75%, 80%, 85%, 90%, 95%, 97%, 98%, 99% or 100% sequence identity with the para-nitrobenzylesterase sequence of SEQ ID NO: 1. Analogous sequences are determined by known methods of sequence alignment. A commonly used alignment method is BLAST, although there are other methods that also find use in aligning sequences.

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$ −5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5%

SDS at room temperature (RT) and two additional times in 0.1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a non-critical target for a cell to initiate DNA uptake.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, "the genus *Bacillus*" includes all species within the genus "*Bacillus*'" as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulars*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*".

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, Molecular Cloning: A Laboratory Manual, second edition (Sambrook et al., 1989); Oligonucleotide Synthesis (M. J. Gait, ed., 1984); Current Protocols in Molecular Biology (Ausubel et al., eds., 1994); PGR: The Polymerase Chain Reaction (Mullis et al., eds., 1994); and Gene Transfer and Expression: A Laboratory Manual (Kriegler, 1990).

II. β-Galactosidase/Lactase Polypeptides

In enzyme products (e.g., a β-galactosidase product), small amounts of unwanted enzyme activity mainly originate from the production host cell and are referred to as enzyme side activity. As described herein, the present disclosure is directed to reducing unwanted enzyme side activities in host cells used for the production of β-galactosidase and/or lactase enzymes for use in dairy products formulations/applications. Thus, the enzyme activity in dairy applications should preferably be measured at the appropriate pH and temperature for the particular application. For example, in milk, the pH varies from 6.4 to 6.8, yoghurt pH is approximately 4, infant formula pH ranges from 5.9-7.3, mozzarella has a pH 5.2-5.5 and mayonnaise pH 4. Optimally, the level of undesirable activity can be determined by application tests in each intended application.

Thus, as set forth above, certain embodiments of the disclosure are directed to genetically modified *Bacillus* host cells expressing/producing β-galactosidase and/or lactase enzymes, and the use of such enzymes for the production of galactooligosaccharide (GOS) compositions in one or more dairy related end products. More specifically, certain embodiments are directed to expressing/producing such β-galactosidase and/or lactase enzymes in modified *Bacillus* host cells, wherein such enzymes produced and purified from the modified *Bacillus* host cells are free of unwanted/undesirable enzymatic side activities including, but not limited to, unwanted/undesirable lipase side activities, phospholipase side activities, cellulase side activities, pectinase side activities, amylase side activities, protease side activities, mannanase side activities and the like.

In certain embodiments, such β-galactosidase and/or lactase enzymes are produced in genetically modified *Bacillus* host cells and purified therefrom, wherein such purified enzymes are free of unwanted/undesirable p-nitrobenzylesterase activity. Thus, in particular embodiments, a substantially pure β-galactosidase polypeptide composition and/or a substantially pure lactase polypeptide composition, which are completely free of detectable "p-nitrobenzylesterase activity", are obtained by expressing/producing such β-galactosidase polypeptides and/or lactase polypeptides in a genetically modified *Bacillus* host cell of the disclosure, wherein the modified *Bacillus* host cells comprises a deletion, disruption or down-regulation of a gene (e.g., SEQ ID NO: 1) encoding a p-nitrobenzylesterase of SEQ ID NO: 2. For example, as presented in the Examples section below, a modified *Bacillus* (daughter) cell of the disclosure (i.e., comprising a deleted, disrupted or down-regulated gene (e.g., SEQ ID NO: 1) encoding a p-nitrobenzylesterase (e.g., SEQ ID NO: 2) completely eliminated the unwanted/undesirable p-nitrobenzylesterase side activity from the β-galactosidase and/or lactase products produced therefrom.

Furthermore, as described in the Examples section below, the elimination (e.g., deletion) of the gene encoding the unwanted/undesirable p-nitrobenzylesterase side activity (i.e., in the modified *Bacillus* host cells of the disclosure) completely eliminated the foul off-flavor detected in dairy products comprising/formulated with such the β-galactosidase and/or lactase enzymes.

Thus, certain embodiments of the disclosure are directed to the expression/production of 0-galactosidases and/or lactases in modified *Bacillus* host cells comprising a deleted, disrupted or down-regulated gene encoding a p-nitrobenzylesterase comprising 60% sequence identity to the p-nitrobenzylesterase of SEQ ID NO: 2. For example, in certain embodiments a modified *Bacillus* host cell of the disclosure (i.e., comprising a deleted, disrupted or down-regulated gene encoding a p-nitrobenzylesterase comprising 60% sequence identity to the p-nitrobenzylesterase of SEQ ID NO: 2) is transformed with a polynucleotide encoding a β-galactosidase enzyme or lactase enzyme, and the host cells grown/cultured under conditions such that the host cell expresses/produces the encoded β-galactosidase or lactase. Thus, the modified *Bacillus* host cells described herein are suitable for the expression/production of any β-galactosidase or lactase enzyme, wherein the purified β-galactosidase or lactase enzyme compositions and products thereof are free of detectable p-nitrobenzylesterase side activity.

For example, PCT International Publication Nos. WO2016/071504, WO2016/071500, WO2015/086746 and WO2011/120993 (each incorporated herein by reference in its entirety), disclose various β-galactosidase or lactase enzymes having transgalactosylating activity (and variants thereof having transgalactosylating activity). Thus, as described herein, the enzymes disclosed in PCT International Publication Nos. WO2016/071504, WO2016/071500, WO2015/086746 and WO2011/120993 (i.e having transgalactosylating activity) are particularly suitable for expression/production in the modified *Bacillus* host cells of the present disclosure. Stated another way, the expression/production of a β-galactosidase or lactase enzyme (having transgalactosylating activity) in a modified *Bacillus* host cell of the disclosure is not intended to be limited to a particular β-galactosidase or lactase amino acid sequence (or a particular gene/polynucleotide sequence encoding the same), so long as the β-galactosidase or lactase enzyme (having transgalactosylating activity) can be expressed/produced in the modified *Bacillus* host cell and is free of detectable p-nitrobenzylesterase activity.

In certain embodiments, a β-galactosidase or lactase polypeptide to be expressed in a modified *Bacillus* host cell of the disclosure comprises an amino acid sequence selected from SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18 and SEQ ID NO: 26. In other embodiments, a β-galactosidase or lactase polypeptide to be expressed in a modified *Bacillus* host cell of the disclosure comprises an amino acid sequence comprising about 80% sequence identity to any one of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 17, SEQ ID NO: 18 and SEQ ID NO: 2. In certain other embodiments, a β-galactosidase or lactase polypeptide to be expressed in a modified *Bacillus* host cell of the disclosure comprises a partial or truncated amino acid sequence of SEQ ID NO: 4.

Thus, in certain embodiments, the disclosure is directed to polypeptides having a ratio of transgalactosylating activity/β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In certain other embodiments, a polypeptide having transgalactosylating activity is selected from the group consisting of: (a) a polypeptide comprising an amino acid sequence having at least 90% sequence identity with SEQ ID NO: 6, wherein the polypeptide consists of at most 980 amino acid residues, (b) a polypeptide comprising an amino acid sequence having at least 97% sequence identity with SEQ ID NO: 8, wherein the polypeptide consists of at most 975 amino acid residues, (c) a polypeptide comprising an amino acid sequence having at least 96.5% sequence identity with SEQ ID NO: 10, wherein the polypeptide consists of at most 1,300 amino acid residues, (d) a polypeptide encoded by a polynucleotide that hybridizes under at least low stringency conditions with a nucleic acid sequence comprised in SEQ ID NO: 3, 5, 7, 9, 11, 13, 15 or 25 encoding the polypeptide of SEQ ID NO: 4, 6, 8, 10, 12, 14, 16 or 26; or the complementary strand thereof, (e) a polypeptide encoded by a polynucleotide comprising a nucleotide sequence having at least 70% identity to the nucleotide sequence encoding for the polypeptide of SEQ ID NO: 4, 6, 8, 10, 12, 14, 16 or 26 the nucleotide sequence comprised in SEQ ID NO: 3, 5, 7, 9, 11, 13, 15 or 25 encoding a mature polypeptide, and (f) a polypeptide comprising a deletion, insertion and/or conservative substitution of one or more amino acid residues of SEQ ID NO: 4, 6, 8, 10, 12, 14, 16 or 26.

In certain embodiments, a polypeptide of the disclosure comprises an amino acid sequence having at least 68%, 70%, 72%, 74%, 76%, 78%, 80%%, 85%, 90%, 91%, 92%, 93%, 94%, 95%, 96%, 97%, 98%, or 99%, sequence identity to the mature amino acid sequence of SEQ ID NO: 4, 6, 8, 10, 12, 14, 16, 17, 18 or 26.

In another embodiment, the disclosure is directed to a polypeptide having 90% sequence identity to the mature amino acid sequence of SEQ ID NO: 6.

In another embodiment, the disclosure is directed to a polypeptide having 90% sequence identity to the mature amino acid sequence of SEQ ID NO: 8.

In another embodiment, the disclosure is directed to a polypeptide having 96.5% sequence identity to the mature amino acid sequence of SEQ ID NO: 10.

In another embodiment, the disclosure is directed to a polypeptide having 96.5% sequence identity to the mature amino acid sequence of SEQ ID NO: 12.

In another embodiment, the disclosure is directed to a polypeptide having 96.5% sequence identity to the mature amino acid sequence of SEQ ID NO: 14.

In another embodiment, the disclosure is directed to a polypeptide having 90% sequence identity to the amino acid sequence of SEQ ID NO: 16.

In another embodiment, the disclosure is directed to a polypeptide having 90% sequence identity to the amino acid sequence of SEQ ID NO: 17.

In another embodiment, the disclosure is directed to a polypeptide having 90% sequence identity to the amino acid sequence of SEQ ID NO: 18.

In another embodiment, the disclosure is directed to a polypeptide having 90% sequence identity to the amino acid sequence of SEQ ID NO: 26.

In another embodiment, the disclosure is directed to a transgalactosylating polypeptide derived from *Bifidobacterium bifidum*. In another embodiment, the disclosure is directed to a transgalactosylating polypeptide derived from *Lactobacillus delbrueckii*.

Thus, the polypeptides disclosed herein have activity on carbohydrate bonds which have the β (1→4) conformation. This effectively put the enzymes into the IUBMB EC 3.2.1.23 class of β-galactosidases. This activity may be determined, for example, by utilizing synthetic substrates such as p-nitrophenol-B-D-galactopyranoside (PNPG), ortho-nitrophenol-p-D-galactopyranoside (ONPG) or β-D-galactopyranoside with chromogenic aglycons (XGal).

As an alternative way of determining whether a particular enzyme belongs to the EC 3.2.1.23 class of β-galactosidases is to incubate the enzyme with a substrate such as lactose, and measure the release of glucose by a method such as enzymatic determination, HPLC, TLC or other methods known to persons skilled in the art.

Thus, in certain embodiments, a polypeptide disclosed herein has a ratio of transgalactosylating activity/galactosidase activity of at least 1, at least 2.5, at least 3, at least 4, at least 5, at least 6, at least 7, at least 8, at least 9, at least 10, at least 11, or at least 12, as measured at a concentration of 100 ppm in a milk-based assay at 37° C. and 5% (w/w) lactose, after 15, 30 or 180 minutes of reaction.

In other embodiments, polypeptide(s) of the disclosure have a transgalactosylating activity such that more than 20%, more than 30%, more than 40%, up to 50% of the initial lactose is transgalactosylated as measured at a concentration of 100 ppm in a milk-based assay at 37° C. and 5% (w/w) lactose after 15, 30 or 180 such as 180 minutes of reaction.

In a further aspect, the polypeptide(s) have a β-galactosidase activity such that less than 80%, less than 70%, less than 60%, less than 50%, less than 40%, less than 30%, less than 20% of the lactose has been hydrolyzed as measured at a concentration of 100 ppm in a milk-based assay at 37° C. and 5% (w/w) lactose after 15, 30 or 180 such as 180 minutes of reaction. In another aspect, the β-galactosidase activity and/or the transgalactosylating activity are measured at a concentration of 100 ppm corresponding to 2.13 LAU, as specified in Method 4 of PCT International Publication No. WO2003/186286.

In certain embodiments, the polypeptides used herein have useful transgalactosylating activity over a range of pH of 4-9, such as 5-8, such as 5.5-7.5, such as 6.5-7.5.

In other embodiments, a homologous sequence includes an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites, etc. as the subject amino acid sequence. Although homology can also be considered in terms of similarity (i.e., amino acid residues having similar chemical properties/functions), in the context of the present disclosure it is preferred to express homology in terms of sequence identity.

Thus, the present disclosure also encompasses the use of variants, homologues and derivatives of any amino acid sequence of a polypeptide as defined herein, particularly those of SEQ ID NO: 4, 6, 8, 10, 12, 14, 16, 17, 18 or 26.

In preferred embodiments, the transgalactosylating polypeptides of the disclosure are expressed/produced in the modified host cells of the disclosure and are substantially isolated and purified therefrom. In another preferred embodiment, such transgalactosylating polypeptides expressed/produced in the modified host cells of the disclosure and purified therefrom comprise no detectable p-nitrobenzylesterase side activity (i.e., the purified/isolated transgalactosylating polypeptides are free of unwanted/undesirable p-nitrobenzylesterase activity).

To evaluate the expression of a particular wild-type or variant transgalactosylating polypeptide (e.g., β-galactosidase) in a modified host cell of the disclosure, assays measuring the expressed protein, the corresponding mRNA, or β-galactosidase activity are readily implemented. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the polypeptide, include, but are not limited to, ONPG based assays or determining glucose concentration in reaction mixtures.

Thus, the polypeptides described herein for the expression/production in the modified host cells of the disclosure comprise transgalactosylation activity. In certain embodiments, the ratio of transgalactosylating activity/β-galactosidase activity is at least 0.5, such as at least 1, at least 1.5, or at least 2, after 30 minutes of reaction, such as above a concentration of 3% (w/w) initial lactose concentration.

Thus, the β-galactosidase and/or lactase polypeptides of the disclosure (i.e., comprising transgalactosylating activity) and variants thereof are derivable from microbial sources, in particular from a filamentous fungus, yeast, or bacteria. Thus, the β-galactosidase and/or lactase polypeptides (comprising transgalactosylating activity) may be derived from a strain of *Agaricus*, (e.g., *A. bisporus*), *Ascovaginospora*, *Aspergillus* (e.g., *A. niger, A. awamon, A. foetidus, A. japonicus, A. oryzae*), *Candida, Chaetomium, Chaetotomastia, Dictyostelium* (e.g., *D. discoideum*), *Kluveromyces* (e.g., *K fragilis. K lactis*) *Mucor* (e.g., *M. javanicus, M. mucedo, M. subtilissimus*) *Neurospora* (e.g., *N. crassa*), *Rhizomucor, Rhizopus* (e.g., *R. arrhizus, R. japonicus, R. stolonifera*), *Sclerotini* (e.g., *S. libertiana*), *Torula, Torulopsis, Trichophyton* (e.g., *T. rubrum*) *Whetzelinia* (e.g., *W. sclerotiorum*), *Bacillus* (e.g., *B. coagulans, B. circulars, B. megaterium, B. novalis, B. subtilis, B. pumilus, B. stearothermophilus, B. thuringiensis*) *Bifidobacterium* (e.g., *B. longum, B. bifidum, B. animalis*), *Chryseobactenum, Citrobacter* (e.g., *C. freundii*) *Clostridium* (e.g., *C. perfringens*) *Diplodia* (e.g., *D. gossypina*), *Enterobacter* (e.g., *E. aerogenes, E. cloacae*), *Edwardsiella* (e.g., *E. tarda*), *Erwinia* (e.g., *E. herbicola*), *Escherichia* (e.g., *E. coli*), *Klebsiella* (e.g., *K. pneumoniae*) *Minococcum, Myrothesium, Proteus* (e.g., *P. vulgaris*), *Providencia* (e.g., *P. stuartii*) *Pycnoporus* (e.g., *P. cinnabannus, P. sanguineus*) *Ruminococcus* (e.g., *R. torques*), *Salmonella* (e.g., *S. typhimurium*) *Serratia* (e.g., *S. liquefasciens, S. marcescens*) *Shigella* (e.g., *S. flexneri*), *Streptomyces* (e.g., *S. antibioticus, S. castaneoglobisporus, S. vio-*

*leceoruber*) *Trametes, Trichoderma* (e.g., *T. reesei. T. viride*), *Yersinia* (e.g., *Y. enterocolitica*) and the like.

β-galactosidase and/or lactase polypeptides and variants thereof can be characterized by their nucleic acid sequence and/or primary amino acid sequence, by three dimensional structural modeling, and/or by specific activity. Additional characteristics of the polypeptide or polypeptide variants as defined herein include stability, pH range, oxidation stability and thermostability. Levels of expression and enzyme activity can be assessed using standard assays known to the artisan skilled in this field.

Thus, in certain embodiments, the introduction of a DNA construct or vector into a host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated micro-projectiles and protoplast fusion. General transformation techniques are well known in the art (see, e.g., Ausubel et al., 1987, Sambrook et al., 2001 and Campbell et al., 1989). Likewise, methods known in the art may be used to select transformants.

In certain other embodiments, a transgalactosylating polypeptide composition may be prepared in accordance with methods known in the art, and may be in the form of a liquid or a dry composition. For instance, the polypeptide composition may be in the form of a granulate, or a microgranulate, wherein the polypeptide in the composition may be stabilized in accordance with methods well known in the art.

III. Genetically Modified *Bacillus* Cells Deficient in P-Nitrobenzylesterase Activity As set forth above, certain embodiments of the disclosure are directed to genetically modified host cells expressing/producing β-galactosidase and/or lactase enzymes, and the use of such enzymes or cells thereof for the production of galactooligosaccharide (GOS) compositions in one or more dairy related end products. More specifically, certain embodiments are directed to expressing/producing such β-galactosidase and/or lactase enzymes in modified *Bacillus* spp. host cells, wherein such enzymes produced and/or purified from the modified *Bacillus* host cells are free of unwanted/undesirable p-nitrobenzylesterase activity. For example, as presented in the Example section below, Applicants of the instant disclosure have experimentally verified that a foul off-flavor smell and taste in dairy products formulated with 0-galactosidase and/or lactase enzymes were caused by the unwanted/undesirable enzymatic side activity of a p-nitrobenzylesterase enzyme.

More particularly, the nucleic acid sequence presented in SEQ ID NO: 1 encodes a p-nitrobenzylesterase enzyme presented in SEQ ID NO: 2, which encoded p-nitrobenzylesterase enzyme was originally identified in *B. subtilis* as an enzyme capable of hydrolyzing poly(ethylene terephthalate; PET), which may have specific utility in breaking down/hydrolyzing PET polymers in recycled materials (e.g., see, Ribitsch et al., 2011). Furthermore, as presented in Example 2, deletion of the gene encoding the p-nitrobenzylesterase (SEQ ID NO: 2) in a (modified) *Bacillus subtilis* (daughter) host cell expressing/producing a β-galactosidase of the disclosure, completely eliminated the detectable p-nitrobenzylesterase side activity identified in β-galactosidase compositions produced by the un-modified (parental) *Bacillus* cells.

Thus, in certain embodiments, a *Bacillus* spp. host cell of the disclosure is genetically modified to delete, disrupt or down-regulate an endogenous gene encoding a p-nitrobenzylesterase. In certain embodiments, a *Bacillus* spp. gene encoding a p-nitrobenzylesterase encodes a p-nitrobenzylesterase comprising at least about 60% to 100% amino acid sequence identity to the p-nitrobenzylesterase of SEQ ID NO: 2. In other embodiments, a *Bacillus* spp. gene encoding a p-nitrobenzylesterase encodes a p-nitrobenzylesterase comprising at least about 70% amino acid sequence identity to the p-nitrobenzylesterase of SEQ ID NO: 2. In another embodiment, a *Bacillus* spp. gene encoding a p-nitrobenzylesterase encodes a p-nitrobenzylesterase comprising at least about 80% amino acid sequence identity to the p-nitrobenzylesterase of SEQ ID NO: 2. In certain other embodiments, a *Bacillus* spp. gene encoding a p-nitrobenzylesterase encodes a p-nitrobenzylesterase comprising at least about 90% amino acid sequence identity to the p-nitrobenzylesterase of SEQ ID NO: 2. In yet other embodiments, a *Bacillus* spp. gene encoding a p-nitrobenzylesterase encodes a p-nitrobenzylesterase comprising about 100% amino acid sequence identity to the p-nitrobenzylesterase of SEQ ID NO: 2.

For example, the *Bacillus subtilis* pnbA gene (SEQ ID NO: 1) encodes a 489 amino acid p-nitrobenzylesterase (SEQ ID NO: 2, FIG. 13; Enzyme Commission No. 3.1.1.3) comprising a pI of about 4.8 and a molecular weight of about 53 kDa. More particularly, primary (1°) amino acid sequence analysis of the p-nitrobenzylesterase of SEQ ID NO: 2 (e.g., see, FIG. 13) identifies this enzyme as a member of the α/β hydrolase superfamily, wherein the catalytic apparatus involves a three residue catalytic triad comprising: serine (Ser), glutamate (Glu) or aspartate (Asp) and histidine (His), and comprises an acetyl esterase (AES) domain therein from about amino acid residue position 85 to 211 of SEQ ID NO: 2.

Thus, in certain embodiments, a genetically modified *Bacillus subtilis* host cell comprises modified endogenous gene encoding a p-nitrobenzylesterase comprising at least 60% sequence identity to the p-nitrobenzylesterase of SEQ ID NO: 2, wherein the gene encoding the p-nitrobenzylesterase comprises a genetic modification which deletes, disrupts or down-regulates at least the acetyl esterase domain of the encoded p-nitrobenzylesterase. In certain other embodiments, a genetically modified *Bacillus subtilis* host cell comprises a modified endogenous gene encoding a p-nitrobenzylesterase comprising at least 60% sequence identity to the p-nitrobenzylesterase of SEQ ID NO: 2, wherein the gene encoding the p-nitrobenzylesterase comprises a genetic modification which deletes, disrupts or substitutes at least one of the catalytic triad amino acids selected from serine (Ser), glutamate (Glu) or aspartate (Asp) and histidine (His). In other embodiments, the gene encoding the p-nitrobenzylesterase comprises a genetic modification which deletes, disrupts or substitutes at least two of the catalytic triad amino acids selected from serine (Ser), glutamate (Glu) or aspartate (Asp) and histidine (His). In yet other embodiments, the gene encoding the p-nitrobenzylesterase comprises a genetic modification which deletes, disrupts or substitutes all three of the catalytic triad amino acids serine (Ser), glutamate (Glu) or aspartate (Asp) and histidine (His). For example, the *B. subtilis* p-nitrobenzylesterase of SEQ ID NO: 2 comprises a catalytic triad comprising Ser-189, Glu-310 and 399-His.

In other embodiments, a genetically modified *Bacillus subtilis* host cell comprises a modified endogenous gene encoding a p-nitrobenzylesterase comprising at least 60% sequence identity to the p-nitrobenzylesterase of SEQ ID NO: 2, wherein the gene encoding the p-nitrobenzylesterase comprises a genetic modification which deletes, disrupts or down-regulates the acetyl esterase domain of the encoded p-nitrobenzylesterase. Thus, in certain embodiments, a gene encoding a p-nitrobenzylesterase comprising at least 60% sequence identity to the p-nitrobenzylesterase of SEQ ID NO: 2 comprises a genetic modification which deletes, disrupts or down-regulates the acetyl esterase (AE) domain of the encoded p-nitrobenzylesterase, wherein the AE domain comprises amino acid residue positions 85 to 211 of SEQ ID NO: 2. For example, in certain embodiments, the AE domain of a p-nitrobenzylesterase is down-regulated by means of anti-sense RNA methodology (e.g., an RNA molecule complementary to the endogenous gene encoding amino acid residue positions 85-211 (or a sub-sequence thereof) of p-nitrobenzylesterase), wherein the complementary RNA molecule down-regulates the expression/production of the p-nitrobenzylesterase in the modified host cell. In other embodiments, the genetically modified AE domain is deleted or disrupted, wherein the modified host cell exhibits reduced or eliminated p-nitrobenzylesterase thereof.

In other embodiments, a genetically modified *Bacillus subtilis* host cell comprises a modified endogenous gene encoding a p-nitrobenzylesterase comprising at least 60% sequence identity to the p-nitrobenzylesterase of SEQ ID NO: 2, wherein the modified gene encoding the p-nitrobenzylesterase comprises a genetic modification which deletes, disrupts or down-regulates the p-nitrobenzylesterase substrate binding pocket. For example, the p-nitrobenzylesterase of SEQ ID NO: 2 comprises a substrate binding pocket comprising thirteen (13) amino acid residue at positions 105-107, 188-190, 193, 326, 330, 331, 358, 400 and 403. In certain embodiments, amino acid residues 105-107 of SEQ ID NO: 2 comprise the motif "GGA" ($G_{105}$; $G_{106}$; $A_{107}$), which forms part of the substrate binding pocket. In other embodiments, amino acid residues 188-193 of SEQ ID NO: 2 comprise the motif "ESAXXM" ($E_{188}$, $S_{189}$, $A_{190}$, $X_{191}$, $X_{192}$, $M_{193}$; wherein X is any amino acid), which forms part of the substrate binding pocket. In another embodiment, amino acid residue 326 is threonine ($T_{326}$), which forms part of the substrate binding pocket, amino acid residue 330 is alanine ($A_{330}$), which forms part of the substrate binding pocket, amino acid residue 331 is leucine ($T_{331}$), which forms part of the substrate binding pocket, amino acid residue 358 is methionine ($M_{358}$), which forms part of the substrate binding pocket, amino acid residue 400 is alanine ($A_{400}$), which forms part of the substrate binding pocket and amino acid residue 403 is leucine ($T_{403}$), which forms part of the substrate binding pocket.

Thus, in certain embodiments, the nucleic acid sequence of SEQ ID NO: 1 (or a subsequence thereof), which encodes a *Bacillus subtilis* p-nitrobenzylesterase of SEQ ID NO: 2, is used to screen other *Bacillus* spp. host cells (e.g., *B. licheniformis, B. amyloliquefaciens*, and the like) for the presence of one or more genes encoding polypeptides comprising p-nitrobenzylesterase activity. For example, in certain embodiments, the disclosure is directed to genetically modified *Bacillus subtilis* host cells comprising a deleted, disrupted or down-regulated gene encoding a p-nitrobenzylesterase comprising at least 60% sequence identity to the p-nitrobenzylesterase of SEQ ID NO: 2. In certain other embodiments, the disclosure is directed to genetically modified *Bacillus amyloliquefaciens* host cells comprising a deleted, disrupted or down-regulated gene encoding a p-nitrobenzylesterase comprising about 483 to 484 amino acids and at least 62% sequence identity to the p-nitrobenzylesterase of SEQ ID NO: 2. In other embodiments, the disclosure is directed to genetically modified *Bacillus licheniformis* host cells comprising a deleted, disrupted or down-regulated gene encoding a p-nitrobenzylesterase comprising about 490 to 492 amino acids and at least 58% sequence identity to the p-nitrobenzylesterase of SEQ ID NO: 2.

For example, the *B. subtilis* p-nitrobenzylesterase of SEQ ID NO: 2 was BLAST-P searched in the NCBI non-redundant reference sequence database (data not shown), wherein more than twenty-eight (28) homologous *B. subtilis* p-nitrobenzylesterase proteins were identified with sequence identities to SEQ ID NO: 2 ranging from 100% to about 80%. Likewise, more than ten (10) homologous *B. amyloliquefaciens* p-nitrobenzylesterase proteins were identified with sequence identities to SEQ ID NO: 2 ranging from 62% to about 65% and wherein the encoded p-nitrobenzylesterase comprises about 483 to 484 amino acids. Furthermore, more than eight (8) *B. licheniformis* p-nitrobenzylesterase proteins were identified with sequence identities to SEQ ID NO: 2 ranging from 60% to about 65% and wherein the encoded p-nitrobenzylesterase comprises about 490 to 492 amino acids.

Thus, certain embodiments of the disclosure are directed to modified *Bacillus* sp. host cells comprising a deleted, disrupted or down-regulated p-nitrobenzylesterase protein comprising at least 60% sequence identity to the p-nitrobenzylesterase amino acid sequence of SEQ ID NO: 2. Related embodiments are therefore directed to expressing/producing β-galactosidases and/or lactases in the modified *Bacillus* host cells of the disclosure, wherein the β-galactosidases and/or lactases expressed/produced therefrom are free of detectable p-nitrobenzylesterase activity, thereby eliminating the foul off-flavor smells and tastes observed with dairy products contaminated with such p-nitrobenzylesterase side activity.

Thus, certain embodiments of the disclosure are directed to genetically modified *Bacillus* host cells capable of expressing/producing one or more β-galactosidases and/or lactases of the disclosure. For example, International PCT Publication No. WO2016/071504 discloses recombinant *Bacillus subtilis* host cells transformed with polynucleotide constructs (e.g., expression constructs) encoding various β-galactosidases. Thus, *Bacillus* host cells are well known in the art as expression hosts and are particularly suitable host cells for expressing/producing one or more β-galactosidases and/or lactases of the disclosure.

In certain embodiments, the disclosure is therefore directed to methods for genetically modifying *Bacillus* cells, wherein the modification comprises (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) a gene down-regulation, (f) site specific mutagenesis and/or (g) random mutagenesis.

Thus, a modified *Bacillus* cell of the disclosure is constructed by reducing or eliminating the expression of a p-nitrobenzylesterase gene set forth above, using methods well known in the art, for example, insertions, disruptions, replacements, deletions, truncations, substitutions, frame shift mutations and the like. The portion of the p-nitrobenzylesterase gene to be modified or inactivated may be, for example, the coding region or a regulatory/control element required for expression of the coding region.

An example of such a regulatory or control sequence may be a promoter sequence or a functional part thereof, (i.e., a part which is sufficient for affecting expression of the nucleic acid sequence). Other control sequences for modification include, but are not limited to, a leader sequence, a propeptide sequence, a signal sequence, a transcription terminator, a transcriptional activator and the like.

In certain other embodiments a modified *Bacillus* cell is constructed by gene deletion to eliminate or reduce the expression of the p-nitrobenzylesterase gene. Gene deletion techniques enable the partial or complete removal of the gene(s), thereby eliminating their expression, or expressing a non-functional (or reduced activity) protein product. In such methods, the deletion of the gene may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art (e.g., by reference to the p-nitrobenzylesterase gene's (nucleic acid) sequence and the encoded protein sequence thereof), may readily identify nucleotide regions in the gene's coding sequence and/or the gene's non-coding sequence suitable for complete or partial deletion.

In other embodiments, a modified *Bacillus* cell of the disclosure is constructed by introducing, substituting, or removing one or more nucleotides in the gene or a regulatory element required for the p-nitrobenzylesterase transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990). Thus, in certain embodiments, a p-nitrobenzylesterase gene of the disclosure is inactivated by complete or partial deletion.

In another embodiment, a modified *Bacillus* cell is constructed by the process of gene conversion (e.g., see Iglesias and Trautner, 1983). For example, in the gene conversion method, a nucleic acid sequence corresponding to the gene is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* cell is constructed by established anti-sense techniques using a nucleotide sequence complementary to the nucleic acid sequence of the p-nitrobenzylesterase gene (Parish and Stoker, 1997). More specifically, expression of the p-nitrobenzylesterase gene by a *Bacillus* cell may be reduced (down-regulated) or eliminated by introducing a nucleotide sequence complementary to the nucleic acid sequence of the p-nitrobenzylesterase gene, which may be transcribed in the cell and is capable of hybridizing to the p-nitrobenzylesterase mRNA produced in the cell. Under conditions allowing the complementary anti-sense nucleotide sequence to hybridize to the mRNA, the amount of p-nitrobenzylesterase protein translated is thus reduced or eliminated. Such anti-sense methods include, but are not limited to RNA interference (RNAi), small interfering RNA (siRNA), microRNA (miRNA), anti-sense oligonucleotides, and the like, all of which are well known to the skilled artisan.

In other embodiments, a modified *Bacillus* cell is produced/constructed via CRISPR-Cas9 editing. For example, a gene encoding p-nitrobenzylesterase can be disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the p-nitrobenzylesterase gene are readily identified by a person skilled in the art. For example, to build a DNA construct encoding a gRNA-directed to a target site within the gene of interest, the variable targeting (VT) domain will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In yet other embodiments, a modified *Bacillus* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the p-nitrobenzylesterase gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the p-nitrobenzylesterase gene.

In other embodiments, a modified *Bacillus* cell comprises a disruption of an endogenous p-nitrobenzylesterase gene, wherein the polynucleotide disruption cassette comprises a marker gene.

PCT Publication No. WO2003/083125 discloses methods for modifying *Bacillus* cells, such as the creation of *Bacillus* deletion strains and DNA constructs using PCR fusion to bypass *E. coli*.

PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus* sp.) (e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Thus, in certain embodiments, a suitable *Bacillus* host cell of the disclosure includes, but is not limited to, *Bacillus subtilis, B. licheniformis, B. lentus, B. brevis, B. stearothermophilus, B. alkalophilus, B. amyloliquefaciens, B. coagulans, B. circulars. B. lautus* and *B. thuringiensis*. In one particular embodiment, the *Bacillus* host cell is a *B. subtilis* host cell, a *B. licheniformis* host cell or a *B. amyloliquefaciens* host cell.

In certain other embodiments, expressing/producing such β-galactosidase and/or lactase enzymes in genetically modified *Bacillus* host cells (i.e., *Bacillus* host cells comprising a deletion, disruption or down-regulation of a gene encoding a p-nitrobenzylesterase), wherein such enzymes produced and purified from the modified *Bacillus* host cells are free of unwanted/undesirable enzymatic side activities including, but not limited to, unwanted/undesirable p-nitrobenzylesterase side activity, unwanted/undesirable lipase side activities, phospholipase side activities, cellulase side activities, pectinase side activities, amylase side activities, protease side activities, mannanase side activities and the like. For example, in certain embodiments the disclosure is directed to genetically modified *Bacillus* host cells comprising a deletion, disruption or down-regulation of a gene encoding at least one additional unwanted/undesirable enzymatic activity selected from a cellulase, a mannanase, a pectinase, an amylase, a protease, a lipase and/or a phospholipase side activity.

For example, modified *Bacillus* host cells in which these enzymes are essentially inactive may be obtained by genetic modification using recombinant genetic manipulation techniques as generally set forth above with respect to the p-nitrobenzylesterase activity. Modification of the genes coding for a cellulase, a mannanase, a pectinase, an amylase, a protease, a lipase, and/or a phospholipase can be generated by subjecting the parent *Bacillus* cell to mutagenesis and selecting for mutant *Bacillus* cells in which the ability to express these enzymes has been reduced by direct comparison to the parental *Bacillus* cell. The mutagenesis, which may be specific or random, may be performed, for example, by use of a suitable physical or chemical mutagenizing agent, by use of a suitable oligonucleotide, by use of CRSIPR/Cas9 editing, or by subjecting the DNA sequence to PCR-generated mutagenesis. Furthermore, the mutagenesis may be performed by use of any combination of these mutagenizing agents.

The cellulase, mannanase, pectinase, amylase, protease, lipase, and/or phospholipase deficient host cell may be selected by monitoring the expression level of the enzyme(s). Optionally, the cellulase, mannanase, pectinase, amylase, protease, lipase and/or phospholipase deficient host cell may be subsequently selected by measuring the expression level of a given gene of interest to be expressed (e.g., a β-galactosidase/lactase enzyme of the disclosure) in the host cell. Selection of host cells having reduced enzyme activity may be done by directly measuring the enzyme activity in culture broth, in culture supernatant, in permeabilized cells, or cell lysate.

Alternatively, host cells that have a reduced amount of lipase, phospholipase, cellulase, pectinase, amylase, protease, mannanase side activities (or a host cell in which these enzymes are essentially inactive) may be constructed using recombinant DNA technology. Several techniques for gene inactivation or gene disruption are described in the art, such as one-step gene disruption, marker insertion, site directed mutagenesis, deletion, RNA interference, anti-sense RNA, CRSIPS/Cas9 gene editing, TALEN gene editing, meganucleases (homing endonuclease) editing and others, and may all be used to lower, inhibit, disturb or prevent the synthesis of the lipase, phospholipase, cellulase, pectinase, amylase, protease and/or mannanase activity in order to obtain an industrial production strain with decreased lipase, phospholipase, cellulase, pectinase, amylase, protease and/ or mannanase activity. Also, the inactivation of lipase, phospholipase, cellulase, pectinase, amylase, protease and/or mannanase activity by altering the control sequence(s) directing the expression of the lipase, phospholipase, cellulase, pectinase, amylase, protease and/or mannanase gene are part of the present invention. For example, methods such as gene disruption are readily available and useful for lowering or eliminating promoter activity.

Thus, in certain embodiments, the genome of a host cell of the disclosure is modified to be deficient in lipase, phospholipase, cellulase, pectinase, amylase, protease and/or mannanase activity (e.g., by inserting a "marker gene" into a gene coding for the enzyme activity). Thus, in certain embodiments, the inserted marker gene replaces part of the gene coding for the enzyme from the genome (e.g., 25%, 50% or 75% of the gene) or all of the gene coding for the enzyme from the genome.

Methods to perform such gene inactivation have been described for many different micro-organisms and are known to those skilled in the art. Expression of lipase, phospholipase, cellulase, pectinase, amylase, protease and/or mannanase in the modified host cell may thereby be reduced or eliminated. Dependent on the particular host cell that is modified using these techniques, the procedure may be repeated several times to remove all or most of the lipase, phospholipase, cellulase, pectinase, amylase, protease and/or mannanase coding sequences.

Modification or inactivation of host genes such as lipase, phospholipase, cellulase, pectinase, amylase, protease and/or mannanase may be performed by established antisense techniques using a nucleotide sequence complementary to the nucleotide sequence of the gene. Likewise, modification of a host cell gene may be obtained via RNA interference (RNAi) techniques (FEMS Microb. Lett. 237:317-324, 2004). More specifically, expression of the gene by a *Bacillus* host cell may be reduced or eliminated by cloning identical sense and antisense portions of the nucleotide sequence, which expression is to be affected, behind each other with a nucleotide spacer in between, inserting into an expression vector, and introducing the expression vector into the cell where double-stranded RNA (dsRNA) may be transcribed and then processed to shorter siRNA that is able to hybridize to target mRNA. After dsRNA is transcribed, formation of small (21-23) nucleotide siRNA fragments will lead to a targeted degradation of the mRNA, which is to be affected. The elimination of the specific mRNA can be to various extents. The RNA interference techniques described in PCT Publication NOs: WO 2005/05672 and WO 2005/026356 may be used for modification of the host gene.

Thus, in certain embodiments, a modified host cell of the disclosure comprising decreased lipase, phospholipase, cellulase, pectinase, amylase, protease and/or mannanase activity is constructed by classical genetic techniques or recombinant DNA technology. In certain preferred embodiments, these modified host cells are used for the production of the industrially relevant enzymes having transgalactosylating activity. More preferably these modified host cells are used for the production of enzymes that are used in the food industry, even more preferably these enzymes are used in processing of dairy products. Most preferably, such industrial production host cells with decreased lipase, phospholipase, cellulase, pectinase, amylase, protease and/or mannanase activity are used for the production of galactooligosaccharides (GOS) from lactose substrates.

Thus, in certain embodiments, the lipase, phospholipase, cellulase, pectinase, amylase, protease and/or mannanase deficient host cells of the invention are modified host cells having less than 50% of the detectable intracellular or extracellular lipase, phospholipase, cellulase, pectinase, amylase, protease and/or mannanase activity as generally described in International PCT Publication No. WO2016/071504. More preferably, in other embodiments, the lipase, phospholipase, cellulase, pectinase, amylase, protease and/or mannanase deficient host cells of the disclosure are modified host cells having less than 50% of the lipase, phospholipase, cellulase, pectinase, amylase, protease and/or mannanase activity. In another embodiment, the lipase, phospholipase, cellulase, pectinase, amylase, protease and/or mannanase deficient host cells of the disclosure are modified host cells having lipase, phospholipase, cellulase, pectinase, amylase, protease and/or mannanase activity, which is less than 25% of the lipase, phospholipase, cellulase, pectinase, amylase, protease and/or mannanase activity of the unmodified (parental) host cell. In another embodiment, less than 10%, more preferably less than 5%, more preferably less than 1% and most preferably the lipase, phospholipase, cellulase, pectinase, amylase, protease and/or mannanase activity is undetectable in the deficient (i.e., genetically modified) host cells of the invention.

A variety of systems and methods for the detection of polypeptides/enzymes are known to the skilled artisan. Detection systems include any possible assay for detection of polypeptide or enzymatic activity. By way of example, these assay systems include, but are not limited to, assays based on colorimetric, photometric, fluorometric, turbidimetric, viscosimetric, immunological, biological, chromatographic and other available assays. In certain embodiments, the amount of active enzyme produced e.g., an active lipase, phospholipase, cellulase, pectinase, amylase, protease and/or mannanase) is determined by measurement of its activity in a model reaction.

In certain other embodiments, the lipase, phospholipase, cellulase, pectinase, amylase, protease and/or mannanase deficient (i.e., modified) host cell of the disclosure is characterized by the fact that when modified host cell has been transformed with an expression construct comprising a gene coding for a polypeptide having transgalactosylating activity, the modified host cell produces at least the same amount of the polypeptide that the unmodified (parental) host cell produces under the same culture conditions, when the unmodified (parental) host cell has also been transformed with the same expression construct as the lipase, phospholipase, cellulase, pectinase, amylase, protease and/or mannanase deficient modified host cell. In preferred embodiments, lipase, phospholipase, cellulase, pectinase, amylase, protease and/or mannanase deficient host cells of the disclosure are modified host cells that produce the same amount or more of the polypeptide having transgalactosylating activity than the unmodified (parental) host cell under the same culture conditions. In certain embodiments, the lipase, phospholipase, cellulase, pectinase, amylase, protease and/or mannanase deficient host cells produce more of a given polypeptide than the unmodified (parental) host cell under the same culture conditions.

IV. β-Galactosidase Polynucleotides and Vectors Thereof

In certain embodiments, the present disclosure employs isolated polypeptides having transgalactosylating activity, as described above, which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) a nucleic acid sequence comprised in SEQ ID NO: 3, 5, 7, 9, 11, 13, 15 or 25, encoding a mature polypeptide of SEQ ID NO: 4, 6, 8, 10, 12, 15, 16 or 26, (ii) the cDNA sequence of (i), or (iii) the complementary strand of (i) or (ii). In certain embodiments, a subsequence of SEQ ID NO: 3, 5, 7, 9, 11, 13, 15 or 25 contains at least 100 contiguous nucleotides, or at least 200 contiguous nucleotides. Moreover, the subsequence may encode a polypeptide fragment which has lactase or transgalactosylase activity.

The nucleotide sequence of SEQ ID NO: 3, 5, 7, 9, 11, 13, 15 or 25 (or a subsequence thereof), as well as the amino acid sequence of SEQ ID NO: 4, 6, 8, 10, 12, 14, 16 or 26 (or a fragment thereof), may be used to design a nucleic acid probe to identify and clone DNA encoding polypeptides having transgalactosylase activity from strains of different genera or species, according to methods well known in the art.

In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, a nucleic acid probe may be at least 200 nucleotides, preferably at least 300 nucleotides, more preferably at least 400 nucleotides, or most preferably at least 500 nucleotides in length. Even longer probes may be used (e.g., nucleic acid probes which are at least 600 nucleotides, at least preferably at least 700 nucleotides, more preferably at least 800 nucleotides, or most preferably at least 900 nucleotides in length). Both DNA and RNA probes can be used. The probes are typically labeled for detecting the corresponding gene (for example, with 32P, 3H, 35S, biotin, or avidin). Such probes are encompassed by the present invention.

A genomic DNA library prepared from such organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 3, 5, 7, 9, 11, 13, 15 or 25 (or a subsequence thereof), the carrier material is used in a Southern blot.

For purposes of the present disclosure, hybridization indicates that the nucleotide sequence hybridizes to a labelled nucleic acid probe corresponding to the nucleotide sequence shown in SEQ ID NO: 3, 5, 7, 9, 11, 13 or 15, its complementary strand, or a subsequence thereof, under very low to very high stringency conditions. Molecules to which the nucleic acid probe hybridizes under these conditions can be detected using X-ray film.

The nucleic acid probe may be the mature polypeptide coding region of SEQ ID NO: 3, 5, 7, 9, 11, 13, 15 or 25.

For long probes of at least 100 nucleotides in length, very low to very high stringency conditions are defined as pre-hybridization and hybridization at 42° C. in 5×SSPE, 0.3% SDS, 200 g/ml sheared and denatured salmon sperm DNA, and either 25% formamide (for very low and low stringencies), 35% formamide (for medium and medium-high stringencies), or 50% formamide (for high and very high stringencies), following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In certain embodiments, the wash is conducted using 0.2 SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as pre-hybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl (pH 7.6), 6 mM EDTA, 0.5% NP-40, 1×Denhardt's solution, 1 mM sodium pyrophosphate, 1 mM sodium monobasic phosphate, 0.1 mM ATP and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[Na+]) + 0.41(\% \, G+C) - 0.72(\% \text{ formamide}).$$

Thus, variant nucleic acids of the disclosure include a polynucleotide having a certain percent (e.g., 60%, 65%, 70%, 75%, 80%, 85%, 90%, 95%, or 99%) of sequence identity with the nucleic acid encoding SEQ ID NO: 4, 6, 8, 10, 12, 15, 16 or 26. In certain embodiments, a nucleic acid capable of encoding a polypeptide as disclosed herein is provided. In other embodiments, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 3, 5, 7, 9, 11, 13, 15 or 25.

In certain embodiments, the disclosure provides a plasmid comprising a nucleic acid encoding a β-galactosidase and/or lactase polypeptide of the disclosure. In certain other embodiments, the disclosure provides an expression vector comprising a nucleic acid encoding a β-galactosidase and/or lactase polypeptide of the disclosure.

Thus, in particular embodiments the β-galactosidase and/or lactase polypeptides (and variants thereof) described herein are produced through recombinant expression in a host cell according to procedures well known in the art. More particularly, in certain embodiments the β-galactosidase and/or lactase polypeptides (and variants thereof) as described herein are expressed/produced in a modified *Bacillus* host cell comprising at least a disruption or deletion of a gene encoding a p-nitrobenzylesterase comprising at least 60% sequence identity to SEQ ID NO: 2.

Methods of genetic modification and recombinant production of polypeptides are described, for example, in U.S. Pat. Nos. 7,371,552, 7,166,453, 6,890,572 and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888 and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

In certain embodiments, the instant disclosure is directed to one or more vectors comprising a polynucleotide encoding a protein of interest. In certain preferred embodiments, such proteins of interest include β-galactosidase/lactase polypeptides, such as the β-galactosidase/lactase polypeptides set forth as SEQ ID NOs: 4, 6, 8, 10, 12, 14, 16, 17, 18 or 26. Thus, in certain other embodiments, a recombinant host cell of the disclosure comprises one or more vectors introduced therein. In certain other embodiments, a polynucleotide/DNA construct encoding a β-galactosidase/lactase polypeptide of the disclosure is introduced into a host cell as an "expression vector", which vector comprises regulatory sequences (e.g., a promoter sequence, a terminator sequence, 5'UTRs, 3'UTRs and the like) operably linked to the β-galactosidase and/or lactase encoding sequence. More particularly, in certain embodiments, an expression vector comprising a nucleic acid sequence encoding a β-galactosidase/lactase polypeptide of the disclosure is introduced into a genetically modified host cell (e.g., a *Bacillus* cell), which genetically modified host cell comprises at least a deletion, disruption or down-regulation of a gene encoding a p-nitrobenzylesterase comprising at least 60% sequence identity to SEQ ID NO: 2.

Exemplary vectors include, but are not limited to, pBR322 and pUC19, which permit replication in *E. coli*, and pE194, which permits replication in *Bacillus*.

In certain embodiments, a nucleic acid encoding a β-galactosidase/lactase polypeptide of the disclosure is operably linked to a suitable promoter, which allows transcription in the host cell. For example, the promoter may be derived from genes encoding proteins either homologous or heterologous to the host cell. Promoters and promoter sequence regions for use in the expression of genes, open reading frames (ORFs) thereof and/or variant sequences thereof in *Bacillus* cells are generally known to one of skill in the art. Promoter sequences of the disclosure are generally chosen so that they are functional in the *Bacillus* cells (e.g., *B. licheniformis* cells, *B. subtilis* cells and the like). Certain exemplary *Bacillus* promoter sequences include, but are not limited to, the *B. subtilis* alkaline protease (aprE) promoter, the a-amylase promoter of *B. subtilis*, the a-amylase promoter of *B. amyloliquefaciens*, the neutral protease (nprE) promoter from *B. subtilis*, a mutant aprE promoter (PCT Publication No. WO2001/51643) or any other promoter from a related Bacilli. In certain other embodiments, the promoter is a ribosomal protein promoter or a ribosomal RNA promoter (e.g., the rrnI promoter) disclosed in U.S. Patent Publication No. 2014/0329309. Methods for screening and creating promoter libraries with a range of activities (promoter strength) in *Bacillus* cells is describe in PCT Publication No. WO2003/089604. In certain embodiments, the promoter is native to the *Bacillus* host cell, whereas in other embodiments the promoter is heterologous (foreign) to the *Bacillus* host cell.

In other embodiments, a polynucleotide sequence (e.g., comprised in a vector/expression construct) encoding a β-galactosidase/lactase polypeptide is operably linked to a nucleic acid sequence encoding a signal sequence (signal peptide). Thus, in certain embodiments, a nucleic acid sequence encoding a signal sequence is derived *B. bifidum* or a *Bacillus* spp. In certain other embodiments, the native signal sequence of *B. subtilis* aprE is used, or alternatively, a nucleotide sequence encoding a signal sequence from other *Bacillus* spp. secreted proteins. Thus, in certain embodiments, the polynucleotide sequence that encodes the signal sequence is place immediately upstream (5') and in-frame of the polynucleotide (i.e., operably linked) that encodes the β-galactosidase/lactase polypeptide of the disclosure.

Thus, in certain other embodiments, the disclosure includes a signal sequence and a promoter sequence which are comprised in the vector to be introduced into the host cell. In other embodiments, the expression vector also includes a termination sequence. In certain embodiments, the termination sequence, the signal sequence and the promoter sequence are derived from the same source or different sources.

In certain other embodiments, an expression vector includes a selectable marker. Examples of suitable selectable markers include those that confer resistance to antimicrobial agents (e.g., hygromycin, phleomycin and the like) and nutritional selective (auxotrophic) markers.

Thus, a suitable expression vector comprising a DNA construct encoding a β-galactosidase/lactase polypeptide of the disclosure may be any vector that is capable of replicating autonomously in a *Bacillus* host cell, or integrating into the genome of the host cell.

VI. Production of β-Galactosidases/Lactases in Modified *Bacillus* Host Cells Deficient in Unwanted Enzymatic Side Activities In certain other embodiments, the present disclosure is directed to methods of transcribing a nucleotide sequence in a modified host cell deficient in (unwanted/undesirable) para-nitrobenzylesterase activity. In yet other embodiments, the present disclosure is directed to methods of transcribing a nucleotide sequence in a modified host cell deficient in para-nitrobenzylesterase activity, wherein the modified host cell is further engineered to be deficient is at least one additional (unwanted/undesirable) enzymatic activity selected from lipase, phospholipase, cellulase, pectinase, amylase, protease and/or mannanase activity, wherein the transcribed sequence encodes the polypeptide having transgalactosylating activity comprising cultivating, in a culture medium, the modified host cell of the disclosure comprising an expression construct encoding a transgalactosylating polypeptide of the disclosure.

For example, in certain embodiments, a modified host cell deficient in para-nitrobenzylesterase activity is (1) transformed with an expression construct comprising (a) a 5' promoter region upstream and operably linked to (b) a downstream nucleotide sequence (e.g., an ORF) which encodes a transgalactosylating polypeptide of the disclosure and (c) a translational stop signal which is 3' and operably linked to nucleic acid sequence encoding the transgalactosylating polypeptide and (2) expressing the transgalactosylating polypeptide in the modified host cell. In another embodiment, the transgalactosylating polypeptide expressed/produced in the modified host cell of the disclosure is recovered from the culture medium or from the modified host cell (e.g., via cell lysis).

The modified host cells deficient in deficient para-nitrobenzylesterase, lipase, phospholipase, cellulase, pectinase, amylase, protease and/or mannanase are produced according to the methods of the present disclosure. Thus, in certain embodiments, the deficient (modified) host cells are be grown or maintained in a nutrient medium suitable for production of the desired polypeptide using methods known in the art. For example, cells may be plated on a solid substrate, shaken in a flask, cultivated in small-scale or large-scale fermentation (including continuous, batch, fed-batch, or solid-state fermentation) in laboratory or industrial fermenters in a suitable medium and under conditions allowing the polypeptide to be expressed and/or isolated.

Cultivation takes place in a suitable nutrient medium comprising carbon and nitrogen sources and inorganic salts, using procedures known in the art. Suitable media are available from commercial suppliers or may be prepared using published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide(s) may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures well known in the art including, but not limited to, chromatography (e.g., ion exchange, affinity, hydrophobic, chromatofocusing or size exclusion), electrophoresis (e.g., preparative isoelectric focusing), differential solubility (e.g., acetone or ammonium sulfate precipitation), or extraction (e.g., chaotrope, salt, or pH).

The polypeptide may be detected using methods known in the art that are specific for a polypeptide having transgalactosylating activity. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes. More particularly, the disclosures of International PCT Publications NOs: WO2016/071504 and WO2015/086746, provide specific methods and compositions thereof for assaying polypeptide having transgalactosylating activity (e.g., β-galactosidases/lactases), which methods are incorporated herein by reference in their entirety. Thus, in certain embodiments, a polypeptide having transgalactosylating activity (i.e., as produced in a modified host cell of the disclosure) is assayed according to the methods and compositions set forth in International PCT Publications NOs: WO2016/071504 and WO2015/086746.

Thus, in certain other embodiments, the disclosure is directed to compositions and methods for expressing a transgalactosylating polypeptide as described herein, comprising obtaining a modified host cell of the disclosure (i.e., comprising at least a deletion, disruption or down-regulation of a gene encoding a para-nitrobenzylesterase), and expressing the transgalactosylating polypeptide in the modified host cell, and optionally purifying the transgalactosylating polypeptide. As set forth above, such transgalactosylating polypeptides expressed/produced in the modified host cells of the disclosure are free of detectable para-nitrobenzylesterase activity, and as such, are particularly useful in the generation of galactooligosaccharide (GOS) compositions via lactose substrates. More particularly, as presented in the Examples section below, the expression/production of one or more transgalactosylating polypeptides in the modified host cells of the disclosure (i.e., comprising a deletion, disruption or down-regulation of the gene encoding the para-nitrobenzylesterase of SEQ ID NO: 2) produce such transgalactosylating polypeptides in the absence of the contaminating para-nitrobenzylesterase side activity, thereby eliminating the foul off-flavor tastes and smells detected when using such transgalactosylating polypeptides which are expressed/produced in unmodified (parental) host cells comprising the para-nitrobenzylesterase side activity. Likewise, in other embodiments, the modified host cells of the disclosure are further modified to be deficient in at least one additional unwanted/undesirable enzymatic side activity selected from lipase, phospholipase, cellulase, pectinase, amylase, protease and/or mannanase (e.g., see, WO2016/071504).

Thus, in certain embodiments, the introduction of an expression construct or vector into a host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated micro-projectiles and protoplast fusion. General transformation techniques are well known in the art (see, e.g., Ausubel et al., 1987, Sambrook et al., 2001, and Campbell et al., Curr. Genet. 16: 53-56 (1989). Likewise, methods known in the art may be used to select transformants.

In certain embodiments, the instant disclosure is directed to methods of producing transgalactosylating polypeptides in a modified host cell, comprising fermenting/cultivating the modified host cell. Fermentation methods well known in the art can be applied to ferment the modified (daughter) and unmodified (parental) *Bacillus* cells of the disclosure. In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a transgalactosylating polypeptide produced by a modified host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

VI. Exemplary Applications

Examples are given below of preferred uses of the host cells, polypeptides or polypeptide compositions of the disclosure. For example, in certain embodiments, the disclosure provides a method for producing a food product by treating a substrate comprising lactose with a transgalactosylating polypeptide or a polypeptide composition thereof as described herein. In another embodiment, the disclosure provides a method for producing a dairy product by treating a milk-based substrate comprising lactose with a transgalactosylating polypeptide or a polypeptide composition thereof as described herein. In another embodiment, the substrate comprising lactose is further treated with a hydrolyzing β-galactosidase.

The enzyme preparation, such as in the form of a food ingredient prepared according to the present disclosure, may be in the form of a solution or as a solid, depending on the use and/or the mode of application and/or the mode of administration. The solid form can be either as a dried enzyme powder or as a granulated enzyme.

In certain embodiments, an enzyme composition comprises at least 5%, such as, for example, 10%, 15%, 20%, 25%, 30%, 35%, 40%, 45%, 50% w/w of one or more transgalactosylating polypeptide(s) disclosed herein based on the total amount of polypeptides in the composition. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using an appropriate densiometic scanner such as for example the Bio-Rad Criterion system and the resulting picture is ensured to be in the dynamic range. The bands corresponding to any transgalactosylating polypeptide are quantified and the percentage of the polypeptides are calculated as: Percentage of polypeptide in question=polypeptide in question/(sum of all polypeptides exhibiting transgalactosylating activity)*100. The total number of polypeptides can be determined by western blotting using a polyclonal antibody with specificity to a β-galactosidase/lactase polypeptide of SEQ ID NO: 4, 6, 8, 10, 12, 14, 16, 17, 18 or 26, by methods know to a person skilled in the art.

Thus, in certain embodiments, a composition according to the present disclosure comprises one or more polypeptide(s) selected from the group consisting of a SEQ ID NO: 4, 6, 8, 10, 12, 14, 16, 17, 18 and 26.

In another embodiment, the disclosure provides an enzyme complex preparation comprising the enzyme complex according to the invention, an enzyme carrier and optionally a stabilizer and/or a preservative. In certain embodiments, the enzyme carrier is selected from the group consisting of glycerol or water. In another embodiment, the enzyme carrier does not comprise a polyol (e.g., glycerol, propylene glycol or sorbitol).

In another embodiment, the preparation/composition comprises a stabilizer. In certain embodiments, the stabilizer is selected from the group consisting of inorganic salts, polyols, sugars and combinations thereof. In certain embodiments the stabilizer is an inorganic salt such as potassium chloride. In another embodiment, the polyol is glycerol, propylene glycol, or sorbitol. In another embodiment, the stabilizer is not a polyol such as glycerol, propylene glycol, or sorbitol. In yet another embodiment, the stabilizer is a small-molecule carbohydrate, in particular any of several sweet-tasting ones such as glucose, galactose, fructose and saccharose.

In other embodiments, the preparation comprises a preservative. In one aspect, the preservative is methyl paraben, propyl paraben, benzoate, sorbate or other food approved preservatives or a mixture thereof.

In certain embodiments, the methods of the disclosure can be practiced with immobilized enzymes (e.g. an immobilized lactase or other GOS producing enzymes). The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents.

In certain embodiments, immobilization of the β-galactosidase/lactase is optimized by physical adsorption on to the inorganic support. Enzymes used to practice the instant disclosure can be immobilized in different media, including water, Tris-HCl buffer and phosphate buffered solution. The enzyme can be immobilized to any type of substrate (e.g., filters, fibers, columns, beads, colloids, gels, hydrogels, meshes and the like).

In another embodiment, a method for producing a dairy product by treating a milk-based substrate comprising lactose with a polypeptide or a polypeptide composition as described herein is provided. In a further aspect, a method for producing a dairy product by treating a milk-based substrate comprising lactose with a polypeptide having a relative transgalactosylation activity above 60%, such as above 70%, such as above 75% after 15 minutes of reaction, is provided. In one aspect, the relative transgalactosylation activity is above 3 after 30 minutes of reaction. In a further aspect, the relative transgalactosylation activity is above 6 after 30 minutes of reaction. In yet a further aspect, the relative transgalactosylation activity is above 12 after 30 minutes of reaction.

In another embodiment, a method is provided, wherein the treatment with a polypeptide or a polypeptide composition as described herein takes place at an optimal temperature for the activity of the enzyme. In a further aspect, the polypeptide or the polypeptide composition is added to the milk-based substrate at a concentration of 0.01-1000 ppm. In yet a further aspect, the polypeptide or the polypeptide composition is added to the milk-based substrate at a concentration of 0.1-100 ppm. In a further aspect, the polypeptide or the polypeptide composition is added to the milk-based substrate at a concentration of 1-10 ppm. In one aspect, a method further comprising fermenting a substrate such as a dairy product with a microorganism, is provided. In a further aspect, the dairy product is yogurt. In a further aspect, the treatment with the polypeptide or the polypeptide composition and the microorganism is performed essentially at the same time. In one aspect, the polypeptide or the polypeptide composition and the microorganism are added to the milk-based substrate essentially at the same time.

In one aspect, a dairy product comprising a cell or a polypeptide or a polypeptide composition as described herein is provided. In one aspect, the polypeptide or the polypeptide composition as defined herein is added in a concentration of 0.01-1000 ppm.

In one aspect, a dairy product comprising GOS formed in situ by a polypeptide or a polypeptide composition as defined herein is provided. In one aspect, a dairy product comprising a cell as defined herein is provided.

A dairy product as described herein may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components (e.g., vegetable components such as vegetable oil, vegetable protein, and/or vegetable carbohydrates). Dairy products may also comprise further additives such as enzymes, flavouring agents, microbial cultures such as probiotic cultures, salts, sweeteners, sugars, acids, fruit, fruit juices, or any other component known in the art as a component of, or additive to, a dairy product. In one embodiment of the disclosure, one or more milk components and/or milk fractions account for at least 50% (weight/weight), such as at least 70%, e.g., at least 80%, preferably at least 90%, of the dairy product.

In one embodiment of the disclosure, one or more milk-based substrates having been treated with an enzyme as defined herein having transgalactosylating activity account for at least 50% (weight/weight), such as at least 70%, e.g. at least 80%, preferably at least 90%, of the dairy product.

In another embodiment of the disclosure, the dairy product is a dairy product which is not enriched by addition of pre-produced galactooligosaccharides (GOSs).

In another embodiment of the disclosure, the polypeptide-treated milk-based substrate is not dried before being used as an ingredient in the dairy product.

In another embodiment of the disclosure, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In another embodiment of the disclosure, the dairy product is milk or condensed milk.

In yet another embodiment of the disclosure, the dairy product is ultra-high temperature (UHT) milk. UHT milk in the context of the present disclosure is milk which has been subjected to a sterilization procedure which is intended to kill all microorganisms, including the bacterial spores. Thus, UHT treatment includes a heat treatment for 30 seconds at 130° C., or heat treatment for one second at 145° C.

In another embodiment of the disclosure, the dairy product is ESL milk. ESL milk in the present context is milk which has an extended shelf life due to microfiltration and/or heat treatment, and which is able to stay fresh for at least 15 days, preferably for at least 20 days, on the store shelf at 2-5° C. In another embodiment of the disclosure, the dairy product is a fermented dairy product (e.g., yoghurt).

The microorganisms used for most fermented milk products are selected from the group of bacteria generally referred to as "lactic acid" bacteria. As used herein, the term "lactic acid bacterium" designates a gram-positive, microaerophilic or anaerobic bacterium, which ferments sugars with the production of acids, including lactic acid as the predominantly produced acid, acetic acid and propionic acid. The industrially most useful lactic acid bacteria are found within the order "Lactobacillales", which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria (i.e *Bifidobacterium* spp.), which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40° C. to about 45° C. Typical organisms belonging to the mesophilic group include *Lactococcus lactis, Lactococcus lactis* subsp. *cremoris, Leuconostoc mesenteroides* subsp. *cremons, Pseudoleuconostoc mesenteroides* subsp. *cremoris, Pediococcus pentosaceus, Lactococcus lactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*.

Also the anaerobic bacteria belonging to the genus *Bifidobacterium* including *Bifidobacterium bifidum, Bifido-* bacterium animalis and *Bifidobacterium longum* are commonly used as dairy starter cultures and are generally included in the group of lactic acid bacteria. Additionally, species of Propionibacteria are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir*, Saccharomyces *kefir* and *Saccharomyces cerevisiae.*

In one embodiment of the present disclosure, the microorganism used for fermentation of the milk-based substrate is *Lactobacillus casei* or a mixture of *Streptococcus thermophilus* and *Lactobacillus delbrueckii* subsp. *bulgaricus.*

Fermentation processes to be used in a method of the present disclosure are well known and the person of skill in the art will know how to select suitable process conditions, such as temperature, oxygen, amount and characteristics of microorganism, additives such as carbohydrates, flavors, minerals, enzymes, and process time. Obviously, fermentation conditions are selected so as to support the achievement of the present disclosure.

As a result of fermentation, pH of the milk-based substrate will be lowered. The pH of a fermented dairy product of the disclosure may be in the pH range 3.5-6, such as in the pH range 3.5-5, preferably in the pH range 3.8-4.8.

Thus, certain embodiments of the disclosure are related to methods of using the polypeptides or the polypeptide compositions or using any one or more of the above mentioned modified host cell types for producing oligosaccharides are provided. The oligosaccharides comprise, but are not limited to fructo-oligosaccharides, galacto-oligosaccharides, isomalto-oligosaccharides, malto-oligosaccharides, lactosucrose and xylooligosaccharides.

In certain embodiments, the oligosaccharides are produced by incubating a modified host cell of the disclosure expressing the polypeptide in a medium that comprises a disaccharide substrate such as for example lactulose, trehalose, rhamnose, maltose, sucrose, lactose, or cellobiose. The incubation is carried out under conditions where oligosaccarides are produced. The cells may be part of a product selected from the group consisting of yoghurt, cheese, fermented milk products, dietary supplements, and probiotic comestible products. Alternatively, the oligosaccharides can be recovered and subsequently be added to the product of interest before or after its preparation.

In certain embodiments, the use of a herein disclosed modified host cell for producing a product selected from the group consisting of yoghurt, cheese, fermented milk product, dietary supplement and probiotic comestible product is provided.

In another embodiment, the use of a transgalactosylating polypeptide or a polypeptide composition as disclosed herein (or a cell as disclosed herein), for producing galactooligosaccharides (GOSs) is provided. In one aspect, the use of a transgalactosylating polypeptide or a polypeptide composition as disclosed herein or a cell as disclosed herein, for producing galactooligosaccharides to be part of a product selected from the group consisting of yoghurt, cheese, fermented dairy products, dietary supplements and probiotic comestible products is provided. In certain embodiments, the product is yoghurt, cheese, or a fermented dairy product. In another aspect, the use of a transgalactosylating polypeptide, or a polypeptide composition (or a modified host cell) as disclosed herein, for producing galactooligosaccharides to enhance the growth of *Bifidobacterium* are provided. In another aspect, the use of a transgalactosylating polypeptide or a polypeptide composition or modified host cell as disclosed herein for producing galactooligosaccharides to enhance the growth of *Bifidobacterium* in a mixed culture fermentation is provided.

In another aspect, a process for producing a transgalactosylating polypeptide or a polypeptide composition as disclosed herein, comprising culturing a modified host cell as disclosed herein in a suitable culture medium under conditions permitting expression of the polypeptide, and recovering the resulting polypeptide from the culture is provided. A process for producing galactooligosaccharides, comprising contacting a polypeptide or a polypeptide composition as disclosed herein or a cell as disclosed herein with a milk-based solution comprising lactose is provided.

Addition of oligosaccharides may enhance growth of either *Bifidobacterium* alone or of *Bifidobacterium* in a mixed culture.

In other embodiments, the transgalactosylating polypeptide or the polypeptide composition thereof is used together with other enzymes such as proteases, such as chymosin or rennin, lipases such as phospholipases, amylases, transferases, and lactases. In one aspect, the transgalactosylating polypeptide(s) as disclosed herein are used together with lactase. This may especially be useful when there is a desire to reduce residual lactose after treatment with the transgalactosylating polypeptide(s) as disclosed herein, especially at low lactose levels. In one embodiment, the enzyme is a lactase from a bacterium (e.g., from the family Bifidobacteriaceae), such as from the genus *Bifidobacterium* and the lactase described in International PCT Publication Nos: WO2009/071539 and WO2013/182686.

EXAMPLES

Certain aspects of the present invention may be further understood in light of the following examples, which should not be construed as limiting. Modifications to materials and methods will be apparent to those skilled in the art.

Example 1

Identification of Undesirable
Para-Nitrobenzylesterase Enzymatic Side Activity
in *Bacillus* Host Cells Producing β-Galactosidases
and Lactases Applicants of the present disclosure discovered a foul off flavor in yoghurt and UHT milk when formulating these dairy products with a β-galactosidase enzyme produced in a *Bacillus* host cell. For example, at day one (1) of the addition of the β-galactosidase enzyme to either a yoghurt product or UHT milk product, one (1) of four (4) people could detect the off flavor in the yoghurt, wherein the off flavor became significantly worse by day five (5). The off flavor characterization was consistent with a lipase activity rendering short chain free fatty acids (e.g. butyric acid) in the product.

Thus, to further evaluate the off flavor detected in these yoghurt and UHT milk products, material from a small-scale production of β-galactosidase in the *Bacillus* host cell was screened for lipase activity, wherein no lipase activity was detected. The lipase activity screen was generally performed as follows: after ten (10) minutes incubation at 37° C. of the glyceryl trioctanoate substrate with a lipase containing sample, the amount of the formed free fatty acids is determined by NEFA method. The principle of the NEFA C kit (MEGAZYME) is a three step reaction where free fatty acids are esterificated with co-enzyme A, and then oxidized under the formation of hydrogen peroxide. By enzymatic reaction, hydrogen peroxide causes a purple quinonimin coloring, wherein the $OD_{520\ nm}$ is read immediately after incubation. In addition, material "E" of the β-galactosidase produced in the *Bacillus* host (i.e., produced by small scale food grade fermentation and spray dried), passed sensory analysis in yoghurt, further indicating no risk of off flavor for the final product.

Several scenarios have been considered to explain the sudden detection of off-flavor in the end products (yoghurt and UHT milk). For example, the off-flavor could be a lipase contamination of the UFC in the β-galactosidase production, a lipase contamination during spray drying/blending, or a batch-to-batch variation of a lipase expressed from the host organism (*Bacillus subtilis*).

Qualitative Evaluation of Esterase/Lipase Side Activity

To further evaluate the off-flavor in the yoghurt and UHT milk products described above, several samples of spray dried β-galactosidase (i.e., originating from a full scale production of the β-galactosidase) were applied on a newly developed agar spot plate with 1% tributyrin, 1.5% lecithin, 0.05 M HEPES buffer (pH 7.4) with 0.01M $CaCl_2$ and phenol red. The lipase/phospholipase activity was detected as yellow haloes on the plates around the wells, wherein the three samples were all positively identified for lipase/phospholipase activity. Thus, the lipase/phospholipase activity detected in these samples indicated that the lipase/phospholipase activity was not a result of cross contamination from a lipase during spray drying, as the lipase/phospholipase activity was present in several independent batches. For example, the lipase activity in sample "C" was quantified to 0.41 LIPU/g using the LIPU-K (E117) analysis and correcting for sample blank value.

However, because phospholipases often comprise lipase activity, and the above assay used a mixture of lipase substrate (i.e., tributyrin) and phospholipase substrate (i.e., lecithin) in the spot plates, it was decided to test whether the samples were positive on a phospholipase substrate only spot plate assay (FIG. 1A). The sample did not test positive for phospholipase activity (as no haloes were visible around well "A" or "B" in FIG. 1A), having applied sample "C". Thus, this result indicated that the side activity was a triglyceride hydrolyzing lipase/esterase.

Figure 1B:
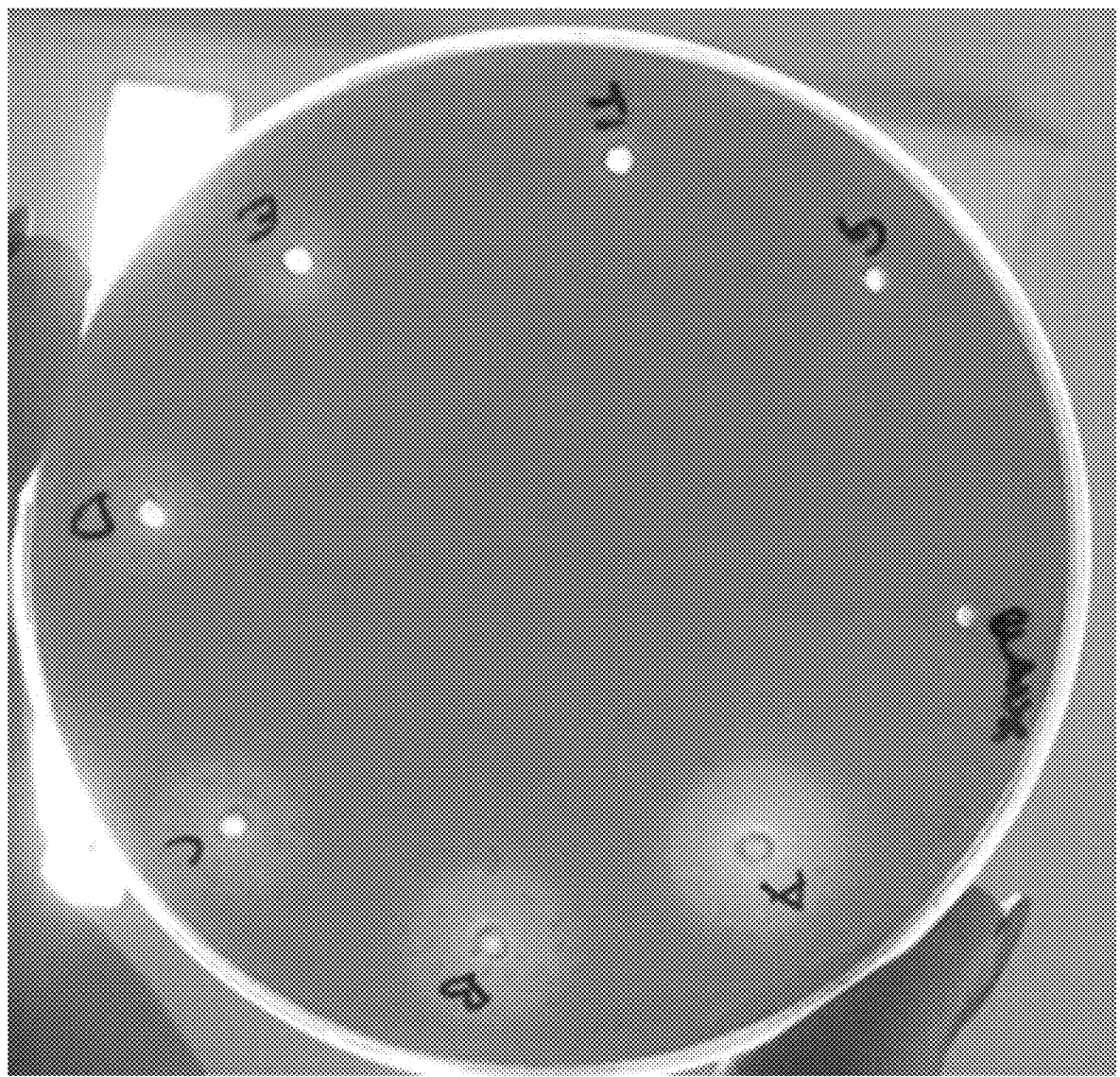
FIG. 1B shows the spot plate assay results using both a lipase substrate (i.e., tributyrin substrate) and a phospholipase substrate (i.e., lecithin substrate).

In addition, the sensitivity of the mixed substrate spot plates for this specific lipase enzyme activity present in the spray dried materials was tested. Several dilutions were performed on the sample "C", which was quantified as having 0.41 LIPU/g, and 104 of each dilution was applied on a mixed substrate spot plate (e.g., see TABLE 1 and FIG. 1B).

TABLE 1

LIPASE SENSITIVITY OF MIXED SUBSTRATE PLATES

| Well | Activity [Lipu/g] | Weighing [g] | Dilution [ml] | Conc. [Lipu/ml] | Loaded on gel [Lipu] | Result P or N |
|---|---|---|---|---|---|---|
| A | 0.41 | 1.0009 | 10 | 0.04100 | 0.00041 | positive |
| B | 0.41 | 1.0009 | 20 | 0.02050 | 0.00021 | positive |
| C | 0.41 | 1.0009 | 40 | 0.01025 | 0.00010 | positive |
| D | 0.41 | 1.0009 | 80 | 0.00513 | 0.00005 | positive |
| E | 0.41 | 1.0009 | 160 | 0.00256 | 0.00003 | positive |

TABLE 1-continued

LIPASE SENSITIVITY OF MIXED SUBSTRATE PLATES

| Well | Activity [Lipu/g] | Weighing [g] | Dilution [ml] | Conc. [Lipu/ml] | Loaded on gel [Lipu] | Result P or N |
|---|---|---|---|---|---|---|
| F | 0.41 | 1.0009 | 320 | 0.00128 | 0.00001 | negative |
| G | 0.41 | 1.0009 | 640 | 0.00064 | 0.00001 | negative |

Surprisingly, the sample could be diluted 160-fold and still detect a positive halo (see, FIG. 1B), although the sample only held 0.41 LIPU/g, indicating that detection of as little as 0.0026 LIPU/g in a solution was possible when applying 104 to the plate. Generally, it is not possible to detect less than 0.1 LIPU/g in the LIPU-k E117 method (data not shown). In comparison, this could indicate that the lipase/esterase activity detected in the samples favor the neutral pH and is specific towards short chain fatty acids, which are also known to result in a "cheese like" off-flavor in dairy applications.

Esterase Side Activity in Fermentation

Two (2) stabilized ultra-filtration concentrate (UFC) intermediates of β-galactosidase samples A and B produced in the *Bacillus* host were tested to confirm that the lipase activity was present in the UFC samples, and therefore did not come from a route of contamination while spray drying. For example, both UFC samples A and B originated from the same fermentation, and as such, both should comprise lipase activity, unless a contamination event occurred after the fermentation. More particularly, the powder 0-galactosidase materials which tested positive for lipase/esterase activity all originated from the sample A material. More specifically, the ferment had been split in two and stabilized after two different specifications, depending on the application it was intended to be used in. Specifications of A and B are presented below in Table 2.

TABLE 2

SAMPLE A AND SAMPLE B SPECIFICATIONS

| Sample A | Sample B |
|---|---|
| Activity: >1000 BLU/g | Activity: >1000 BLU/g |
| β-galactosidase/DS | β-galactosidase/DS |
| ratio: >6000 BLU/g DS | ratio: >2000 BLU/g DS |
| pH: 4.8-5.2 | pH: 6.3-6.7 |
| Potassium sorbate: 0.36-0.44% on final conc. (w/w) | NaCl: 20% on final conc. (w/w) |

Quantification of lipase activity (LIPU-k, E117) confirmed that both UFC materials had lipase side activity, indicating that the lipase side activity originates from the *Bacillus* production host cell. Additionally, the material stabilized at a lower pH and with potassium sorbate (Sample A) had less lipase/esterase activity than the one stabilized at higher pH with Sodium chloride (Sample B), even when normalizing to 1000 BLU (see, TABLE 3) correcting for dilution of the UFC.

TABLE 3

LIPASE ACTIVITY IN ULTRA-FILTRATION CONCENTRATES

| Product ID | LIPU/g | BLU/g | LIPU/1000 BLU |
|---|---|---|---|
| Sample A | 0.42 | 1650 | 0.25 |
| Sample B | 0.90 | 1223 | 0.74 |

In order to better understand why the off-flavor was not detected in the initial sensory trial, several samples were selected for quantification of esterase activity. The lipase level in these samples were quantified using LIPU-k (E117), correcting for sample blank values and normalized to 1000 BLU to compare the results. The samples compared were (A) the powder material "C", originating from the UFC A (from a large scale fermentation), (B) a sample representing spray dried material D (from a small scale fermentation) and (C) the actual sample E used for the sensory trial (from a small scale fermentation). The quantified lipase levels are shown in TABLE 4. Looking at the lipase/esterase levels normalized to the 0-galactosidase activity, it shows there was less lipase in sample D (small scale fermentation) and sample E (used for sensory analysis).

TABLE 4

LIPASE ACTIVITY IN POWDER SAMPLES

| Product ID | LIPU/g | BLU/g | LIPU/1000 BLU |
|---|---|---|---|
| Sample C | 0.41 | 1625 | 0.25 |
| Sample D | 0.30 | 2576 | 0.12 |
| Sample E | 0.12 | 1050 | 0.11 |

More particularly, sample D and E from small scale fermentations show approximately half the lipase level, compared to materials originating from the full scale fermentation sample C. It does indicate that the lipase/esterase level had increased when going into full scale (fermentation) production. Taking the above into consideration, it is not too surprising that sample C from the large scale (fermentation) production shows increased lipase activity relative to samples D and E from the small scale (fermentation) production, as the large scale fermentation of sample C has a higher number of cell doublings (i.e., generations) than small scale fermentation (i.e., samples D and E). Thus, the most probable explanation for a higher level of (unwanted) lipase side activity is that the activity thereof originates from the *Bacillus* host cell used to produce the β-galactosidase enzyme. For example, the threshold limit of tasting this off-flavor in yoghurt was initially unknown, whereas the data presented herein indicates that going from 0.11 LIPU/1000 BLU to 0.25 LIPU/1000 BLU shifted the off-flavor from below detection limits to above detection limits by tasting within the first week.

Lipase/Esterase Zymogram

Figure 2:
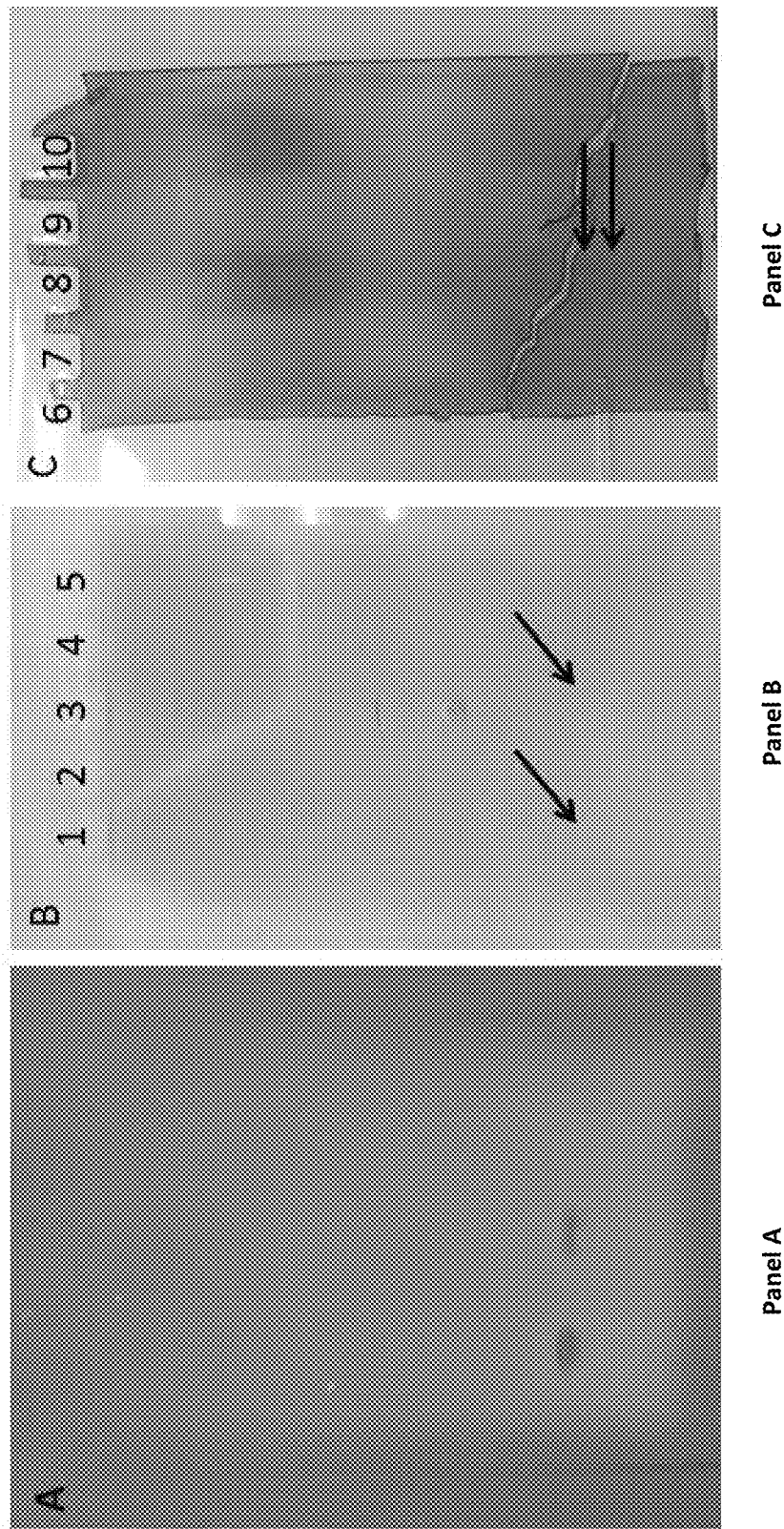
FIG. 2 shows a lipase/phospholipase zymogram.
Figure 3:
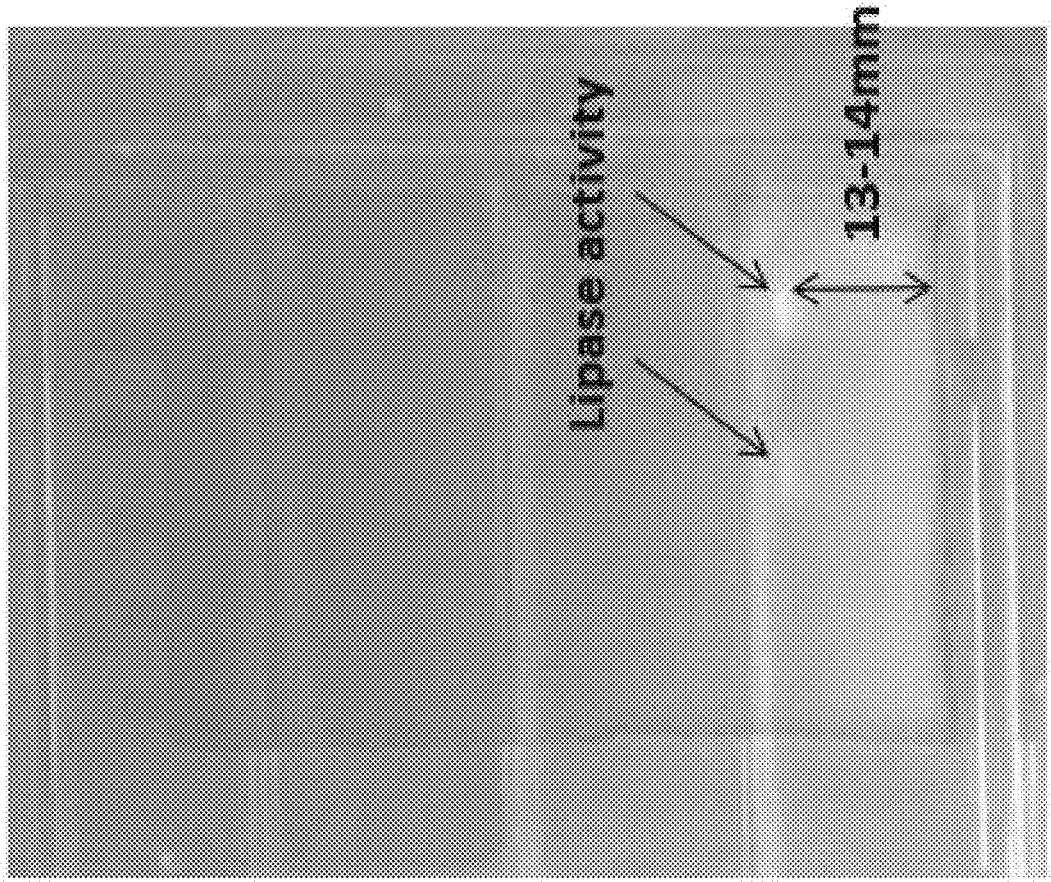
FIG. 3 Supporting picture while the IEF gel was still placed on the agar gel with substrate (FIG. 2, panel B and panel C together after 1 hour). The clear yellow bands represent a drop in pH from cleavage of lipase substrate, resulting in free fatty acids and an equivalent $H^+$.

In order to narrow the area of choice for identification by nano-LC-MSMS, a lipase/phospholipase zymogram was run. The material C was symmetrically loaded on a (pH 3-10) isoelectric focusing (IEF) gel. Afterwards the gel was cut in two (2). The first part (FIG. 2, panel B) was placed on an agar gel (FIG. 2, panel A) containing 1% tributyrin, 0.75% lecithin, 0.2 M HEPES buffer (pH 7.4), 0.01M $CaCl_2$ and phenol red and incubated at 40° C. for two (2) hours. The second part was fixed and stained with coomassie (FIG. 2, panel C). From the agar gel (FIG. 2, panel A) one can see where the lipase/esterase (from FIG. 2, panel B) through overlay had degraded the substrate leaving clear holes in the gel. The band on the coomassie blue stained gel (FIG. 2, panel C) indicated with the upper arrow, was located 13-14 mm from the bottom of the gel, similar to were the lipase activity was located as indicated in the in the agar gel (see, FIG. 3). Bands indicated by arrows in the gel presented in FIG. 2, panel C were cut out for identification.

The result of nano-LC-MSMS identification showed an identified para-nitrobenzylesterase (p-NBE; SEQ ID NO: 2) in the upper band (upper arrow in FIG. 2, panel C), which is described in the literature as having lipase activity (Ribitsch et al., 2011). The result further indicates that the p-NBE enzyme originates from the *Bacillus subtilis* host cell (i.e., as opposed to cross-contamination). Furthermore, a carboxyesterase was identified in the lower band (lower arrow in FIG. 2, panel C), wherein the identified carboxyesterase has high sequence homology to the p-NBE. However, sequence comparison revealed that the identified carboxyesterase was an artifact of proteolytic cleavage of the para-nitrobenzylesterase.

The biochemical characteristics of the *B. subtilis* p-NBE has been described in the literature (Chen et al., 1995; Kaiser et al., 2006; Ribitsch et al., 2011). The enzyme is specific towards short chain p-nitrophenyl esters and triacylglycerols. Furthermore, the p-NBE has a pH optimum of 8 and is stimulated by $Ca^{2+}$. In addition, the lipase/esterase spot plates used in the present disclosure are pH 7.4 and contain $Ca^{2+}$, providing further evidence of why these particular spot plates are very sensitive towards the p-NBE enzyme. For example, the p-NBE enzyme is almost inactive at pH 5 (~10% remaining activity), but retains approximately 50% activity at pH 6.5, relative to its pH optimum of 8 (Kaiser et al., 2006). Thus, the different pH specifications on the UFC's might explain why more lipase activity is observed in the material B compared to the material A, as the p-NBE is less stable at the low pH. Furthermore, the p-NBE should be stable up to 50° C., but will be rapidly and irreversible inactivated at temperatures above 50° C.

Putative Method for Inactivation of the Lipase/Esterase Activity

Figure 4:
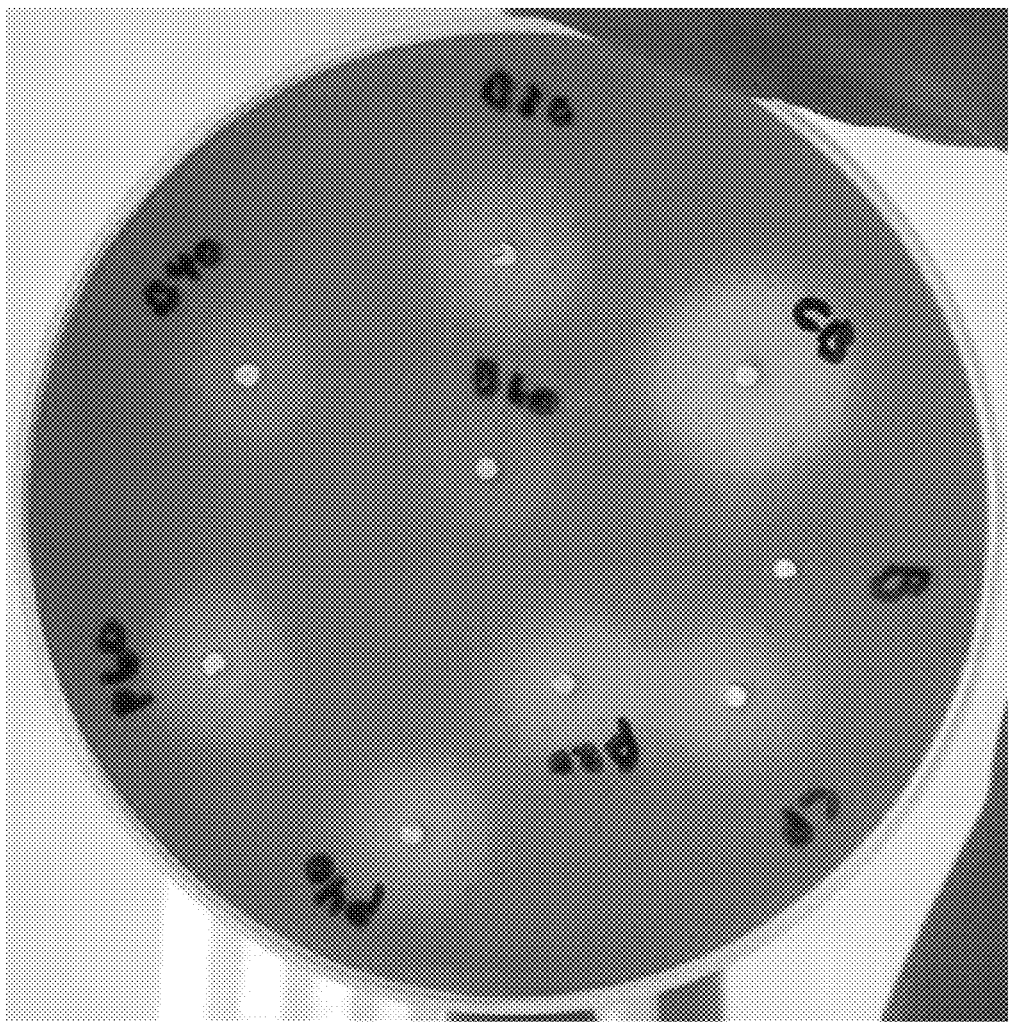
FIG. 4 shows CP as the powder control and p20, p40 and p60 are the powder incubated at 53° C. for 20, 40, and 60 minutes. CB is the UFC sample A and B20, B40 and B60 is sample A incubated for 20, 40 and 60 minutes.

It was tested whether heat treatment above 50° C., but below the 55° C., could inactivate the lipase/esterase activity, without affecting the β-galactosidase activity (i.e., it is contemplated that a temperature above 55° C. would compromise the β-galactosidase activity severely). Thus, material A and C were tested by incubation at 53° C. for 20 minutes, 40 minutes and 60 minutes. No physical change was observed in the powder material C, but severe aggregation was formed in the UFC sample A. This aggregation was removed by centrifugation (5 minutes at 12,000 rpm). Residual esterase activity was semi-quantified on the agar spot plates (see, FIG. 4).

No difference in size of haloes from heat treating the powder was observed. Comparing halo sizes in the experiment when determining the sensitivity of the lipase/esterase spot plate, the estimated residual esterase activity of the UFC A as follows:

CB—100%

B-20 minutes—5%

B-40 minutes—2.5%

Furthermore, the lactase activity was quantified according to a ten (10) minute hydrolysis of a colorless substrate, 2-nitrophelyl β-D-galactopyranoside (ONPG) to a yellow 2-nitrophenol (ONP) and galactose at 30° C. The reaction was stopped with 750 μL 10% sodium carbonate, and ONP was determined at $OD_{420}$. The activity was calculated against a standard curve prepared by dilutions of sample C. Set forth in Table 5 are the β-galactosidase activities after 53° C. heat treatment of the samples.

TABLE 5

β-GALACTOSIDASE ACTIVITY AFTER HEAT TREATMENT AT 53° C.

| ID | Activity (BLU/g) | % relative to B-0 minutes | % residual total units after removal of aggregate |
|---|---|---|---|
| B-0 minutes | 1593 | 100% | 100% |
| B-20 minutes | 1143 | 72% | 54% |
| B-40 minutes | 1018 | 64% | 45% |
| B-60 minutes | 744 | 47% | 30% |

From this the relation between Lipase and β-galactosidase activity can be calculated. As presented in Table 6, the Lipase activity was significantly reduced after just twenty (20) minutes incubation (i.e., sample B20; Table 6), and hence should be below detection limit for of off-flavor in Yoghurts and UHT milk.

TABLE 6

LIPASE ACTIVITY NORMALIZED TO β-GALACTOSIDASE

| ID | LIPU/g | BLU/g | LIPU/1000 BLU |
|---|---|---|---|
| B0 | 0.4100 | 1593 | 0.2574 |
| B20 | 0.0205 | 1143 | 0.0179 |
| B40 | 0.0102 | 1018 | 0.0100 |
| B60 | 0.0102 | 744 | 0.0137 |

It was decided to further evaluate the stability of lactase and esterase activity at 48° C., 51° C. and 53° C. Samples were aliquoted and incubated at various temperatures and times. Afterwards the esterase (FIG. 5) and lactase (FIG. 6) activity was determined, wherein the aggregation formed was removed by centrifugation as previously described.

Figure 5:
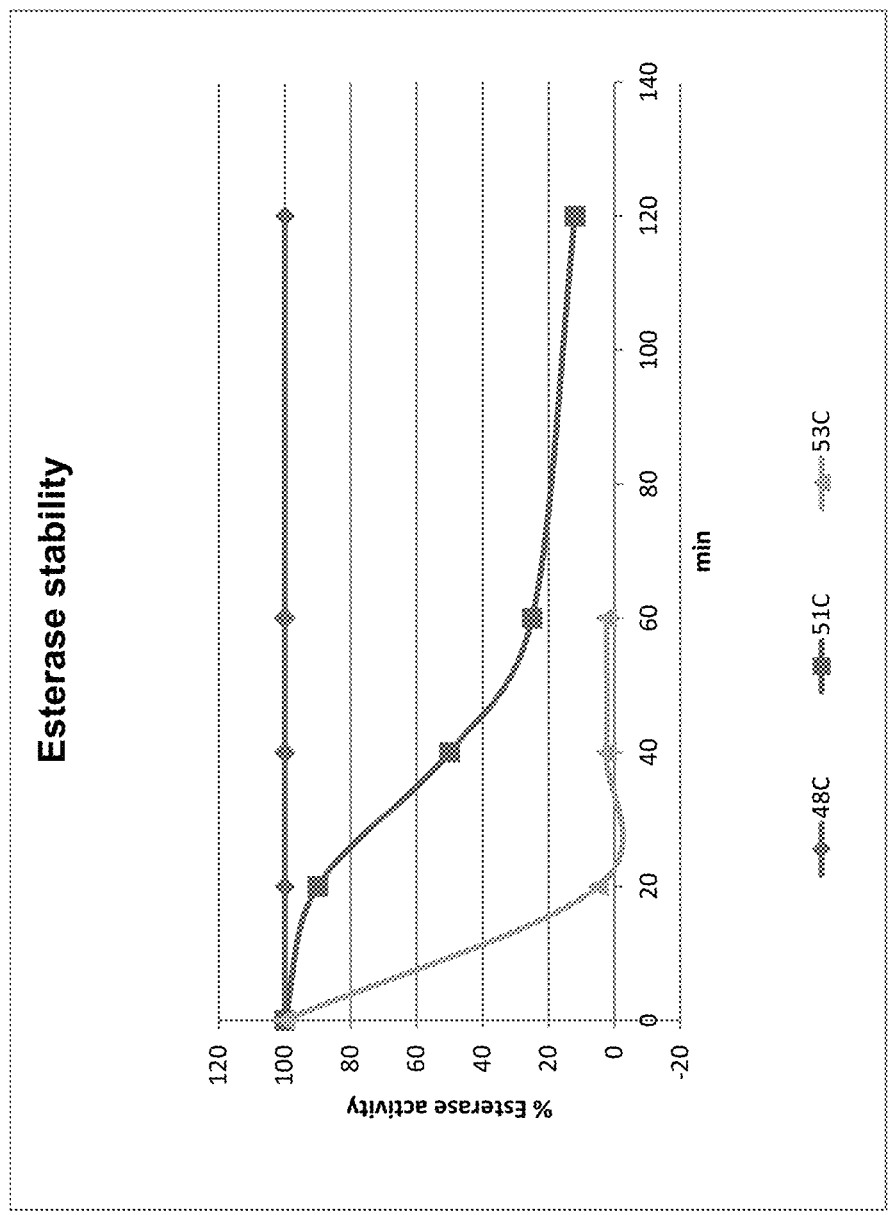
FIG. 5 shows esterase activity semi-quantified by evaluation of haloes sizes on the mixed substrate spot plates. Halo sizes were compared to the dilution row shown in FIG. 1B and presented as relative to the activity of Sample C stored at 4° C.
Figure 6:
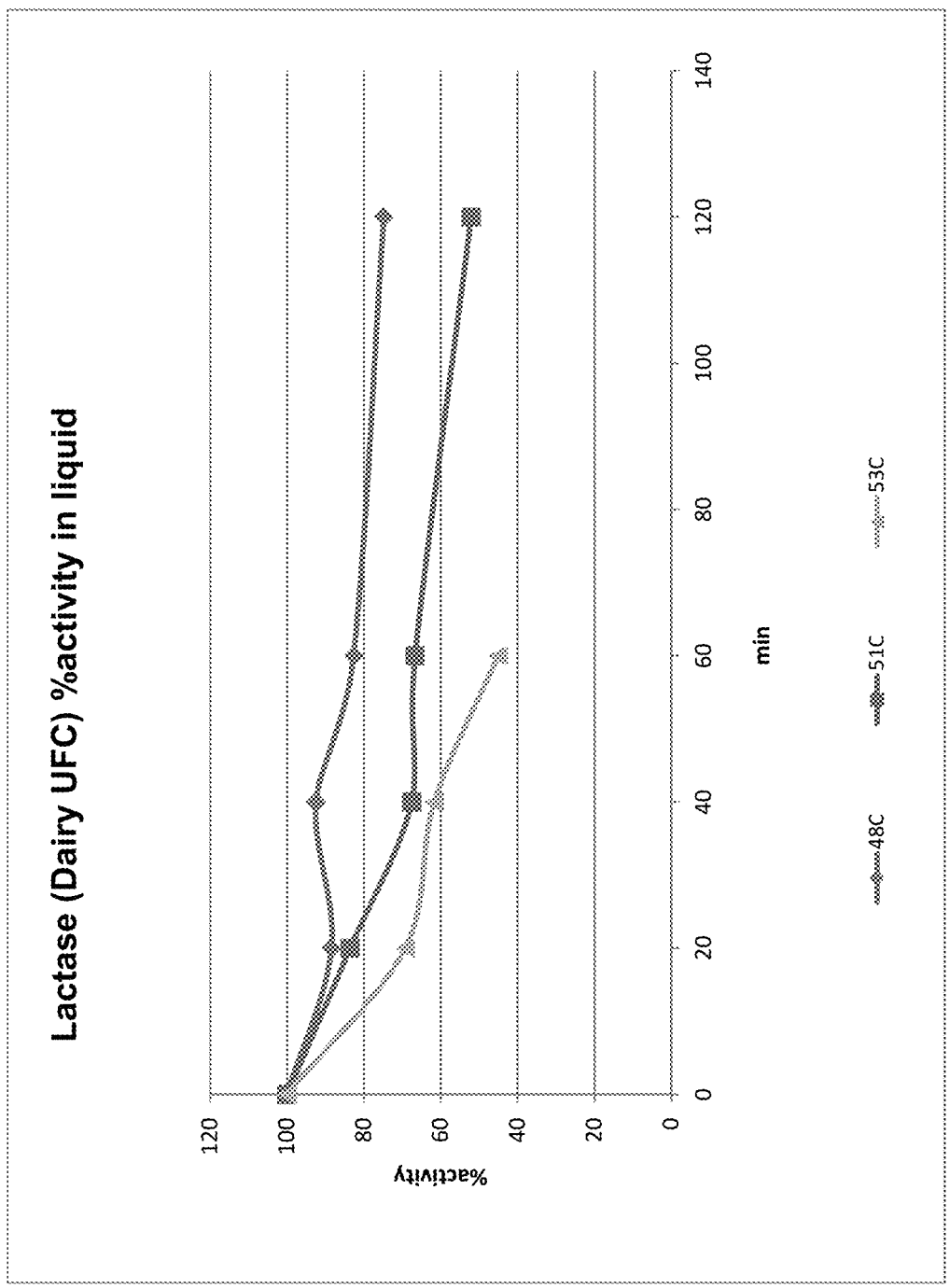
FIG. 6 shows residual lactase activity after heat treatment.

As presented in FIG. 5, the esterase activity is not significantly reduced by the 48° C. incubation and one would need to incubate for 129 minutes or more to inactivate the esterase. As presented in FIG. 5, the 53° C. incubation is the most effective temperature, having reduced the activity approximately 95% after just 20 minutes. As presented in FIG. 6, after 20 minutes of incubation, there is not much difference in recovery between temperatures used (i.e., 48° C., 51° C. and 53° C.), and further incubation time will only lead to further reduction of lactase activity at all temperatures tested. Thus, based on esterase stability, a temperature of 53° C. for 20 minutes would be the recommended treatment of the UFC sample A (although longer incubation times may be required for larger volumes).

Dose Dependent Application Trials

To determine the analytical fingerprint of the off-flavor in both UHT milk and yoghurt, trials were run with various doses of material, which were dosed as shown in Tables 7 and 8 below. The UHT milk was processed as follows; indirect tubular heating, downstream homogenization 200 bar at 75° C.

TABLE 7

YOGHURT TRIAL

| Ingredients | 61 | 62 | 63 | 64 | 65 | 66 |
|---|---|---|---|---|---|---|
| Low fat milk 1.5% Fat | 100 | 99.87 | 99.903 | 99.935 | 99.968 | 99.987 |
| Sample C | 0 | 0.13 | 0.098 | 0.065 | 0.033 | 0.013 |
|  | 100.000 | 100.000 | 100.000 | 100.000 | 100.000 | 100.000 |

TABLE 8

UHT MILK TRIALS

| Ingredients | 51 | 52 | 53 | 54 | 55 | 56 |
|---|---|---|---|---|---|---|
| Low fat milk 1.5% Fat | 100 | 99.87 | 99.903 | 99.935 | 99.968 | 99.987 |
| Sample C | 0 | 0.13 | 0.098 | 0.065 | 0.033 | 0.,013 |
|  | 100.000 | 100.000 | 100.000 | 100.000 | 100.000 | 100.000 |

After one (1) week of storage at either 5° C. or ambient temperatures, the samples were tasted and it was found that dosing above 0.033% resulted in off-flavor in both the yoghurts and UHT milk, whereas dosing at 0.033% or below, the off-flavor could not be perceived after the one week of storage (see, Tables 9 and 10 below).

TABLE 9

SENSORY EVALUATION OF YOGHURT - TASTING AFTER 7 DAYS OF STORAGE AT 5° C.

| Trial no. | Cold storage (5° C.) |
|---|---|
| 61 | nothing |
| 62 | Off-flavor |
| 63 | Off-flavor |
| 64 | nothing |
| 65 | nothing |
| 66 | nothing |

TABLE 10

SENSORY EVALUATION OF UHT MILK - TASTING AFTER 7 DAYS OF STORAGE

| Trial no. | Ambient temp - dark |
|---|---|
| 51 | nothing |
| 52 | Bad taste |
| 53 | Smell |
| 54 | Slight Smell |
| 55 | nothing |
| 56 | nothing |

Figure 7:
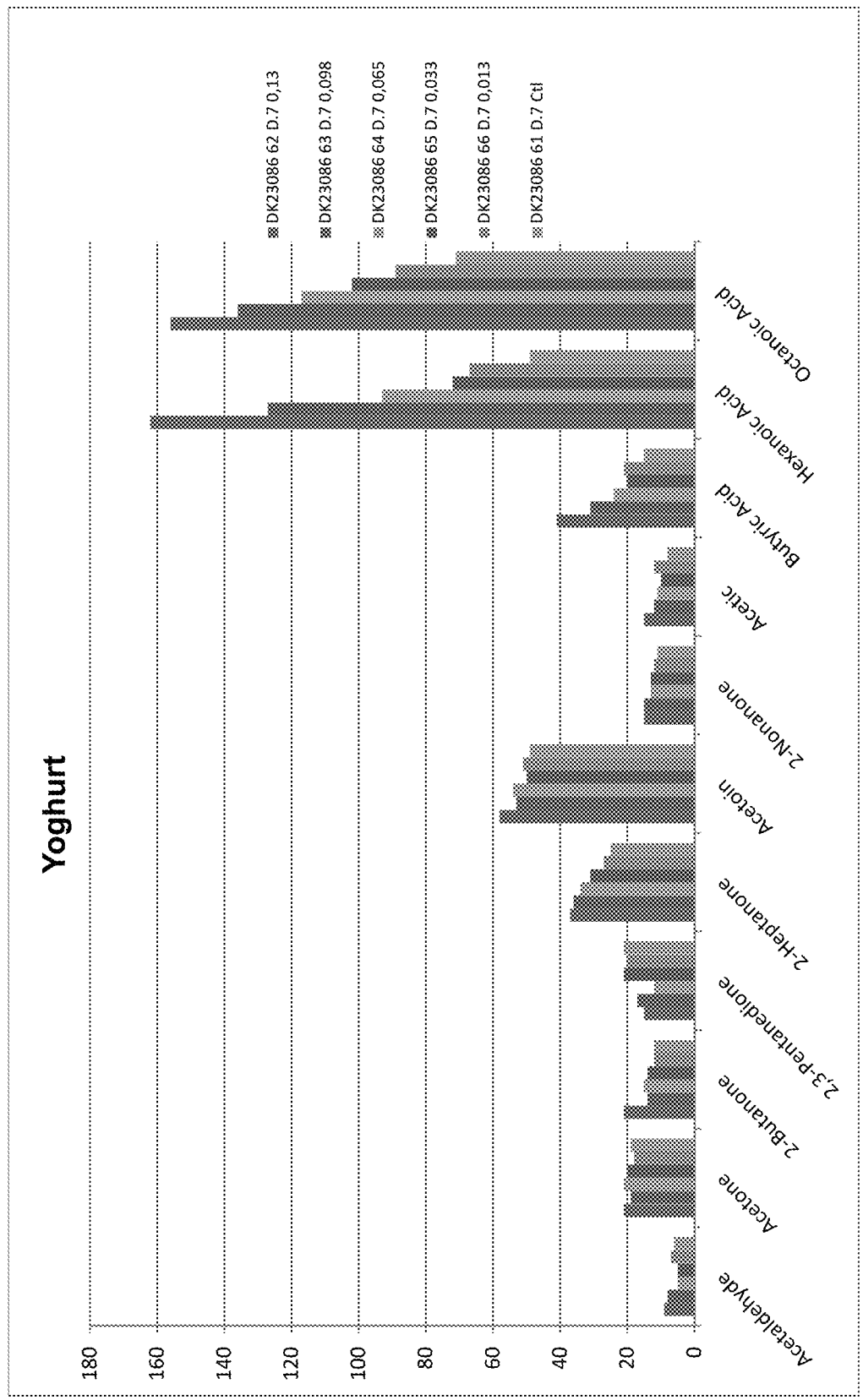
FIG. 7 shows off-flavor profile of yoghurts treated with sample C. Levels of each component were quantified by Solid Phase Micro Extraction—GC/MS-analysis.
Figure 8:
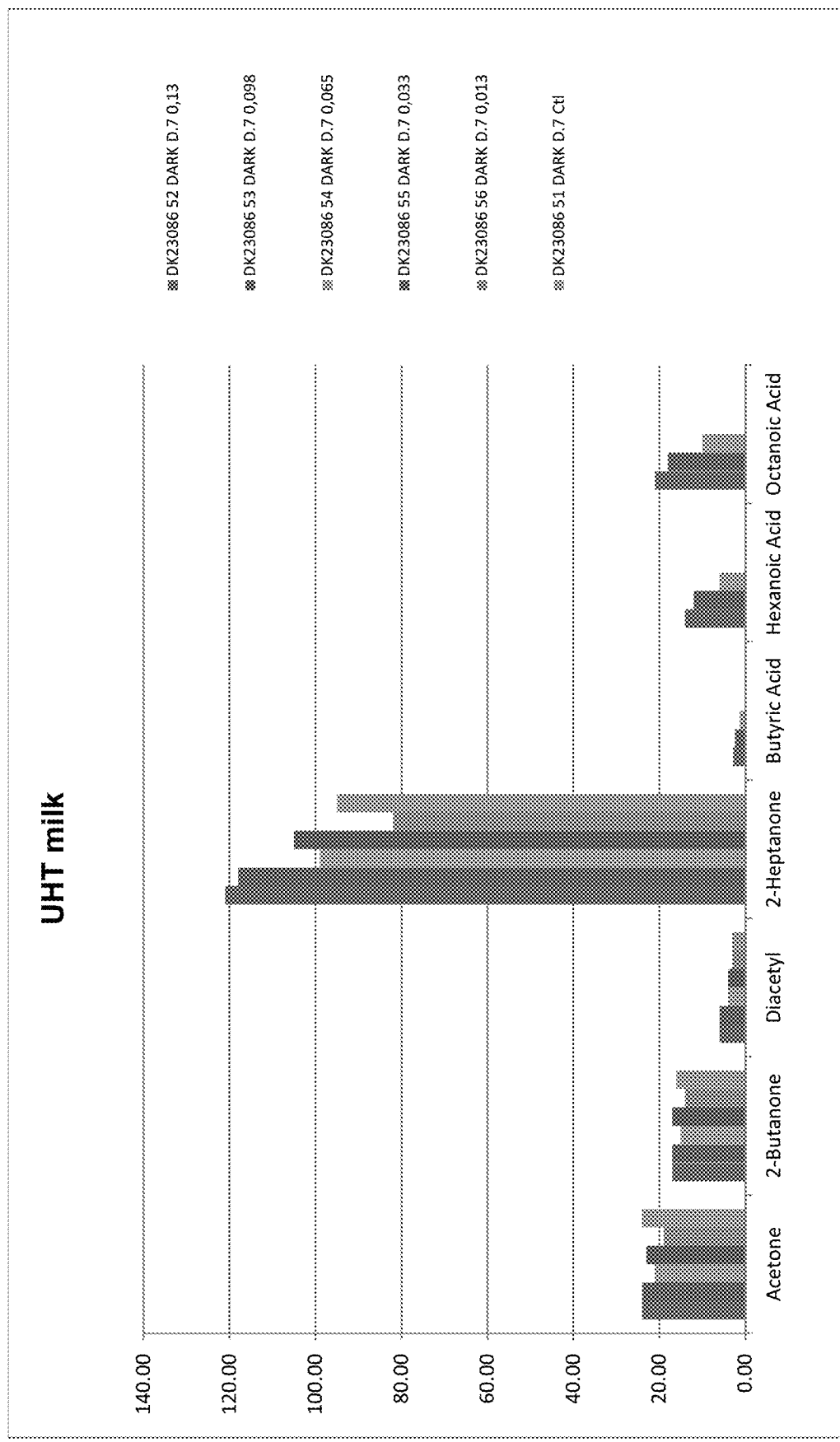
FIG. 8 shows off-flavor profile of UHT milk treated with sample C. Levels of each component were quantified by Solid Phase Micro Extraction—GC/MS-analysis.

In addition, after one (1) week storage of the yoghurts and UHT milk, samples were also sent for analysis of flavor components, which mainly included ketones and free fatty acids. It was clear that the off-flavor profile was different in the two applications. For the yoghurts (FIG. 7), it was mainly free fatty acid levels that increased by increasing doses of the β-galactosidase powder material C and to less degree the ketones. In the UHT milk (FIG. 8), both the free fatty acids and the ketones, especially 2-heptanone, were increasing according to the dose.

Figure 9:
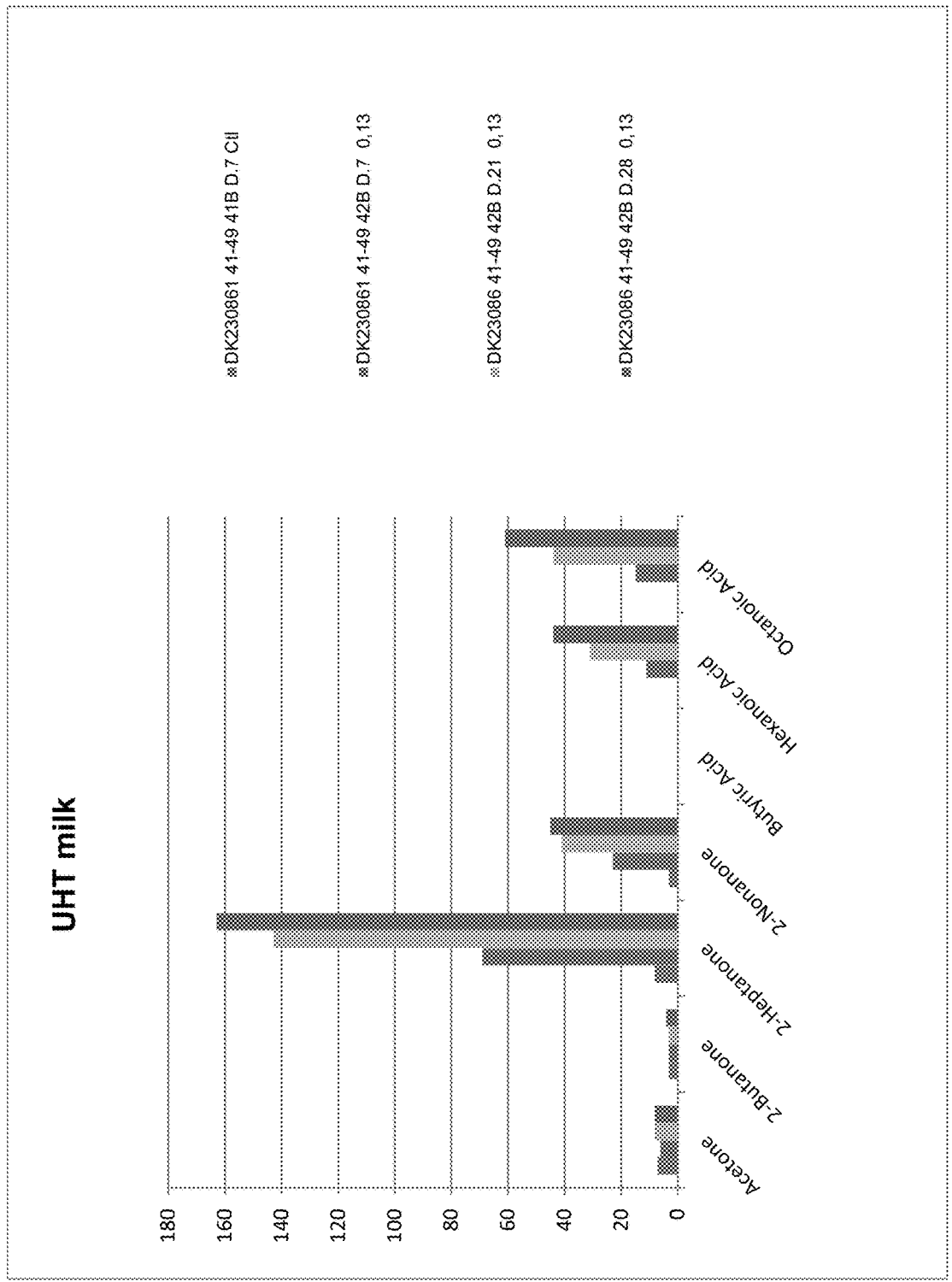
FIG. 9 shows off-flavor development in UHT milk over time treated with Sample C.

Thus, having processed the UHT milk by indirect tubular heating seemed to mask some of the off-flavor. For example, another trial in UHT milk (which was processed by direct infusion), appeared to be more sensitive to the off-flavor. For example, as presented in FIG. 9, it is clearly shown that having dosed at 0.13%, there were increasing levels of free fatty acids (especially the 2-heptanone and 2-nonanone) over storage time period.

Example 2

*Bacillus* Host Cells Genetically Modified to be Deficient in p-Nitrobenzylesterase Side Activity The *Bacillus subtilis* pnbA gene (SEQ ID NO: 1) encoding the para-nitrobenzylesterase (SEQ ID NO: 2) was deleted using the marker-less method described by Janes and Stibitz (2006). The construction of the integration plasmid pKSV-I-Sce-Km was performed as follows. Twenty (20) picomoles of two (2) single-strand oligomers, I-SceI-1 (cgatTAGGGATAACAGGGTAATat; SEQ ID NO: 19, bold letters with underline are a homologous sequence of I-SceI restriction enzyme site) and I-SceI-2 (cgatATTACCCTGT-TATCCCTAat; SEQ ID NO: 20), were incubated at 98° C. for 7 minutes and then kept at 55° C. for 5 minutes to anneal the oligomers. The annealed fragment was phosphorylated with T4 polynucleotide kinase (New England BioLabs) and was then ligated with the ClaI site of pKSV7 (Smith and Youngman, 1992). To eliminate the chloramphenicol resistance gene present in pKSV7, the plasmid was digested with NcoI and MfeI, and was blunted with T4 DNA polymerase (New England BioLabs). The fragment containing repF and cop-6 had been separated from the chloramphenicol resistance gene fragment by agarose gel electrophoresis, and purified with a gel extraction kit (Qiagen), then self-ligated to originate the pKS vector. The pKS vector was digested with the restriction endonuclease HindIII and ligated to the kanamacyn resistant gene derived from the plasmid pDG780 (Guérout-Fleury et al., 1995) after digestion with HindIII restriction endonuclease, wherein the resulting plasmid is "pKSV-I-Sce Km".

The loci upstream and downstream the pnbA gene were amplified by PCR from *B. subtilis* 168 genomic DNA, using the following primers: Primer No. 981: 5'-AACCAGCACTAGTGTCGACGCCTGGTAGGTCG-3' (SEQ ID NO: 21); Primer No. 984: 5'-GCAC-CAATGTATCCTGTTTTCCCCATATCGTTAGCCCTT-TAACCGATCATCATC-3' (SEQ ID NO: 22); Primer No. 985: 5'-ATATGGATCCGTTCTACTAGACATTTAT-GAAGTACAG-3' (SEQ ID NO: 23) and Primer No. 983: 5'-GATGATGATCGGTTAAAGGGCTAACGATATGGG-GAAAACAGG-3' (SEQ ID NO: 24).

The two PCR products were assembled by fusion PCR using Primer No. 981: 5'-AACCAGCAC TAGTGTCGACGCCTGGTAGGCG-3' (SEQ ID NO: 21) and Primer No. 985: 5'-ATATGGATCCGT TCTACTAGA-CATTTATGAAGTACAG-3' (SEQ ID NO: 23).

The amplicon was digested with the restrictions sites SpeI and BamHI, and ligated to the pKSV-I-Sce-Km vector linearized with the restriction enzymes XbaI and BamHI, wherein the resulting vector was named pKSV-ISce-pnbA.

The pKSV-ISce-pnbA vector was transformed and integrated into the genome of a parental *B. subtilis* host cell. A second vector, called pKBJ233 (Janes and Stibitz, 2006), containing the expression construct for the restriction enzyme I-Sce was used to transform the parental *B. subtilis* (pksV-ISce-pnbA) host cell. The strain was grown for 72 hours by renewing the media every 12 hours, then re-isolated on Luria agar plates. The kanamycin sensitive clones were selected and tested by PCR for the deletion of the pnbA gene. The resulting *B. subtilis* daughter cell (i.e., comprising a deleted pnbA gene) was named CB103.

Example 3

Evaluation of UFC Material after Knock Out of P-Nitrobenzylesterase Gene in the Host Strain As set forth above in Example 2, the *B. subtilis* gene encoding the identified and unwanted p-NBE enzyme activity (SEQ ID NO: 2) was deleted in the *B. subtilis* (β-galactosidase and/or lactase producing) host cell of the instant disclosure. Thus, the resulting p-NBE deleted *B. subtilis* host cell described in Example 2 was used for fermentation of the β-galactosidase. It is noted herein that the deletion (knocking-out) of particular a gene presents certain risks if the deleted gene in question is either essential to the host cell or if the host cell compensates by expressing another enzyme with similar characteristics. As described herein, the gene encoding the p-NBE enzyme is not essential to the *B. subtilis* host cell, and as such, the UFC material resulting from the fermentation of the p-NBE deleted *B. subtilis* host cell was therefore tested for esterase activity by the spot plate analysis.

Figure 10:
FIG. 10 is a spot plate assay showing results of sample A incubated at 53° C. for 20 minutes and a UCF sample from small scale fermentation of β-galactosidase in a new *Bacillus* host cell where the p-nitrobenzylesterase gene was knocked out. The 53° C. sample was therefore positive for lipase activity. All holes labeled "new" correspond to the p-nitrobenzylesterase knock out sample having had no lipase activity, and as such have no halo.

As a positive control 20 µL of a 53° C. heat treated sample was applied. Similarly, 10 µL and 20 µL of the new material (i.e., produced in the p-NBE deleted *B. subtilis* host cell) was applied to the spot plate and incubated at 40° C. for 24 hours. As presented in FIG. 10, no esterase activity was detectable in the new material. As presented in FIG. 10, the yellow halo represents lipase activity in the 53° C. treated sample (labeled 53C in FIG. 10). In contrast, the spot plate holes in FIG. 10, labeled "New" (i.e., lacking yellow haloes), which correspond to the samples produced from the *B. subtilis* host cell in which the gene encoding p-NBE enzyme has been deleted (Example 2), had no detectable lipase activity (FIG. 10).

Subsequently, both sample C (i.e., comprising the p-NBE side-activity) and the new p-NBE free material (i.e., produced from the *B. subtilis* Δp-NBE host cell) were used in application trials of both Yoghurt and UHT milk (processed by direct infusion) to confirm that the off-flavor had been completely eliminated. Thus, to ensure that any slight changes of components were clearly detectable in the assay, it was decided to overdose the new material at 0.207%.

Figure 11:
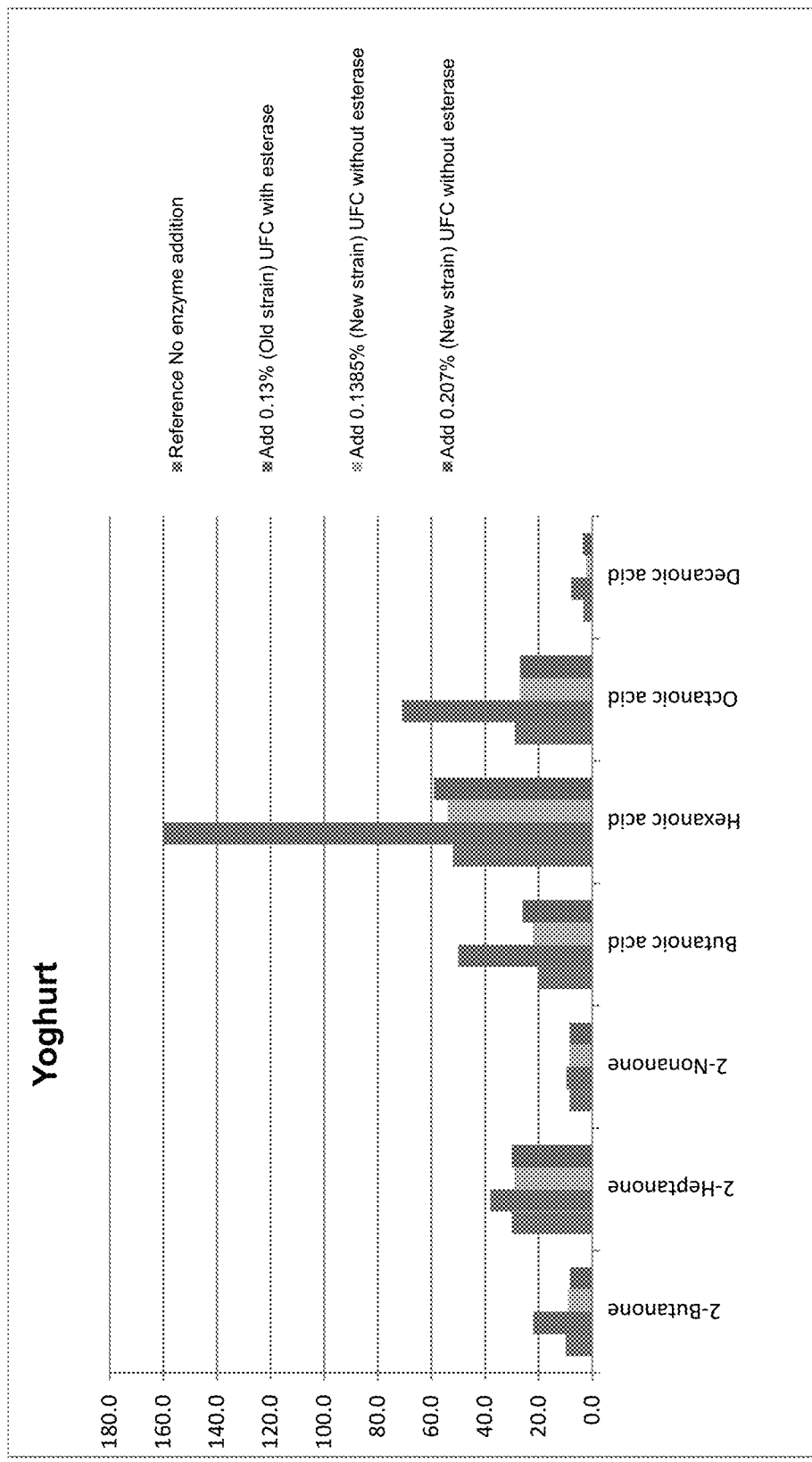
FIG. 11 shows the off-flavor profile of yoghurt treated with an UCF sample from small scale fermentation of β-galactosidase in a new *Bacillus* host cell where the p-nitrobenzylesterase gene was knocked out (green and purple) versus Sample C (red). Levels were quantified by Solid Phase Micro Extraction—GC/MS-analysis.
Figure 12:
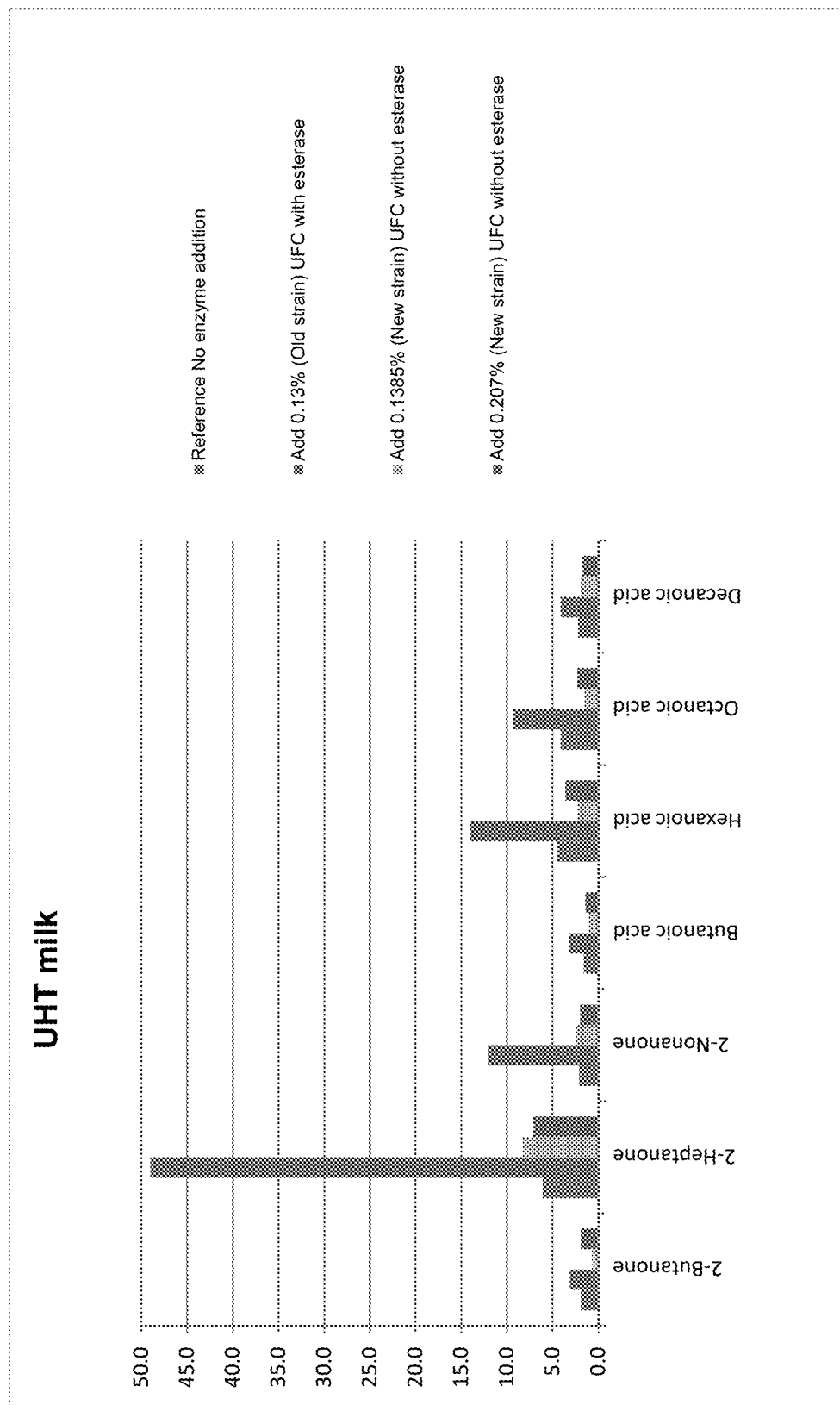
FIG. 12 shows the off-flavor profile of UHT milk treated with an UCF sample from small scale fermentation of β-galactosidase in a new *Bacillus* host cell where the p-nitrobenzylesterase gene was knocked out (green and purple) versus Sample C (red). Levels were quantified by Solid Phase Micro Extraction—GC/MS-analysis.

As presented in FIG. 11 (Yoghurt) and FIG. 12 (UHT milk), it is clearly observed that the new UFC material is comparable to the control (i.e., FIGS. 11 and 12; Reference, no enzyme added) and as such, the new UFC material does not result in off-flavor in the specified applications. Furthermore, FIG. 11 and FIG. 12 clearly show that the esterase containing material (Old strain) has higher levels of free fatty acids and ketones than the other samples (i.e., New strain), wherein the 2-heptanone in the UHT milk contributes significantly to the off-flavor.

Thus, as described herein, the deletion of the gene encoding the p-NBE enzyme (SEQ ID NO: 2) in the *B. subtilis* host cell (see, Example 2) used to produce P-galactosidases and/or lactases of the disclosure completely eliminated the off-flavor caused by the p-NBE enzymatic side activity present in the original (parental) *B. subtilis* host cell, which p-NBE activity has been eliminated in the modified (daughter) *B. subtilis* host cell.

REFERENCES

European Patent Application No. EP0458358
International PCT Publication No WO2001/51643
International PCT Publication No. WO2001/90317
International PCT Publication No. WO2002/14490
International PCT Publication No. WO2003/083125
International PCT Publication No. WO2003/089604
International PCT Publication No. WO2003/186286
International PCT Publication No. WO2005/026356
International PCT Publication No. WO2005/05672
International PCT Publication No. WO2008/037839
International PCT Publication No. WO2009/071539
International PCT Publication No. WO2011/120993
International PCT Publication No. WO2012/010597
International PCT Publication No. WO2013/182686

International PCT Publication No. WO2015/086746
International PCT Publication No. WO2016/071500
International PCT Publication No. WO2016/071504
U.S. Pat. No. 6,667,065
U.S. Pat. No. 6,890,572
U.S. Pat. No. 7,166,453
U.S. Pat. No. 7,371,552
U.S. Published Application No. 2005/0137111
U.S. Published Application No. 2006/0008888
U.S. Published Application No. 2006/0008890
U.S. Published Application No. 2006/0018997
U.S. Published Application No. 2006/0019347
U.S. Published Application No. 2006/0073583
U.S. Published Application No. 2007/0020727
U.S. Published Application No. 2007/0020731
U.S. Published Application No. 2007/0072270
U.S. Published Application No. 2007/0141693
U.S. Published Application No. 2012/0040051
U.S. Published Application No. 2014/0329309
Ausubel et al., *Current Protocols in Molecular Biology*, 1994.
Botstein and Shortle, *Science* 229: 4719, 1985.
Campbell et al., *Curr. Genet.* 16: 53-56, 1989.
Chang et al., *Mol. Gen. Genet.*, 168:11-115, 1979.
Chen et al., "Purification and Properties of a p-nitrobenzyl esterase from *Bacillus subtilis*", *J. Ind. Microbiol.*, 15: 10-18, 1995.
Ferrari et al., "*Genetics*," in Harwood et al. (ed.), *Bacillus*, Plenum Publishing Corp., 1989.
Fisher et. al., *Arch. Microbiol.*, 139:213-217, 1981.
Guérout-Fleury et al., "Antibiotic-resistance cassettes for *Bacillus subtilis*", *Gene*, 167(1-2): 335-336, 1995.
Higuchi et al., *Nucleic Acids Research* 16: 7351, 1988.
Ho et al., *Gene* 77: 61, 1989.
Hoch et al., *J. Bacteriol.*, 93:1925-1937, 1967.
Holubova, *Folia Microbiol.*, 30:97, 1985.
Horton et al., *Gene* 77: 61, 1989.
Iglesias and Trautner, *Molecular General Genetics* 189: 73-76, 1983.
Janes and Stibitz, "Routine Markerless Gene Replacement in *Bacillus anthracis*", *Infect. Immun.*, 74(3): 1949-1953, 2006.
Jorgensen et al., *Appl. Microbiol. Biotechnol.*, 57: 647-652, 2001.
Kaiser et al., A Novel Esterase from *Bacillus subtilis* (RRL 1789): Purification and Characterization of the Ezyme", *Protein Expres. Purif,* 45: 262-268, 2006.
Kriegler, *Gene Transfer and Expression: A Laboratory Manual*, 1990.
Lo et al., *Proceedings of the National Academy of Sciences USA* 81: 2285, 1985.
M. J. Gait, ed., *Oligonucleotide Synthesis*, 1984.
Mann et al., *Current Microbiol.*, 13:131-135, 1986.
McDonald, *J. Gen. Microbiol.*, 130:203, 1984.
Mullis et al., eds., *PGR: The Polymerase Chain Reaction*, 1994.
Oliveira et al., *Biotechnology Advances* 29:600-609, 2011.
Palmeros et al., *Gene* 247:255-264, 2000.
Parish and Stoker, *FEMS Microbiology Letters* 154: 151-157, 1997.
Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.
Ribitsch et al., "Hydrolysis of Polyethyleneterephthalate by p-Nitrobenzylesterase from *Bacillus subtillis*", *Biotechnol. Prog.*, 27(4): 951-960, 2011.
Rodriguez-Colinas et al., *The Journal of Agricultural and Food Chemistry*, 60: 6391-6398, 2012.
Sambrook et al., *Molecular Cloning: A Laboratory Manual*, second edition, 1989.
Sarkar and Sommer, *BioTechniques* 8: 404, 1990.
Saunders et al., *J. Bacteriol.*, 157: 718-726, 1984.
Shimada, *Meth. Mol. Biol.* 57: 157; 1996
Smith and Youngman, "Use of a new integrational vector to investigate compartment-specific expression of the *Bacillus subtilis* spoIIM gene", *Biochimie* 74(7-8): 705-711, 1992.
Smith et al., *Appl. Env. Microbiol.*, 51: 634 1986.
Stahl et al, *J. Bacteriol.*, 158: 411-418, 1984.
Vorobjeva et al., *FEMS Microbiol. Lett.*, 7:261-263, 1980.

The invention claimed is:

1. A *Bacillus* sp. host cell expressing an introduced polynucleotide construct encoding a recombinant polypeptide comprising β-galactosidase activity or transgalactosylating activity, wherein the host cell comprises a genetic modification which reduces or eliminates para-nitrobenzylesterase (p-NBE) activity.

2. The host cell of claim 1, wherein the modification comprises a deletion, disruption or down-regulation of a gene encoding a p-NBE polypeptide comprising at least 60% sequence identity to the p-NBE polypeptide of SEQ ID NO: 2.

3. The host cell of claim 2, wherein the modification comprises a disruption of a gene encoding a p-NBE polypeptide comprising at least 60% sequence identity to the p-NBE polypeptide of SEQ ID NO: 2.

4. The host cell of claim 3, wherein the p-NBE gene disruption comprises the insertion of a selectable marker into the p-NBE gene.

5. The host cell of claim 2, wherein the modification is a down-regulation of a gene encoding a p-NBE polypeptide comprising at least 60% sequence identity to the p-NBE polypeptide of SEQ ID NO: 2.

6. The host cell of claim 5, wherein down-regulation of a gene encoding a p-NBE comprises introducing and expressing in the host cell an RNA molecule complementary to a gene encoding a p-NBE.

7. The host cell of claim 5, wherein down-regulation of a gene encoding a p-NBE comprises (a) complete or partial deletion of an endogenous p-NBE promoter nucleic acid sequence, (b) complete or partial deletion of an endogenous p-NBE terminator nucleic acid sequence, or combinations thereof, and optionally deletion of other 5' UTRs and/or 3' UTR nucleic acid sequence associated with a gene encoding a p-NBE polypeptide comprising at least 60% sequence identity to the p-NBE polypeptide of SEQ ID NO: 2.

8. The host cell of claim 1, wherein the modification comprises a complete or partial deletion of a gene encoding a p-NBE polypeptide comprising at least 60% sequence identity to the p-NBE polypeptide of SEQ ID NO: 2.

9. The host cell of claim 8, wherein the partial deletion comprises deleting one or more codons encoding the p-NBE active site amino acids $Ser_{189}$, $Glu_{310}$ and/or $His_{399}$.

10. The host cell of claim 8, wherein the partial deletion comprises a nucleotide frameshift deletion in the gene encoding the p-NBE, wherein the frameshift deletion results in an encoded protein thereof lacking p-NBE activity.

11. The host cell of claim 8, wherein partial deletion of a gene encoding a p-NBE polypeptide comprises deleting nucleotides of the p-NBE gene encoding amino acid residues 1-163 of SEQ ID NO: 2, deleting nucleotides of the p-NBE gene encoding amino acid residues 164-326 of SEQ ID NO: 2 or deleting nucleotides of the p-NBE gene encoding amino acid residues 327-489 of SEQ ID NO: 2.

12. The host cell of claim 8, wherein partial deletion of a gene encoding a p-NBE polypeptide comprises deleting an acetyl esterase (AE) domain encoded by the p-NBE gene.

13. The host cell of claim 12, wherein the AE domain is comprised within amino acid residues 85-211 of SEQ ID NO: 2.

14. The host cell of claim 8, wherein partial deletion of a gene encoding a p-NBE polypeptide comprises deleting one or more codons of the gene which encode a p-NBE substrate binding pocket.

15. The host cell of claim 8, wherein partial deletion of a gene encoding a p-NBE polypeptide comprises deleting one or more codons of the gene which encode a p-NBE substrate binding pocket.

16. The host cell of claim 1, wherein the recombinant polypeptide comprising β-galactosidase activity or transgalactosylating activity is selected from the group consisting of a *Bifidobacterium bifidum* polypeptide comprising 90% sequence identity to SEQ ID NO: 4, SEQ ID NO: 6, SEQ ID NO: 8, SEQ ID NO: 10, SEQ ID NO: 12, SEQ ID NO: 14 or SEQ ID NO: 16, a *Kluyveromyces lactis* polypeptide comprising 90% sequence identity to SEQ ID NO: 17, an *Aspergillus oryzae* polypeptide comprising 90% sequence identity to SEQ ID NO: 18 and a *Lactobacillus delbrueckii* polypeptide comprising 90% sequence identity to SEQ ID NO: 26.

17. The host cell of claim 1, wherein the recombinant polypeptide comprising β-galactosidase activity or transgalactosylating activity is encoded by a polynucleotide comprising 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 25.

18. The host cell of claim 1, wherein the host cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens,* B akibai, *B. clarkii, B. pseudofirmus, B. lehensis, B. megaterium, B. coagulans, B. circulans, B. gibsonii,* and *B. thuringiensis*.

19. The host cell of claim 1, wherein the host cell is *Bacillus subtilis*.

20. The host cell of claim 1, wherein the host cell is further modified to be deficient in detectable lipase side activities, phospholipase side activities, cellulase side activities, pectinase side activities, amylase side activities, protease side activities and/or mannanase side activities.

21. The host cell of claim 1, wherein the host cell comprises an expression vector comprising a polynucleotide encoding a polypeptide comprising β-galactosidase activity or transgalactosylating activity.

22. The host cell of claim 20, wherein the expression vector is integrated into the genome of the host cell.

23. The host cell of claim 1, wherein the host cell is transformed with a polynucleotide construct encoding a polypeptide comprising β-galactosidase activity or transgalactosylating activity.

24. A method for producing a polypeptide composition having β-galactosidase activity or transgalactosylating activity, wherein the polypeptide composition does not comprise detectable para-nitrobenzylesterase (p-NBE) activity therein, the method comprising:
   (a) providing a parental *Bacillus* host cell comprising an introduced polynucleotide construct encoding a recombinant polypeptide having β-galactosidase activity or transgalactosylating activity,
   (b) modifying the *Bacillus* host cell of step (a) by deleting, disrupting or down-regulating a gene encoding a p-NBE polypeptide comprising at least 60% sequence identity to the p-NBE polypeptide of SEQ ID NO: 2,
   (c) culturing the modified host cell of step (b) under conditions suitable to express the polypeptide having β-galactosidase activity or transgalactosylating activity, and
   (d) isolating the polypeptide having β-galactosidase activity or transgalactosylating activity,
   wherein the isolated polypeptide composition having β-galactosidase activity or transgalactosylating activity does not comprise detectable p-NBE activity.

25. A method for producing a polypeptide composition having β-galactosidase activity or transgalactosylating activity, wherein the polypeptide composition does not comprise detectable para-nitrobenzylesterase (p-NBE) activity therein, the method comprising:
   (a) obtaining a parental *Bacillus* host cell and modifying the parental cell by deleting, disrupting or down-regulating a gene encoding a p-NBE polypeptide comprising at least 60% sequence identity to the p-NBE polypeptide of SEQ ID NO: 2,
   (b) introducing into the modified cell of step (a) an expression construct encoding a polypeptide having β-galactosidase activity or transgalactosylating activity,
   (c) culturing the host cell of step (b) under conditions suitable to express the polypeptide having β-galactosidase activity or transgalactosylating activity, and
   (d) isolating the polypeptide having β-galactosidase activity or transgalactosylating activity,
   wherein the isolated polypeptide composition having β-galactosidase activity or transgalactosylating activity does not comprise detectable p-NBE activity.

26. The method of claim 24 or claim 25, wherein the modification comprises a deletion, disruption or down-regulation of a gene encoding a p-NBE polypeptide comprising at least 60% sequence identity to the p-NBE polypeptide of SEQ ID NO: 2.

27. The method of claim 24 or claim 25, wherein the modification comprises a complete or partial deletion a gene encoding a p-NBE polypeptide comprising at least 60% sequence identity to the p-NBE polypeptide of SEQ ID NO: 2.

28. The method of claim 24 or claim 25, wherein the polypeptide comprising β-galactosidase activity or transgalactosylating activity is selected from the group consisting of a *Bifidobacterium bifidum* polypeptide comprising 90% sequence identity to SEQ ID NO: 4, SEQ ID NO: 6, SEQ ID NO: 8, SEQ ID NO: 10, SEQ ID NO: 12, SEQ ID NO: 14 or SEQ ID NO: 16, a *Kluyveromyces lactis* polypeptide comprising 90% sequence identity to SEQ ID NO: 17, an *Aspergillus oryzae* polypeptide comprising 90% sequence identity to SEQ ID NO: 18 and a *Lactobacillus delbrueckii* polypeptide comprising 90% sequence identity to SEQ ID NO: 26.

29. The method of claim 24 or claim 25, wherein the polypeptide comprising β-galactosidase activity or transgalactosylating activity is encoded by a polynucleotide comprising 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 25.

30. The method of claim 24 or claim 25, wherein the host cell selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens,* B akibai, *B. clarkii, B. pseudofirmus, B. lehensis, B. megaterium, B. coagulans, B. circulans, B. gibsonii,* and *B. thuringiensis.*

31. The method of claim 24 or claim 25, wherein the host cell is further modified to be deficient in detectable lipase side activities, phospholipase side activities, cellulase side activities, pectinase side activities, amylase side activities, protease side activities and/or mannanase side activities.

* * * * *